US012564837B2

(12) United States Patent
Krueger et al.

(10) Patent No.:     US 12,564,837 B2
(45) Date of Patent:          Mar. 3, 2026

(54) INTEGRATED COMPACT CELL SORTER

(71) Applicant: CYTEK BIOSCIENCES, INC.,
Fremont, CA (US)

(72) Inventors: Glen Krueger, Fremont, CA (US);
David Vrane, Fremont, CA (US)

(73) Assignee: Cytek Biosciences, Inc., Fremont, CA
(US)

( * ) Notice:      Subject to any disclaimer, the term of this
patent is extended or adjusted under 35
U.S.C. 154(b) by 294 days.

(21) Appl. No.: 17/665,480

(22) Filed:      Feb. 4, 2022

(65) Prior Publication Data

US 2022/0268688 A1      Aug. 25, 2022

Related U.S. Application Data

(60) Provisional application No. 63/172,330, filed on Apr.
8, 2021, provisional application No. 63/258,065, filed
(Continued)

(51) Int. Cl.
C12M 1/00          (2006.01)
B01L 3/00          (2006.01)
(Continued)

(52) U.S. Cl.
CPC ...  B01L 3/502761 (2013.01); B01L 3/502715
(2013.01); C12M 47/04 (2013.01);
(Continued)

(58) Field of Classification Search
CPC ......... B01L 3/502761; B01L 3/502715; B01L
2300/0654; B01L 2300/0663;
(Continued)

(56) References Cited

U.S. PATENT DOCUMENTS

2004/0062685 A1      4/2004  Norton et al.
2005/0180885 A1*    8/2005  Tateishi ............. G01N 15/1404
                                                                       422/68.1
(Continued)

FOREIGN PATENT DOCUMENTS

BR          P10017624 B1      11/2000
CN          111337416 A       6/2020
(Continued)

OTHER PUBLICATIONS

Baharlou, Simin; "International Preliminary Report On Patentabil-
ity" and "Written Opinion"; PCT/US2022/070542; Aug. 3, 2023; 18
pages.

*Primary Examiner* — Michelle M Iacoletti
*Assistant Examiner* — Judy Dao Tran
(74) *Attorney, Agent, or Firm* — Alford Law Group, Inc.;
Tobi Clinton

(57)          ABSTRACT

A system includes a flow cell and a fluidics system under
pressure causing sheath and sample biological fluids to flow.
The fluidics system includes a gas bubble remover to
remove and eliminate gas bubbles in the sheath fluid. The
flow cell receives sheath fluid from the fluidics system,
wherein the sample biological fluid flows with cells or
particles through the flow cell to be surrounded by the sheath
fluid. A deflection chamber under the flow cell receives
drops of the sample biological fluid and sheath fluid out of
the flow cell to selectively deflect one or more of the drops
along one or more deflection paths. A droplet deposition unit
system in communication with the deflection chamber
receives the selectively deflected drops in the stream of the
sample biological fluid with the one or more biological cells
or particles into one or more containers.

20 Claims, 41 Drawing Sheets

Related U.S. Application Data on Apr. 8, 2021, provisional application No. 63/172,072, filed on Apr. 7, 2021, provisional application No. 63/146,562, filed on Feb. 5, 2021.

(51) Int. Cl.

| | |
|---|---|
| *G01N 15/14* | (2006.01) |
| *G01N 15/1434* | (2024.01) |
| *G01N 15/01* | (2024.01) |
| *G01N 15/10* | (2006.01) |
| *G01N 15/1404* | (2024.01) |
| *G01N 15/1409* | (2024.01) |
| *G01N 15/149* | (2024.01) |
| *G01N 33/49* | (2006.01) |

(52) U.S. Cl.

CPC ......... *G01N 15/14* (2013.01); *G01N 15/1436* (2013.01); *B01L 2300/0654* (2013.01); *B01L 2300/0663* (2013.01); *B01L 2300/0681* (2013.01); *B01L 2300/0829* (2013.01); *B01L 2300/1805* (2013.01); *B01L 2300/1894* (2013.01); *C12Q 2565/626* (2013.01); *G01N 15/01* (2024.01); *G01N 2015/1006* (2013.01); *G01N 2015/1028* (2024.01); *G01N 15/1409* (2024.01); *G01N 2015/1418* (2013.01); *G01N 15/149* (2024.01); *G01N 33/4915* (2013.01)

(58) Field of Classification Search

CPC ..... B01L 2300/0681; B01L 2300/0829; B01L 2300/1822; B01L 3/0241; B01L 2200/0652; B01L 2300/1805; B01L 2300/1894; B01L 2300/1844; C12M 47/04; G01N 15/14; G01N 15/1436; G01N 15/01; G01N 15/1409; G01N 15/149; G01N 2015/1028; G01N 15/1434; G01N 15/1459; G01N 2015/1486; G01N 2015/1438; G01N 2015/1006

See application file for complete search history.

(56) References Cited

U.S. PATENT DOCUMENTS

| | | | |
|---|---|---|---|
| 2006/0163069 A1* | 7/2006 | Prak ..................... | G01N 21/05 |
| | | | 204/601 |
| 2007/0148043 A1 | 6/2007 | Norton et al. | |
| 2008/0240994 A1 | 10/2008 | Shohmi et al. | |
| 2009/0107893 A1 | 4/2009 | Schembri et al. | |
| 2010/0118298 A1* | 5/2010 | Bair ................... | G01N 15/1404 |
| | | | 356/246 |
| 2012/0103112 A1 | 5/2012 | Vrane et al. | |
| 2016/0320287 A1* | 11/2016 | Buchanan .......... | G01N 15/1404 |
| 2017/0248508 A1* | 8/2017 | Ward ................. | G01N 33/5091 |
| 2017/0297023 A1* | 10/2017 | Lin .................... | G01N 15/1459 |
| 2018/0156710 A1 | 6/2018 | Vrane et al. | |
| 2018/0156711 A1 | 6/2018 | Vrane | |
| 2018/0255709 A1* | 9/2018 | Topps ................... | A01G 9/249 |
| 2018/0299367 A1* | 10/2018 | Yan ........................ | G01J 3/021 |
| 2020/0056979 A1 | 2/2020 | Ghazi | |
| 2020/0132590 A1 | 4/2020 | Dembski et al. | |

FOREIGN PATENT DOCUMENTS

| | | | | |
|---|---|---|---|---|
| EP | 1391717 A1 * | 2/2004 | ......... | G01N 15/1459 |
| WO | WO2020/091720 A1 | 7/2020 | | |

\* cited by examiner

*120*

*302A*               *302B*

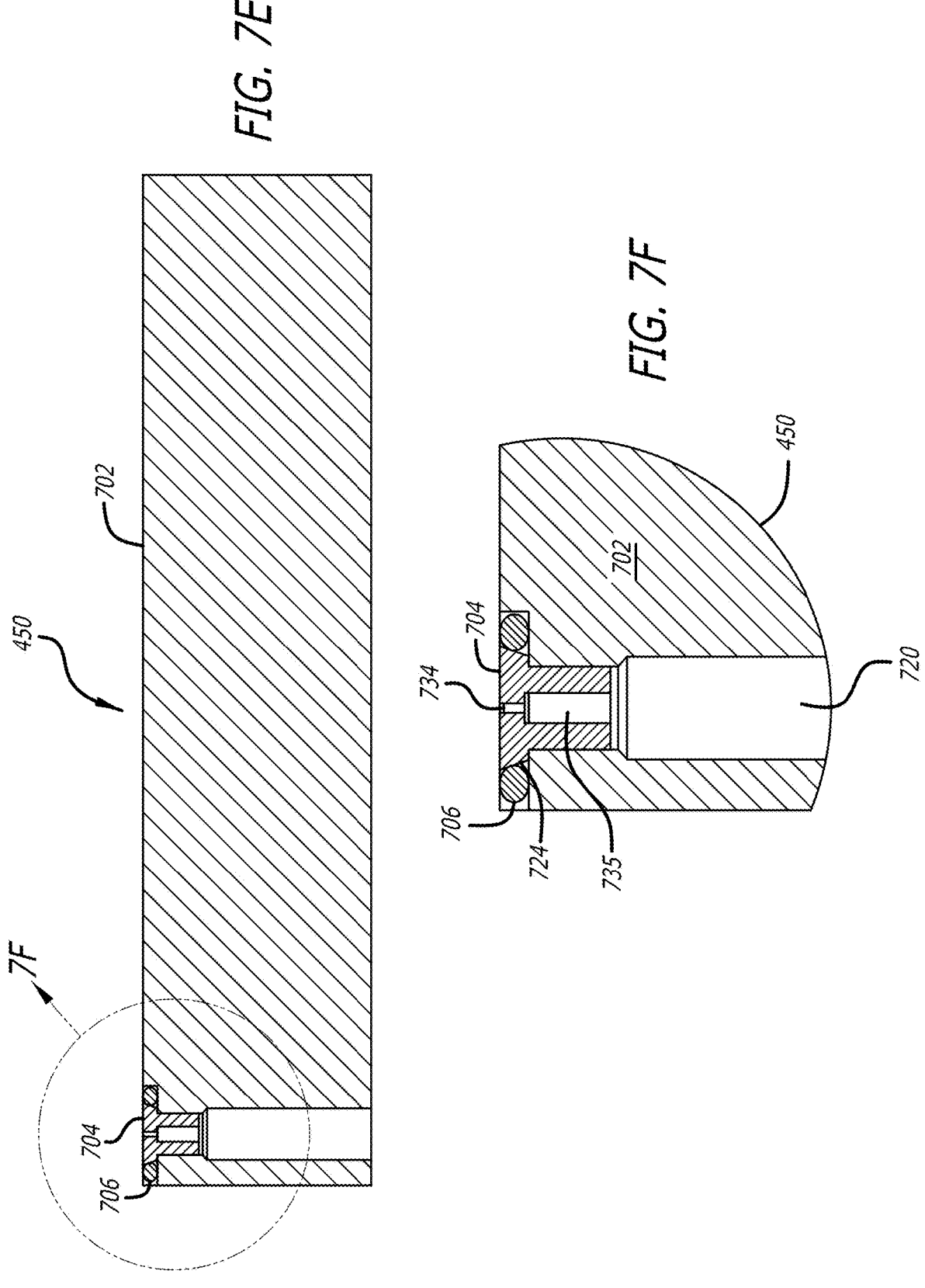

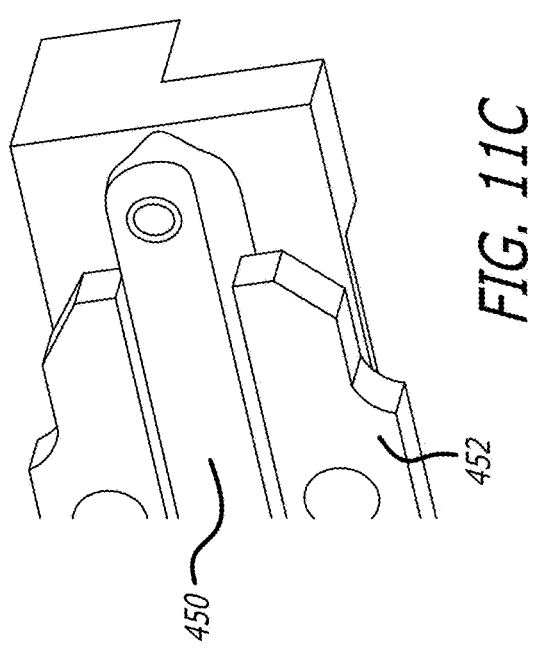
*FIG. 11C*
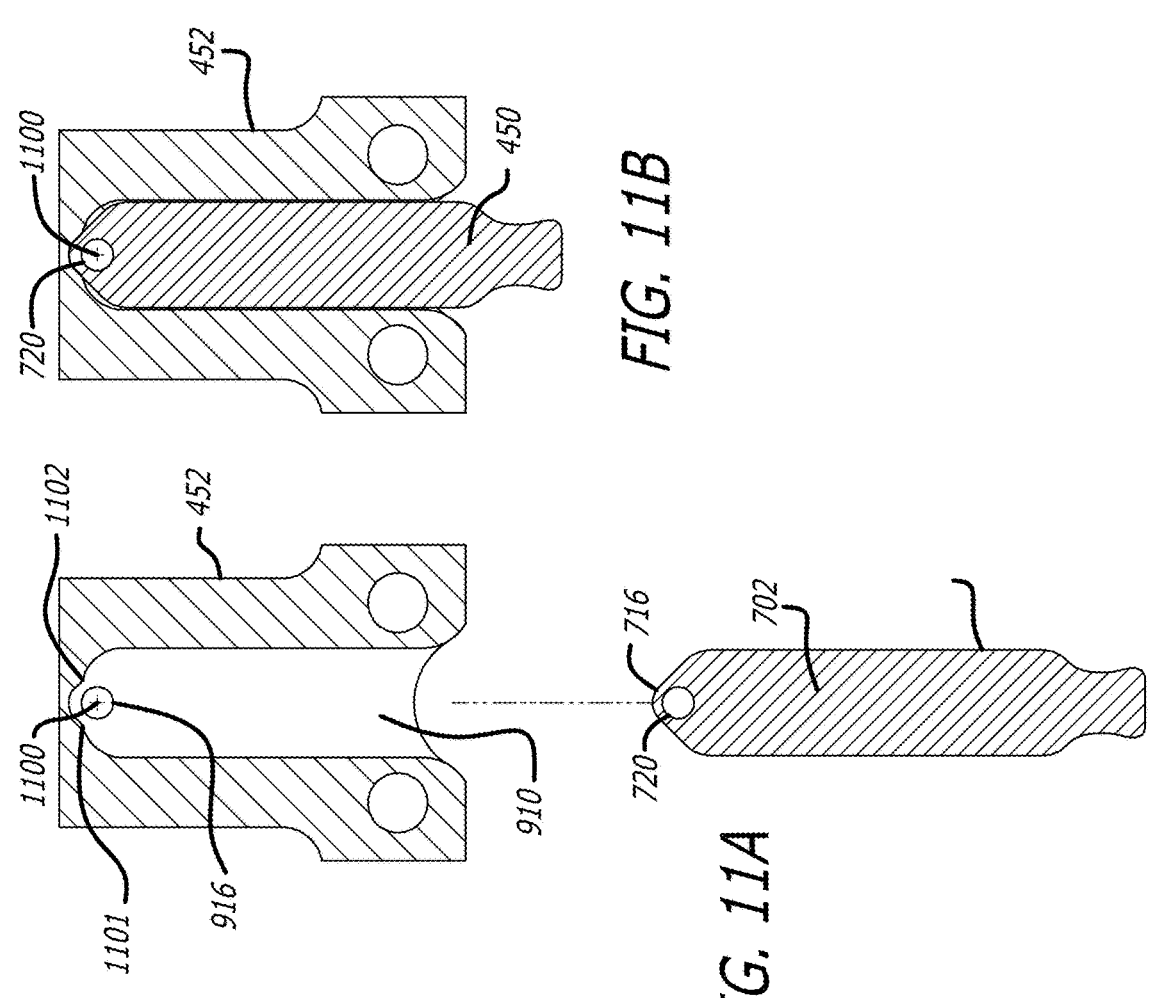
*FIG. 11B*
*FIG. 11A*

1

INTEGRATED COMPACT CELL SORTER

CROSS-REFERENCE TO RELATED APPLICATIONS

This patent application claims the benefit of United States (US) Provisional Patent Application No. 63/172,072 titled INTEGRATED COMPACT CELL SORTER filed on Apr. 7, 2021 by inventors Glen Krueger et al., incorporated herein by reference for all intents and purposes. This patent application claims the benefit of United States (US) Provisional Patent Application No. 63/172,330 titled INTEGRATED AIR FILTERING AND CONDITIONING OF DROPLET CHAMBER IN A COMPACT CELL SORTER filed on Apr. 8, 2021 by inventors Glen Krueger et al., incorporated herein by reference for all intents and purposes. This patent application claims the benefit of United States (US) Provisional Patent Application No. 63/258,065 titled INTEGRATED AIR FILTERING AND CONDITIONING OF DROPLET CHAMBER IN A COMPACT CELL SORTER filed on Apr. 7, 2021 by inventors Glen Krueger et al., incorporated herein by reference for all intents and purposes. This patent application claims the benefit of United States (US) Provisional Patent Application No. 63/146,562 titled LOADING SYSTEM WITH MAGNETICALLY COUPLED SAMPLE MOVER FOR FLOW CYTOMETRY AND CELL SORTER SYSTEMS filed on Feb. 5, 2021 by inventors Babak Honaryar et al., incorporated herein by reference for all intents and purposes.

FIELD

The embodiments of the invention relate generally to cell sorter systems.

BACKGROUND

Flow cytometry and cell sorting involves the optical measurement of cells or particles of a test sample carried in a fluid flow. Cell sorting further sorts out selected cells of interest into different containers (e.g., test tubes) for further usage (e.g., testing) or counting. The lab instruments that achieve these tasks are known as a flow cytometer and a cell sorter, also referred to as a sorting flow cytometer.

Oftentimes external supporting equipment is connected to a flow cytometer or cell sorter to safely operate them to be sure dangerous molecules or biological cells are not released into a lab. In other cases, temperature of molecules or biological cells under test needs to be maintained within a range. External supporting equipment is often connected to a flow cytometer or cell sorter to maintain an acceptable temperature range that does not damage the molecules or cells. However, the external supporting equipment comes at extra costs, including monetary, taking up space in a lab that could be used for other lab equipment or additional flow cytometers or cell sorters.

It is desirable to reduce the footprint of the flow cytometer/cell sorter so more can be placed in a lab and on desktops. Accordingly, a more compact integrated flow cytometer and cell sorter is desirable to improve upon prior systems.

SUMMARY

The embodiments are best summarized by the claims. However, a summary of some of the embodiments is provided here.

A system for flow cytometry or cell sorting is provided. The system comprises the following: a fluidics system under pressure to cause a sheath fluid and a sample biological fluid to flow, the fluidics system includes a gas bubble remover eliminating gas bubbles in the sheath fluid; a flow cell coupled in communication with the fluidics system to receive the sheath fluid, wherein a sample biological fluid flows with cells or particles through the flow cell to be surrounded by the sheath fluid, converted to drops and selectively charged for sorting; a deflection chamber under the flow cell to receive the drops of sample biological fluid and sheath fluid out of the flow cell, the deflection chamber to selectively deflect one or more of the drops along one or more deflection paths based on the selective charging of the drops; and a droplet deposition unit (DDU) system in communication with the deflection chamber to receive selectively deflected drops in the stream of the sample biological fluid with the one or more biological cells or particles into one or more containers.

In one embodiment, the flow cell includes a flow cell body coupled in communication with the fluidics system to receive the sheath fluid, the flow cell body having a conductive hose fitting in a drain (charging) port to selectively receive a charge to charge droplets, the flow cell body having a chamber with a circular cylindrical portion and a funnel portion, the funnel portion to form a fluid stream of the sample fluid surrounded by the sheath fluid out of a bottom side opening; a drop drive assembly coupled to the flow cell body, the drop drive assembly including a glass sample injection tube (SIT) inserted into the chamber of the flow cell body and having a first end located in the funnel portion of the chamber, the glass sample injection tube having a second end coupled in communication with the fluidics system to receive the sample fluid and inject the sample fluid into the funnel portion of the chamber; and a cuvette coupled to a base of the flow cell body, the cuvette having a flow channel adjacent the bottom side opening of the flow cell body, the cuvette to receive the fluid stream of the sample fluid surrounded by the sheath fluid out of the bottom side opening, the cuvette being transparent to light and allowing the sample fluid to undergo interrogation in the flow channel by a plurality of different lasers to determine a plurality of different types of cells or particles in the sample fluid.

In one embodiment, the flow cell includes the following: a flow cell body coupled around the drop drive assembly to receive the sample fluid from the sample injection tube, the flow cell body coupled in communication with the fluidics system to receive the sheath fluid, the flow cell body having a combined charging and drainage port to charge droplets in the sample fluid and drain sheath fluid, the flow cell body having a funnel portion to form a fluid stream of the sample fluid surrounded by the sheath fluid out of an opening; and a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein.

In one embodiment, the flow cell further includes the following: a nozzle assembly selectively engaged with the cuvette, the nozzle assembly having a nozzle and an O-ring around the nozzle selectively pressed against a face of the cuvette around the channel, the nozzle receiving the sample stream from the cuvette and forming sample drops out of the nozzle assembly; a carriage assembly slidingly coupled to the flow cell body, the carriage assembly to slidingly receive the nozzle assembly; and a linkage pivotally coupled to the carriage assembly and the flow cell body, the linkage including a lever arm to selectively engage the nozzle with the cuvette to receive a fluid stream and selectively disengage the nozzle from the cuvette to repair or replace the nozzle.

In one embodiment, the flow cell further includes the following: a lever hinge formed to be statically coupled to the flow cell body; a carriage release lever rotatably coupled to the lever hinge; and two lever arms rotatably coupled to the carriage release lever and to a carriage plate of the carriage assembly, wherein the two lever arms, the carriage plate, the carriage release lever, and the lever hinge have a kinematic linkage that enables the carriage assembly to maintain a vertical movement along the center axis.

In one embodiment, the flow cell further includes the following: a nozzle assembly having the following: a nozzle handle having a body with a gripping end and a nozzle end, the body having a through hole between top and bottom surfaces near the nozzle end with a partial gland in the top surface extending around the through hole, the partial gland having a slot extending out from the through hole to the nozzle end of the nozzle handle; a nozzle insert positioned in a portion of the through hole of the body of the nozzle handle, the nozzle insert having a circular body with a center nozzle orifice concentric with the through hole to flow drops of a sample fluid, and a beveled ring in a top surface extending out from the circular body; a gasket positioned in the partial gland against the beveled ring of the nozzle insert with a portion extending above the top surface of the nozzle insert and the top surface of the nozzle handle, the gasket to provide a seal around the center nozzle orifice; and wherein the slot extending out from the partial gland to the nozzle end facilitates removal of the gasket.

In one embodiment, the DDU system includes the following: a case or a housing with an open face surround by edges of the case, the case forming a portion of a containment chamber, the case having a top side opening aligned with the deflection chamber to receive the selectively deflected drops in the stream of the sample biological fluid into one or more containers in the containment chamber, a seal mounted around edges of the case, one or more hinges coupled to a bottom portion of the case, and a door coupled to the one or more hinges to pivot the door about the one or more hinges, the door when closed to press against the seal and close off the containment chamber from an external environment.

In one embodiment, the DDU system includes the following: an electromagnetic lock comprising at least one electromagnet mounted to the case and a metal latch coupled to an inside surface of the door, wherein the metal latch is attracted to the at least one electromagnet when the door is closed and the at least one electromagnet is energized.

In one embodiment, the DDU system includes a magnetic lock comprising at least one magnet mounted to the case and a metal latch coupled to an inside surface of the door, wherein the metal latch is attracted to the at least one magnet when the door is closed.

In one embodiment, the DDU system includes a sort collection holder to hold one or more test tubes in respective one or more deflection paths to collect the drops of the sample biological fluid and sheath fluid in the one or more test tubes.

In one embodiment, the DDU system includes a plate guide having a channel to allow one deflection path to collect the drops of the sample biological fluid and sheath fluid into one well of a plurality of wells in a well plate.

In one embodiment, the system further comprises an excitation optics system including a plurality of excitation channels each having a different laser device and one or more optical elements to direct different laser light to optical interrogation regions spaced apart along a line in a flow channel of the flow cell.

In one embodiment, the system further comprises the following: an excitation optics system including a first excitation channel having a first laser device emitting a first laser light to strike cells or particles attached to a first fluorescent dye; and a second excitation channel having a second laser device emitting a second laser light to strike cells or particles attached to a second fluorescent dye.

In one embodiment, the system further comprises an emission optics system including a plurality of detector arrays configured to receive light corresponding to cells or particles that are struck by the different laser light.

In one embodiment, the system further comprises an emission optics system including a plurality of detector arrays each having one or more optical elements to direct fluorescent light or scattered light (side and forward scatter light) to various electro-optical detectors.

A flow cytometer or cell sorter system is disclosed. The system comprises the following: a fluidics system under pressure to cause a sheath fluid and a sample fluid to flow, the fluidics system including a gas bubble remover eliminating gas bubbles in the sheath fluid; a flow cell coupled in communication with the fluidics system to receive the sheath fluid, wherein a sample fluid flows with cells or particles through the flow cell to be surrounded by the sheath fluid. The flow cell includes the following: a drop drive assembly including a sample injection tube (SIT), the sample injection tube coupled in communication with the fluidics system to receive the sample fluid; a flow cell body coupled around the drop drive assembly to receive the sample fluid from the sample injection tube, the flow cell body coupled in communication with the fluidics system to receive sheath fluid, the flow cell body having a charging port to charge droplets of the sample fluid, the flow cell body having a funnel portion to form a fluid stream of the sample fluid surrounded by the sheath fluid out of an opening; and a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein.

In one embodiment, the flow cell body is formed of an opaque (e.g., black) material to reduce background light reflection of ambient light towards a light detector.

In one embodiment, the opaque material of the flow cell body further reduces reflection of laser light towards the light detector.

In one embodiment, the opaque material is a black polymer.

In one embodiment, the gas bubble remover is a degasser.

In one embodiment, the sample injection tube is a glass sample injection tube.

In one embodiment, the flow cell further includes a nozzle assembly selectively engaged with the cuvette, the nozzle assembly having a nozzle and an O-ring around the nozzle selectively pressed against a face of the cuvette around the channel, the nozzle receiving the sample stream from the cuvette and forming sample drops out of the nozzle assembly.

In one embodiment, the flow cell further includes the following: a carriage assembly slidingly coupled to the flow cell body, the carriage assembly to slidingly receive the nozzle assembly; and a linkage pivotally coupled to the carriage assembly and the flow cell body, the linkage including a lever arm to selectively engage the nozzle with the cuvette to receive a fluid stream and selectively disengage with the nozzle from the cuvette to repair or replace the nozzle.

In one embodiment, the system is a flow cytometer, and the cuvette is transparent to light allowing the sample fluid to undergo interrogation in the flow channel by the plurality of different lasers to further determine counts of the plurality of different types of cells or particles in the sample fluid.

In one embodiment, the system is a cell sorter, and the cuvette is transparent to light allowing the sample fluid to undergo interrogation in the flow channel by the plurality of different lasers to further sort the plurality of different types of cells or particles in the sample fluid into different tubes or wells.

A flow cell body for a flow cytometer or a cell sorter is provided. The flow cell body comprises the following: a three-dimensional opaque (e.g., black) polymer body having top, bottom, left, right, front, and back sides. The opaque polymer body includes the following: a top side opening into a chamber to receive a drop drive assembly including a sample injection tube (SIT), wherein the chamber has an upper circular cylindrical portion and a lower funnel portion; two or more opposing top side openings receiving threaded inserts to engage two or more threaded bolts to hold a hub of the drop drive assembly coupled to the top side of the flow cell body; a left side port opening into the chamber adjacent a top of the lower funnel portion of the chamber, the left side port opening for fluid flow into or out of the chamber; a right side port opening into the chamber adjacent the top of the lower funnel portion of the chamber, the right side port opening for fluid flow out of or into the chamber; a bottom side opening into the chamber to allow a fluid stream to exit the chamber and the flow cell body; and wherein the lower funnel portion of the chamber forms the fluid stream out of the bottom side opening.

In one embodiment, the opaque body further includes two or more front side threaded openings to engage two or more threaded fasteners to hold a linear slide rail coupled to the front side of the flow cell body, wherein the linear slide rail to slidingly engage a nozzle carriage assembly.

In one embodiment, each of the two or more front side threaded openings receive a threaded insert to engage the two or more threaded fasteners.

In one embodiment, the front side of the flow cell body, the bracket to pivotally couple to a lever arm of a linkage to linearly move the nozzle carriage assembly up and down with respect to the flow body.

In one embodiment, each of the two or more front side threaded openings receive a threaded insert to engage the two or more threaded bolts.

In one embodiment, the opaque body further includes a shallow oval opening above the two or more front side threaded openings to receive an end of a spring loaded detent with an opposite end slidingly engaging a backside of the lever arm to maintain a selected position.

In one embodiment, the opaque body further includes a pocket opening in the bottom side to receive a cuvette and provide left side and right side views of a flow channel in the cuvette, and a circular gland around the bottom side opening to receive an O-ring that couples to and between the bottom side of the opaque body and the cuvette to seal around the bottom side opening and force fluid into the flow channel in the cuvette.

In one embodiment, the pocket opening in the opaque body further includes an upper arched cutaway to receive a microscope test instrument through the front side of the opaque body to view the flow channel in the cuvette.

In one embodiment, the opaque body further includes two or more front side through hole openings to the back side to receive two or more bolts to couple an objective lens assembly to the flow cell body.

In one embodiment, the opaque body further includes two or more front side through hole openings to the back side to receive two or more bolts to couple a bracket for a release lever to the flow cell body.

In one embodiment, the left side port opening into the chamber of the opaque body is a sheath inlet port to receive sheath fluid into the chamber, and the right side port opening into the chamber of the opaque body is a drain and charging port to drain sheath fluid from the chamber and charge droplets.

In one embodiment, the opaque body is opaque to visible light and either absorbs and/or avoids reflecting or light piping the visible light.

In one embodiment, the opaque body is further opaque to ultraviolet light and absorbs and/or avoids reflecting or light piping the ultraviolet light.

In one embodiment, the right side port opening is threaded to engage a conductive threaded hose fitting for the fluid flow out of or into the chamber that selectively receives a charge from a sort controller to selectively charge drops of sample fluid.

In one embodiment, the left side port opening is threaded to engage a threaded port fitting for the fluid flow into or out of the chamber.

A subsystem for a flow cytometer or cell sorter system is provided. The subsystem comprises the following: a carriage assembly including a mount having a through hole, wherein the mount is formed to register a nozzle assembly having a nozzle insert with a center nozzle orifice, wherein a gasket is coupled around a perimeter of the nozzle insert, and wherein the mount registers the nozzle assembly such that the center nozzle orifice and the through hole of the mount are concentric along a center axis; the carriage assembly further including a carriage plate statically coupled to the mount such that the carriage plate enables the mount to have vertical movement along the center axis, wherein the mount presses the gasket on the nozzle assembly against a lower side of a cuvette, and wherein the cuvette is formed to have a lower side facing the mount and an upper side coupled to a base of a flow cell body.

In one embodiment, the subsystem further comprises the following: a lever hinge formed to be statically coupled to the flow cell body; a carriage release lever rotatably coupled to the lever hinge; and two lever arms rotatably coupled to the carriage release lever and to the carriage plate of the carriage assembly, wherein the two lever arms, the carriage plate, the carriage release lever, and the lever hinge have a kinematic linkage that enables the mount of the carriage assembly to maintain the vertical movement along the center axis.

In one embodiment, the two lever arms may include a left lever arm having an end rotatably coupled to a left side of the carriage release lever and another end rotatably coupled to a left side of the carriage plate, and a right lever arm having an end rotatably coupled to a right side of the carriage release lever and another end rotatably coupled to a right side of the carriage plate.

In one embodiment, the carriage release lever is engaged by moving the carriage release lever in such a way that the kinematic linkage causes the mount to move upward toward the lower side of the cuvette, and when the carriage release is engaged, the gasket is pressed against the cuvette to cause a seal between the cuvette and the nozzle insert.

In one embodiment, the carriage release lever is disengaged by moving the carriage release lever in such a way that the kinematic linkage causes the mount to move downward away from the lower side of the cuvette, and when the carriage release is disengaged, the mount is positioned to register or unregister the nozzle assembly.

In one embodiment, the left lever arm includes a left spring that causes the left lever arm to apply a left force to the carriage plate, and the right lever arm includes a right spring that causes the right lever arm to apply a right force to the carriage plate.

In one embodiment, when the carriage release lever is engaged, the left force and the right force combine to cause the gasket on the nozzle assembly to apply a pressure to the cuvette, wherein the pressure is adjustable via the left spring and the right spring.

In one embodiment, when the pressure between the gasket and the cuvette is consistently precise within a tolerance.

In one embodiment, the kinematic linkage has a sufficiently high precision such that the vertical movement along the center axis is precise within a tolerance.

In one embodiment, the gasket is pressed against the cuvette to cause a seal between the cuvette and the nozzle insert, and the seal is sufficient to prevent misplaced liquids that exit the flow cell body from contacting surfaces outside the cuvette and the nozzle insert.

In one embodiment, the mount, the carriage plate, the lever hinge, the carriage release lever, and the two lever arms each comprise a corrosion resistant metal (e.g., stainless steel, titanium, etc.).

In one embodiment, a nozzle handle of the nozzle handle assembly has opposing side rails extending from left and right sides, and the mount has left and right slide slots to enable the side rails of the nozzle handle to slide into and out from the mount.

In one embodiment, a perimeter of the through hole of the mount includes a left nub formed to make a left point contact with a left end surface of a nozzle handle of the nozzle assembly, and a right nub formed to make a right point contact with a right end surface of the nozzle handle of the nozzle assembly.

In one embodiment, the left point contact and the second point contact are on a circumference of a circle, and the circle is concentric with the center nozzle orifice of the nozzle insert and the through hole of the mount.

In one embodiment, the first point contact and the second point contact maintain a registration with the mount such that the center nozzle orifice of the nozzle insert and the through hole of the mount remain concentric within a tolerance along the center axis.

In one embodiment, an objective lens is coupled to the flow cell body, and a cuvette gasket seals the objective lens to a back side of the cuvette.

A flow cytometer or cell sorter system is provided. The system comprises the following: a flow cell coupled in communication with the fluidics system to receive the sheath fluid, wherein a sample fluid flows with cells or particles through the flow cell to be surrounded by the sheath fluid, the flow cell including a flow cell body coupled around the drop drive assembly to receive the sample fluid from the sample injection tube, the flow cell body coupled in communication with the fluidics system to receive the sheath fluid, the flow cell body having charging port to selectively charge droplets of the sample fluid, the flow cell body having a funnel portion to form a fluid stream of the sample fluid surrounded by the sheath fluid out of an opening; a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein; and a nozzle assembly selectively engaged with the cuvette, the nozzle assembly having a nozzle and an O-ring around the nozzle selectively pressed against a face of the cuvette around the channel, the nozzle receiving the sample stream from the cuvette and forming sample drops out of the nozzle assembly.

In one embodiment, the system further comprises a fluidics system under pressure to cause a sheath fluid and a sample fluid to flow, the fluidics system including a gas bubble remover eliminating gas bubbles in the sheath fluid.

In one embodiment, the flow cell further includes a drop drive assembly including a sample injection tube (SIT), the sample injection tube coupled in communication with the fluidics system to receive the sample fluid.

In one embodiment, the flow cell further includes a carriage assembly slidingly coupled to the flow cell body, the carriage assembly to slidingly receive the nozzle assembly; and a linkage pivotally coupled to the carriage assembly and the flow cell body, the linkage including a lever arm to selectively engage the nozzle with the cuvette to receive a fluid stream and selectively disengage the nozzle from the cuvette to repair or replace the nozzle.

In one embodiment, the system further comprises a lever hinge formed to be statically coupled to the flow cell body; a carriage release lever rotatably coupled to the lever hinge; and two lever arms rotatably coupled to the carriage release lever and to a carriage plate of the carriage assembly, wherein the two lever arms, the carriage plate, the carriage release lever, and the lever hinge have a kinematic linkage that enables the carriage assembly to maintain a vertical movement along the center axis.

In one embodiment, the two lever arms include a left lever arm having an end rotatably coupled to a left side of the carriage release lever and another end rotatably coupled to a left side of the carriage plate, and a right lever arm having an end rotatably coupled to a right side of the carriage release lever and another end rotatably coupled to a right side of the carriage plate.

In one embodiment, the carriage release lever is engaged by moving the carriage release lever in such a way that the kinematic linkage causes the mount to move upward toward the lower side of the cuvette, and when the carriage release is engaged, the gasket is pressed against the cuvette to cause a seal between the cuvette and the nozzle insert.

In one embodiment, the carriage release lever is disengaged by moving the carriage release lever in such a way that the kinematic linkage causes the mount to move downward away from the lower side of the cuvette, and when the carriage release is disengaged, the mount is positioned to register or unregister the nozzle assembly.

In one embodiment, the left lever arm includes a left spring that causes the left lever arm to apply a left force to the carriage plate, and the right lever arm includes a right spring that causes the right lever arm to apply a right force to the carriage plate.

In one embodiment, when the carriage release lever is engaged, the left force and the right force combine to cause the gasket on the nozzle assembly to apply a pressure to the cuvette, wherein the pressure is adjustable via the left spring and the right spring.

In one embodiment, the pressure between the gasket and the cuvette is consistently precise within a tolerance.

In one embodiment, the kinematic linkage has a sufficiently high precision such that the vertical movement along the center axis is precise within a tolerance.

In one embodiment, the gasket is pressed against the cuvette to cause a seal between the cuvette and the nozzle insert, and the seal is sufficient to prevent misplaced liquids that exit the flow cell body from contacting surfaces outside the cuvette and the nozzle insert.

In one embodiment, the mount, the carriage plate, the lever hinge, the carriage release lever, and the two lever arms each comprise a corrosion resistant metal (e.g., stainless steel, titanium, etc.).

In one embodiment, a nozzle handle of the nozzle handle assembly has opposing side rails extending from left and right sides, and the mount has left and right slide slots to enable the side rails of the nozzle handle to slide into and out from the mount.

In one embodiment, a perimeter of the through hole of the mount includes a left nub formed to make a left point contact with a left end surface of a nozzle handle of the nozzle assembly, and a right nub formed to make a right point contact with a right end surface of the nozzle handle of the nozzle assembly.

In one embodiment, the left point contact and the second point contact are on a circumference of a circle, and the circle is concentric with the center nozzle orifice of the nozzle insert and the through hole of the mount.

In one embodiment, the first point contact and the second point contact maintain a registration with the mount such that the center nozzle orifice of the nozzle insert and the through hole of the mount remain concentric within a tolerance along the center axis.

In one embodiment, an objective lens is coupled to the flow cell body, and a cuvette gasket seals the objective lens to a back side of the cuvette.

A nozzle assembly for a cell sorter system is provided. The nozzle assembly comprises the following: a nozzle handle having a body with a gripping end and a nozzle end, the body having a through hole between top and bottom surfaces near the nozzle end with a partial gland in the top surface extending around the through hole, the partial gland having a slot extending out from the through hole to the nozzle end of the nozzle handle; a nozzle insert positioned in a portion of the through hole of the body of the nozzle handle, the nozzle insert having a circular body with a center nozzle orifice concentric with the through hole to flow drops of a sample fluid, and a beveled ring in a top surface extending out from the circular body; a gasket positioned in the partial gland against the beveled ring of the nozzle insert with a portion extending above the top surface of the nozzle insert and the top surface of the nozzle handle, the gasket to provide a seal around the center nozzle orifice; and wherein the slot extending out from the partial gland to the nozzle end facilitates removal of the gasket.

In one embodiment, the partial gland has a circular shape through the slot, and the gasket is an O-ring with the portion that extends above the top surface of the nozzle handle and the nozzle insert.

In one embodiment, the slot in the nozzle handle facilitates removal and replacement of the gasket by enabling a user to lift up on the gasket by using a finger or a tool.

In one embodiment, the nozzle handle is formed to be slid and registered onto a mount having a through hole.

In one embodiment, registration of the nozzle handle is completed by positioning the nozzle handle such that the center nozzle orifice of the nozzle insert and the through hole of the mount are concentric along a center axis.

In one embodiment, a lower portion of the body of the nozzle handle has opposing side rails extending from left and right sides to slide into and out from left and right side slots in the mount.

In one embodiment, the nozzle end of the nozzle handle is formed to make a first point contact with a first nub on the mount, and a second point contact with a second nub on the mount, wherein the first point contact and the second point contact are on a perimeter of the through hole.

In one embodiment, the first point contact and the second point contact are on a circumference of a circle, and the circle is concentric with the center nozzle orifice of the nozzle insert and the through hole of the mount.

In one embodiment, the first point contact and the second point contact maintain a registration with the mount such that the center nozzle orifice of the nozzle insert and the through hole of the mount remain concentric within a tolerance.

In one embodiment, the mount enables the nozzle assembly to undergo vertical movement up toward a cuvette coupled to a base of a flow cell body, and the movement toward the cuvette positions a portion of the gasket to be pressed against a face of the cuvette to provide a seal around the nozzle insert.

In one embodiment, the center nozzle orifice of the nozzle insert can receive a sample stream from a flow channel in the cuvette and form sample droplets to exit the nozzle insert and through the through hole in the mount.

In one embodiment, the nozzle insert comprises ceramic.

In one embodiment, the nozzle handle comprises polyether ether ketone (PEEK).

In one embodiment, the gasket comprises ethylene propylene diene monomer (EPDM) rubber.

A flow cytometer or cell sorter system is provided. The system comprises the following: a fluidics system under pressure to cause a sheath fluid and a sample fluid to flow, the fluidics system including a gas bubble remover eliminating gas bubbles in the sheath fluid; and a flow cell coupled in communication with the fluidics system to receive the sheath fluid, wherein a sample fluid flows with cells or particles through the flow cell to be surrounded by the sheath fluid. The flow cell includes the following: a flow cell body coupled in communication with the fluidics system to receive the sheath fluid, the flow cell body having charging port to selectively charge droplets of sample fluid, the flow cell body having a chamber with a circular cylindrical portion and a funnel portion, the funnel portion to form a fluid stream of the sample fluid surrounded by the sheath fluid out of a bottom side opening; a drop drive assembly coupled to the flow cell body, the drop drive assembly including a glass sample injection tube (SIT) inserted into the chamber of the flow cell body and having a first end located in the funnel portion of the chamber, the glass sample injection tube having a second end coupled in communication with the fluidics system to receive the sample fluid and inject the sample fluid into the funnel portion of the chamber; and a cuvette coupled to a base of the flow cell body, the cuvette having a flow channel adjacent the bottom side opening of the flow cell body, the cuvette to receive the fluid stream of the sample fluid surrounded by the sheath fluid out of the bottom side opening, the cuvette being transparent to light and allowing the sample fluid to undergo interrogation in the flow channel by a plurality of different lasers to determine a plurality of different types of cells or particles in the sample fluid.

In one embodiment, the first end of the glass sample injection tube located in the funnel portion of the chamber is chamfered to allow a sample fluid to flow out and merge with sheath stream in a stable manner.

In one embodiment, the drop drive assembly further includes an O-ring to seal around the glass sample injection tube.

In one embodiment, the glass sample injection tube has an external diameter in the range of 2.05 millimeters to 3.18 millimeters with an internal diameter opening in the range of 0.17 millimeters to 0.45 millimeters and a total length of not more than 70 mm as to provide sufficient stiffness to avoid breakage during installation and service.

In one embodiment, the drop drive assembly further includes a low cost standard off the shelf O-ring to seal around the glass sample injection tube having an unstretched inside diameter in the range of 2.0 millimeters to 3.0 millimeters, dependent upon the outside diameter of the glass sample injection tube, or just small enough to provide sealing contact around the glass sample injection tube.

In one embodiment, the flow cell further includes a nozzle assembly including a nozzle adjacent the cuvette, the nozzle having a flow channel concentric with an axis through the flow channel in the cuvette to receive, the nozzle to form drops of sample fluid and sheath fluid out of the flow cell.

In one embodiment, the system further includes a deflection chamber under the flow cell to receive the drops of sample fluid and sheath fluid out of the flow cell, the deflection chamber to deflect one or more of the drops along one or more deflection paths.

In one embodiment, the system further includes a sort collection holder to hold one or more test tubes in respective one or more deflection paths to collect the drops of the sample fluid and sheath fluid in the one or more test tubes.

In one embodiment, the system further includes a plate guide having a channel to allow one deflection path to collect the drops of the sample fluid and sheath fluid into one well of a plurality of wells in a well plate.

A drop drive assembly for a flow cytometer or cell sorter system is provided. The drop drive assembly comprises the following: an outer metal (piezo) hub having a center opening extending from top to bottom through an extended hollow circular plug; an insulating spacer extended over the extended hollow circular plug up to a flange in a base of the outer metal hub; a hollow piezoelectric cylindrical transducer having a first end coupled over the extended hollow circular plug up to insulating spacer, an inner terminal of the hollow piezoelectric cylindrical transducer coupled to the extended hollow circular plug to form an electrical connection to the outer metal hub; an insulated cylindrical sealing base having an extended hollow circular plug coupled into a second end of the hollow piezoelectric cylindrical transducer, the insulated cylindrical sealing base having a gland ring around a through hole opposite the extended hollow circular plug, the insulated cylindrical sealing base having a groove around an outer cylindrical surface; a hollow cylindrical glass sample injection tube (SIT) having a first end inserted into and through the center opening in the outer metal (piezo) hub, the hollow piezoelectric cylindrical transducer, and the through hole in the insulated cylindrical sealing base; a first sealing O-ring mounted in the groove around in the outer cylindrical surface of the insulated cylindrical sealing base, the first sealing O-ring to engage a cylindrical wall of a cylindrical chamber to seal fluids away from the hollow piezoelectric cylindrical transducer; and a second sealing O-ring mounted in the gland ring in the insulated cylindrical sealing base around the hollow cylindrical glass sample injection tube (SIT) to seal fluids away from the hollow piezoelectric cylindrical transducer.

In one embodiment, each of the extended hollow circular plugs includes a plurality of ridges to retain adhesive glue between the circular plug and the inner surface of the hollow piezoelectric cylindrical transducer.

In one embodiment, the drop drive assembly further comprises a sample input port coupled in communication with a first end of the hollow cylindrical glass sample injection tube (SIT), the sample input port to receive a sample fluid including a plurality of cells or particles to flow through the hollow cylindrical glass sample injection tube (SIT).

In one embodiment, the first end of the hollow cylindrical glass sample injection tube (SIT) is chamfered to allow a sample fluid to flow out and merge with sheath stream in a stable manner.

In one embodiment, the wall of the center opening in the outer metal hub is partially threaded and the assembly further comprises the following: a hollow PEEK sleeve (SIT Shell Isolator) with a top flange over the second end of the glass SIT in the center opening of the outer metal (piezo) hub to isolate the glass SIT; a third sealing O-ring over second end of the glass SIT butted up against the top flange of the hollow PEEK sleeve; and a pipe adapter (SIT hub) having an opening at a first end to receive the second end of the glass SIT, the pipe adapter further having external threads at the first end to engage the internal threads in the center opening of the outer metal (piezo) hub to compress the third sealing O-ring against the top flange to seal around and hold the glass SIT in position therein, the pipe adapter having an internal female fitting at a second end opposite the first end.

In one embodiment, the internal female fitting of the pipe adapter is adapted to receive tubing with a ferrule around the tubing.

In one embodiment, the internal female thread detail of the drop drive can receive male threaded pipe adapters with either an integrated for separate ferrules.

In one embodiment, the outer metal (piezo) hub further has two or more through-holes around the center opening to receive threaded bolts or screws to couple the drop drive assembly to a flow cell body.

In one embodiment, the outer metal (piezo) hub further has a side opening leading to a bottom opening and the drop drive assembly further comprises the following: an electrical jack mounted in the side opening and coupled to the outer metal hub, the electrical jack having a terminal electrically coupled to an outer terminal of the hollow piezoelectric cylindrical transducer by an electrical wire routed through the bottom opening.

In one embodiment, the first, second, and third sealing O-rings are rubber O-rings. In another embodiment, the first, second, and third sealing O-rings are silicon O-rings.

BRIEF DESCRIPTIONS OF THE DRAWINGS

Various embodiments are illustrated by way of example, and not by way of limitation, in the Figures of the accompanying drawings.

FIG. 7E is a cross-sectional view of the nozzle assembly.

FIG. 7F is a magnified view of a portion of cross-sectional view of the nozzle assembly.

FIGS. 11A-11B are cross-sectional views of engagement/disengagement of the nozzle assembly with the nozzle mount of the flow cell.

FIG. 11C is a perspective view of the nozzle assembly registered with the nozzle mount of the flow cell.

FIGS. 12C-121 are respectively left, back, front, right, cross-sectional, bottom, and top views of the flow cell body.

It will be recognized that some or all of the Figures are for purposes of illustration and do not necessarily depict the actual relative sizes or locations of the elements shown. The Figures are provided for the purpose of illustrating one or more embodiments with the explicit understanding that they will not be used to limit the scope or the meaning of the claims.

DETAILED DESCRIPTION

In the following detailed description of the embodiments, numerous specific details are set forth. However, it will be obvious to one skilled in the art that the embodiments may be practiced without these specific details. In other instances, well known methods, procedures, components, and circuits have not been described in detail so as not to unnecessarily obscure aspects of the embodiments. The various sections of this description are provided for organizational purposes. However, many details and advantages apply across multiple sections.

System Overview

Figure 1A:
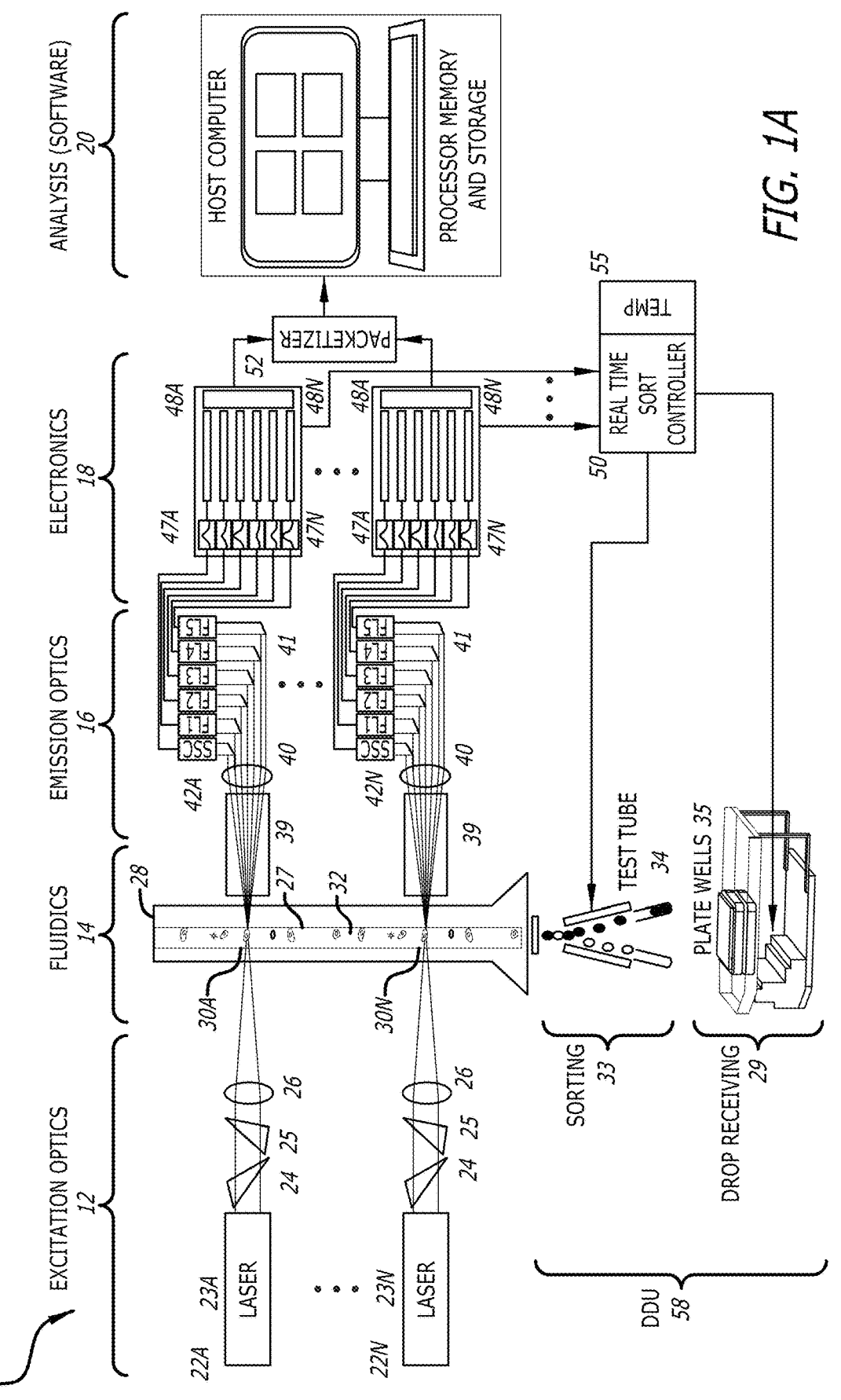
FIG. 1A is a basic conceptual diagram of a cell sorter system (a sorting flow cytometer system) and a flow cytometer system is shown.

FIG. 1A is a basic conceptual diagram of a cell sorter system (sorting flow cytometer) 10. Five major subsystems of the system 10 include an excitation optics system 12, a fluidics system 14, an emission optics system 16, an acquisition system 18, and an analysis system 20. The fluidics system 14 can include a sample loading system (not shown), an interrogating system 28, a cell sorting system 33, and a drop receiving system 29. Generally, a "system" and "subsystem" includes (electrical, mechanical, and electro-mechanical) hardware devices, software devices, or a combination thereof.

The excitation optics system 12 includes, for example, a plurality (e.g., two to five) of excitation channels 22A-22N each having a different laser device 23A-23N and one or more optical elements 24-26 to direct the different laser light to optical interrogation regions 30A-30N spaced apart along a line in a flow channel 27 of a flow cell 28. Example optical elements of the one or more one or more optical elements 24-26 include an optical prism and an optical lens. The excitation optics system 12 illuminates an optical interrogation region 30 in a flow cell 28. The fluidics system 14 carries a fluid sample 32 surrounded by a sheath fluid through each of a plurality of optical interrogation regions 30A-30N in the flow cell/flow channel.

The emission optics system 16 includes a plurality of detector arrays 42A-42N each of which, for example, includes one or more optical elements 40, such as an optical fiber and one or more lenses to direct fluorescent light and/or (forward, side, back) scattered light to various electro-optical detectors (transducers), including a side scatter (SSC) channel detector and a plurality (e.g., 16, 32, 48, 64) of fluorescent wavelength range optical detectors in each array, such as a first fluorescent optical detector (FL1) receiving a first wavelength range of fluorescent light, a second fluorescent optical detector (FL2) receiving a second wavelength range of fluorescent light, a third fluorescent optical detector (FL3) receiving a third wavelength range of fluorescent light, a fourth fluorescent optical detector (FL4) receiving a fourth wavelength range of fluorescent light, a fifth fluorescent optical detector (FL5) receiving a fifth wavelength range of fluorescent light, and so on to an Nth fluorescent optical detector (FLN) receiving an Nth wavelength range of fluorescent light. Each of the detector arrays 42A-42N receives light corresponding to the cells/particles that are struck and/or one or more fluorescent dyes that attached thereto and excited by the differing laser light in interrogation regions/points 30A-30N along the flow channel 27 of the flow cell 28 by each of the corresponding plurality of lasers 23A-23N. The emission optics system 16 gathers photons emitted or scattered from passing cells/particles and/or a fluorescent dyes attached to the cells/particles. The emission optics system 16 directs and focuses these collected photons onto the electro-optical detectors SSC, FL1, FL2, FL3, FL4, and FL5 in each detector array, such as by fiber optic (optical fibre) cables 39, one or more one or more lenses 40, and one or more mirrors/filters 41. Electro-optical detector SSC is a side scatter channel detector detecting light that scatters off the cell/particle. The electro-optical detectors FL1, FL2, FL3, FL4, and FL5 are fluorescent detectors may include band-pass, or long-pass, filters to detect a particular and differing fluorescence wavelength ranges from the different fluorescent dyes excited by the different lasers. Each electro-optical detector converts photons into electrical pulses and sends the electrical pulses to the acquisition (electronics) system 18.

For each detector array 42A-42N, the acquisition (electronics) system 18 includes one or more analog to digital converters 47A-47N and one or more digital storage devices 48A-48N that can provide a plurality of detector channels (e.g., 16, 32, 48 or 64 channels) of spectral data signals. The spectral data signals can be signal processed (e.g., digitized by the A/Ds) and time stamped, and packeted together by a packetizer 52 into a data packet corresponding to each cell/particle in the sample). These data packets for each cell/particle can be sent by the acquisition (electronics) system 18 to the analysis system 20 for further signal processing (e.g., converted/transformed from time domain to wavelength domain) and overall analysis. Alternatively, or conjunctively, time stamped digital spectral data signals from each channel that is detected can be directly sent to the analysis system 20 for signal processing.

The analysis system 20 includes a processor, memory, and data storage to store the data packets of time stamped digital spectral data associated with the detected cells/particles in the sample. The analysis system 20 further includes software with instructions executed by the processor to convert/transform data from the time domain to data in a wavelength/frequency domain and stich/merge data together to provide an overall spectrum for the cell/particle/dyes excited by the different lasers and sensed by the detector arrays. With detection of the type of cell/particle through the one or more fluorescent dyes attached thereto, a count of the cells/particles can be made in a sample processed by a flow cytometer and/or cell sorter.

In some cases, it is desirable to sort out the cells in a sample for further analysis with a cell sorter (sorting flow cytometer). Accordingly, the spectral data signals can also be processed by a real time sort controller 50 in the acquisition (electronics) system 18 and used to control a sorting system 33 to sort cells or particles into one or more test tubes 34. In which case, the sorting system 33 is in communication with the real time sort controller 50 of the acquisition (electronics) system 18 to receive control signals. Instead of test tubes 34, the spectral data signals can also be processed by the real time sort controller 50 of the acquisition (electronics) system 18 and used to control both the sorting system 33 and a droplet deposition system 29 to sort cells or particles into wells 35 of a moving capture tray/plate. In which case, both the droplet deposition system 29 and the sorting system 33 are in communication with the acquisition (electronics) system 18 to receive control signals. In an alternate embodiment, the analysis system 20 can generate these control signals from analyzing the spectral data signals in order to sort out different cells/molecules and control the sorting system 33 and the droplet deposition system 29 to capture the drops of samples with cells/particles into one or more wells 35 of the plurality of wells in the capture tray/plate.

U.S. patent application Ser. No. 15/817,277 titled FLOW CYTOMETERY SYSTEM WITH STEPPER FLOW CONTROL VALVE filed by David Vrane on Nov. 19, 2017, now issued as U.S. patent Ser. No. 10/871,438; U.S. patent application Ser. No. 15/659,610 titled COMPACT DETECTION MODULE FOR FLOW CYTOMETERS filed by Ming Yan et al. on Jul. 25, 2017; and U.S. patent application Ser. No. 15/942,430 COMPACT MULTI-COLOR FLOW CYTOMETER HAVING COMPACT DETECTION MODULE filed by Ming Yan et al. on Mar. 30, 2018, each of which disclose exemplary flow cytometer systems and subsystems all which are incorporated herein by reference for all intents and purposes. U.S. Pat. No. 9,934,511 titled Rapid Single Cell Based Parallel Biological Cell Sorter issued to Wenbin Jiang on Jun. 19, 2016, discloses a cell sorter system that is incorporated herein by reference for all intents and purposes.

Compact Cell Sorter

Figure 1B:
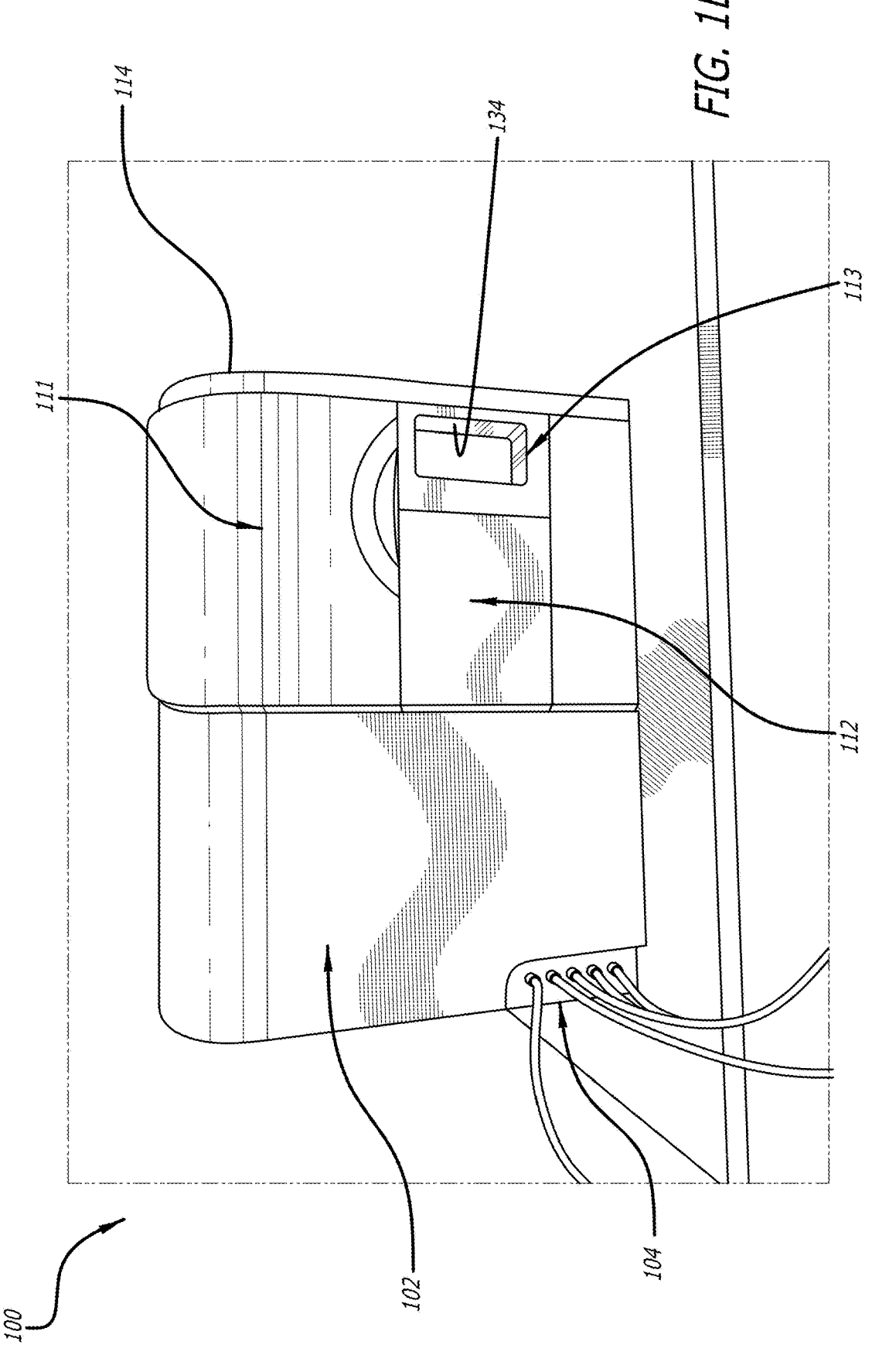
FIG. 1B is front view of a compact cell sorter system with its various doors in a closed state.

FIG. 1B illustrates a front view of an integrated compact cell sorter system 100. The integrated compact cell sorter system 100 includes a chassis/frame 101 (see FIG. 1C) to support the various systems and subsystems of the cell sorter. A fluidics panel/door 102, a flow cell door 111, a droplet deposition unit (DDU) door 112, and a sample input door 113 are pivotally coupled to the chassis/frame 101 to cover over and seal various chambers of the cell sorter system. One or more side panels 114 are used to cover over other portions of the chassis/frame and the subsystems therein in a more fixed manner. A fluidics input/output panel 104 connects the cell sorter system 100 to external fluid tanks and an external gas supply, such as a pressurized air supply.

Figure 1C:
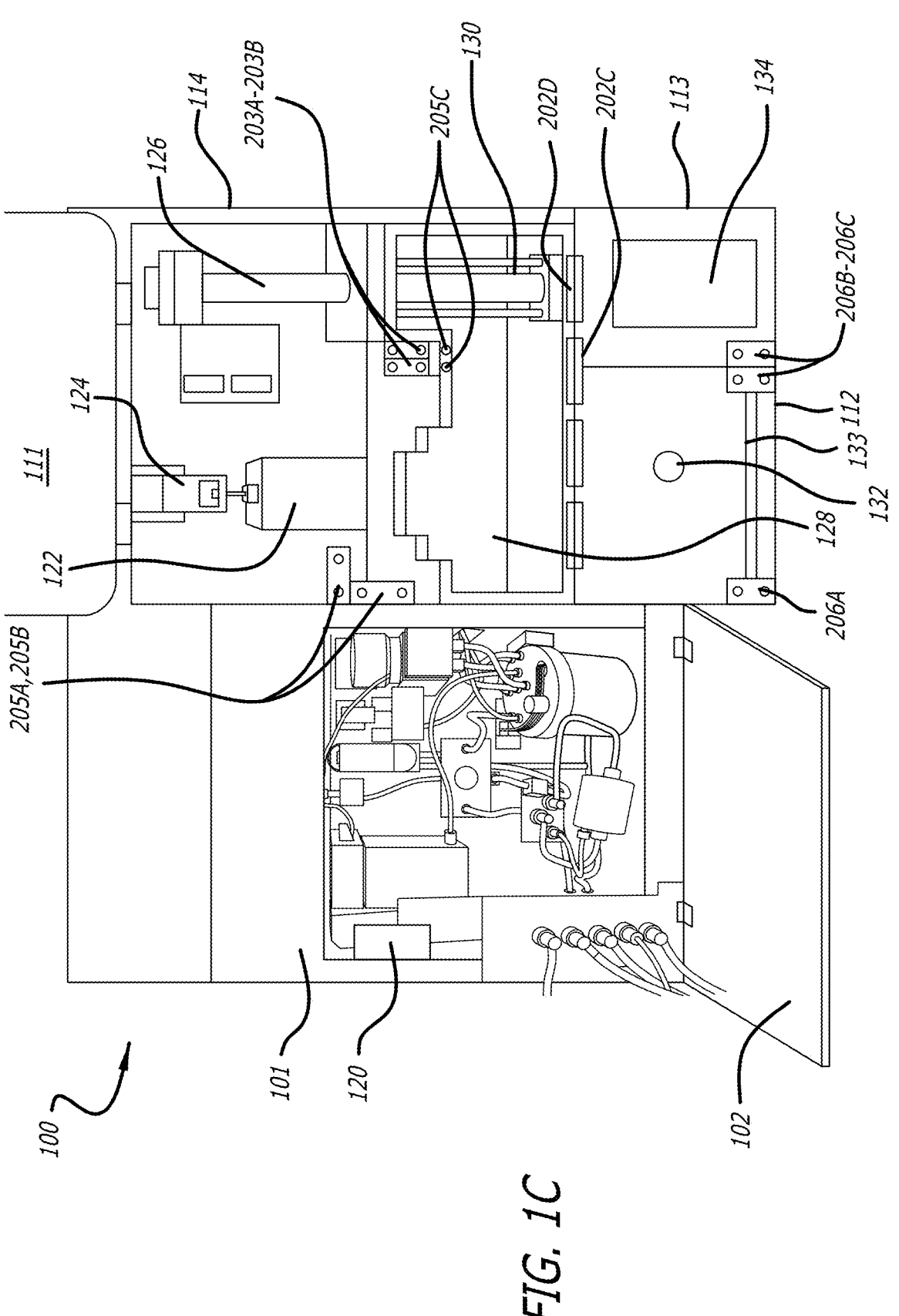
FIG. 1C is front view of a compact cell sorter system with its various doors in an open state.

Referring now to FIG. 1C, a front view of the integrated complex cell sorter system 100 is shown with opened doors and panels removed. The fluidics panel/door 102, the flow cell door 111, the DDU door 112, and the sample input door 113 of the integrated compact cell sorter system 100 are pivoted to an open position around hinges to reveal the various systems and subsystems of the cell sorter system. The integrated compact cell sorter system 100 includes a fluidics bucket 120 (part of the fluidics system 1800 of FIG. 18), a deflection chamber (unit) 122, a flow cell 124, a sample pressure chamber 126 a droplet deposition unit (DDU) chamber or collection chamber 128, a sample input station (SIS) 130, and a sort collection camera 132. The sample input door 113 has a window 134 through which a sample tube can be viewed if mounted in the SIS 130. The DDU door 112 has a sort collection camera 132 that can view left and right deflected drops fall out of a slot in the deflection chamber 122 and into the DDU chamber 128 to be collected by test tubes or wells in a well plate.

The fluidics bucket 120 (part of the fluidics system 1800 of FIG. 18) includes a gas bubble remover eliminating gas bubbles in the sheath fluid. The fluidics bucket 120 is further discussed with reference to FIGS. 3A-3B. The fluidics system 1800 (discussed in FIG. 18) is under pressure to cause a sheath fluid and a sample biological fluid to flow.

The flow cell 124 is coupled in communication with the fluidics bucket 120 to receive the sheath fluid. A sample biological fluid flows with cells or particles through the flow cell 124 to be surrounded by the sheath fluid. The flow cell 124 is further discussed with reference to FIGS. 4A-4G.

The deflection chamber 122 is under the flow cell 124 to receive the drops of sample biological fluid and sheath fluid out of the flow cell 124. The deflection chamber 122 selectively deflects one or more of charged drops away from the center stream path along one or more deflection paths. The deflection chamber 122 is further discussed with reference to FIGS. 16A-16B.

The droplet deposition unit (DDU) chamber/system 128 is in communication with the deflection chamber 122 to receive selectively deflected drops in the stream of the sample biological fluid with the one or more biological cells or particles into one or more containers. The DDU chamber 128 is further discussed with reference to FIGS. 2A-2B.

In one embodiment, the flow cell 124 includes a flow cell body coupled in communication with the fluidics system to receive the sheath fluid, the flow cell body having charging port to charge the droplets, the flow cell body having a chamber with a circular cylindrical portion and a funnel portion, the funnel portion to form a fluid stream of the sample fluid surrounded by the sheath fluid out of a bottom side opening; a drop drive assembly coupled to the flow cell body, the drop drive assembly including a glass sample injection tube (SIT) inserted into the chamber of the flow cell body and having a first end located in the funnel portion of the chamber, the glass sample injection tube having a second end coupled in communication with the fluidics system to receive the sample fluid and inject the sample fluid into the funnel portion of the chamber; and a cuvette coupled to a base of the flow cell body, the cuvette having a flow channel adjacent the bottom side opening of the flow cell body, the cuvette to receive the fluid stream of the sample fluid surrounded by the sheath fluid out of the bottom side opening, the cuvette being transparent to light and allowing the sample fluid to undergo interrogation in the flow channel by a plurality of different lasers to determine a plurality of different types of cells or particles in the sample fluid.

In one embodiment, the flow cell 124 includes the following: a flow cell body coupled around the drop drive assembly to receive the sample fluid from the sample injection tube, the flow cell body coupled in communication with the fluidics system to receive the sheath fluid, the flow cell body having a charging port to charge the droplets, the flow cell body having a funnel portion to form a fluid stream of the sample fluid surrounded by the sheath fluid out of an opening; and a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein.

In one embodiment, the flow cell 124 further includes the following: a nozzle assembly selectively engaged with the cuvette, the nozzle assembly having a nozzle and an O-ring around the nozzle selectively pressed against a face of the cuvette around the channel, the nozzle receiving the sample stream from the cuvette and forming sample drops out of the nozzle assembly; a carriage assembly slidingly coupled to the flow cell body, the carriage assembly to slidingly receive the nozzle assembly; and a linkage pivotally coupled to the carriage assembly and the flow cell body, the linkage including a lever arm to selectively engage the nozzle with the cuvette to receive a fluid stream and selectively disengage the nozzle from the cuvette to repair or replace the nozzle.

In one embodiment, the flow cell 124 further includes the following: a lever hinge formed to be statically coupled to the flow cell body; a carriage release lever rotatably coupled to the lever hinge; and two lever arms rotatably coupled to the carriage release lever and to a carriage plate of the carriage assembly, wherein the two lever arms, the carriage plate, the carriage release lever, and the lever hinge have a kinematic linkage that enables the carriage assembly to maintain a vertical movement along the center axis.

In one embodiment, the flow cell 124 further includes the following: a nozzle assembly having the following: a nozzle handle having a body with a gripping end and a nozzle end, the body having a through hole between top and bottom surfaces near the nozzle end with a partial gland in the top surface extending around the through hole, the partial gland having a slot extending out from the through hole to the nozzle end of the nozzle handle; a nozzle insert positioned in a portion of the through hole of the body of the nozzle handle, the nozzle insert having a circular body with a center nozzle orifice concentric with the through hole to flow drops of a sample fluid, and a beveled ring in a top surface extending out from the circular body; a gasket positioned in the partial gland against the beveled ring of the nozzle insert with a portion extending above the top surface of the nozzle insert and the top surface of the nozzle handle, the gasket to provide a seal around the center nozzle orifice; and wherein the slot extending out from the partial gland to the nozzle end facilitates removal of the gasket.

In one embodiment, the DDU system 128 includes the following: a case or a housing with an open face surround by edges of the case, the case forming a portion of a containment chamber, the case having a top side opening aligned with the deflection chamber to receive the selectively deflected drops in the stream of the sample biological fluid into one or more containers in the containment chamber, a seal mounted around edges of the case, one or more hinges coupled to a bottom portion of the case, and a door coupled to the one or more hinges to pivot the door about the one or more hinges, the door when closed to press against the seal and close off the containment chamber from an external environment.

In one embodiment, the DDU system 128 includes the following: an electromagnetic lock comprising at least one electromagnet mounted to the case and a metal latch coupled to an inside surface of the door, wherein the metal latch is attracted to the at least one electromagnet when the door is closed and the at least one electromagnet is energized.

In one embodiment, the DDU system 128 includes a magnetic lock comprising at least one magnet mounted to the case and a metal latch coupled to an inside surface of the door, wherein the metal latch is attracted to the at least one magnet when the door is closed.

DDU Chamber

Figure 2A:
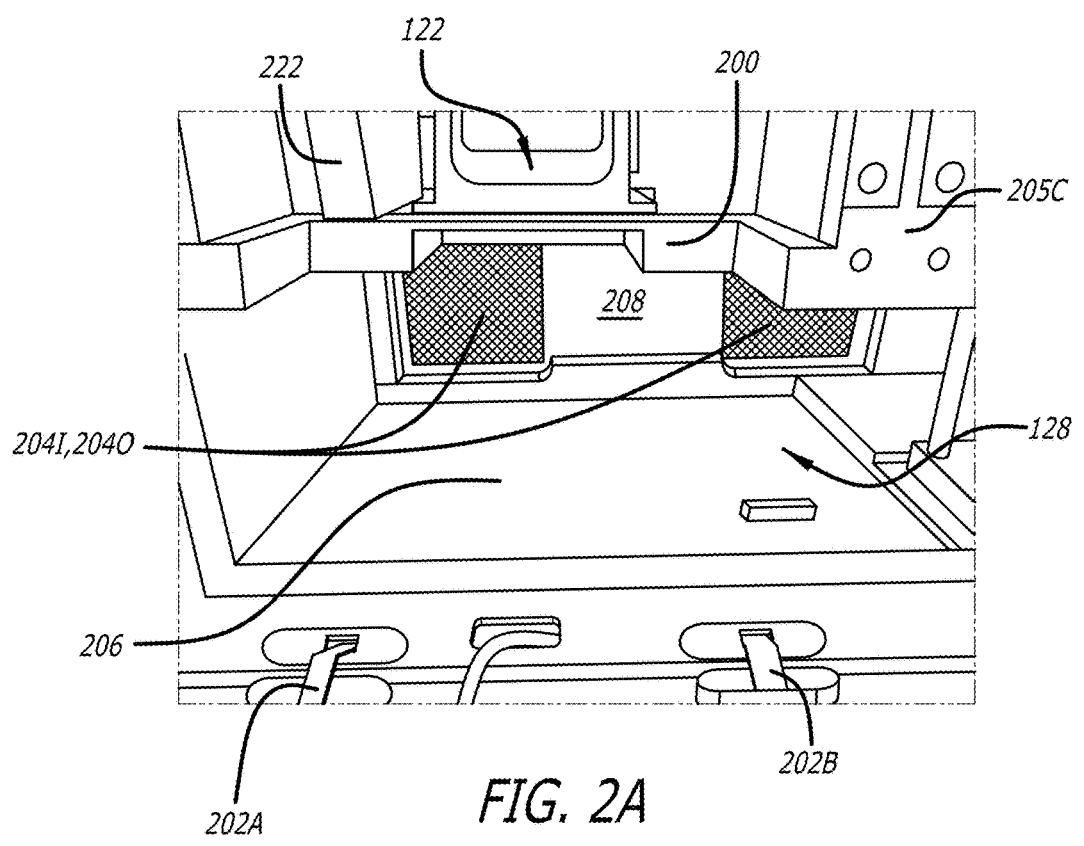
FIGS. 2A-2B are views of the droplet deposition unit (DDU) of the compact cell sorter system with the DDU door and the sample input door open.

FIG. 2A illustrates a portion of the deflection chamber 122 with its door 222 being open. The DDU chamber 128 of the cell sorter 100 is viewable with both the doors 112-113 pivoted to open positions. Openings in a back wall 208 of the DDU chamber 128 show an input air filter 2041 and an output air filter 2040 mounted within tunnels leading to an air conditioning chamber. Behind the wall 208 are one or more fans and at least one heating/air conditioning element to force the air through the air filters and maintain a desirable range of temperatures of the sample in the SIS 130 and the sorted cells/molecules in the DDU chamber 128.

At a base of the DDU chamber 128 is a separation plate 206 that separates a driver mechanism under the separation plate from the DDU chamber 128. Under the separation plate 206 are magnetic control mechanisms to control movement of a magnetically coupled puck 210 shown in FIG. 2B. A magnetic loading system for the DDU chamber and the magnetically coupled puck 210 is disclosed by U.S. provisional patent application No. 63/146,562, titled LOADING SYSTEM WITH MAGNETICALLY COUPLED SAMPLE MOVER FOR FLOW CYTOMETRY AND CELL SORTER SYSTEMS filed on Feb. 5, 2021 by Babak Honaryar et al., and incorporated herein by reference for all intents and purposes. Movement of the magnetically coupled puck 210 is controlled underneath the separation plate 206 by the magnetic loading system.

Figure 2B:
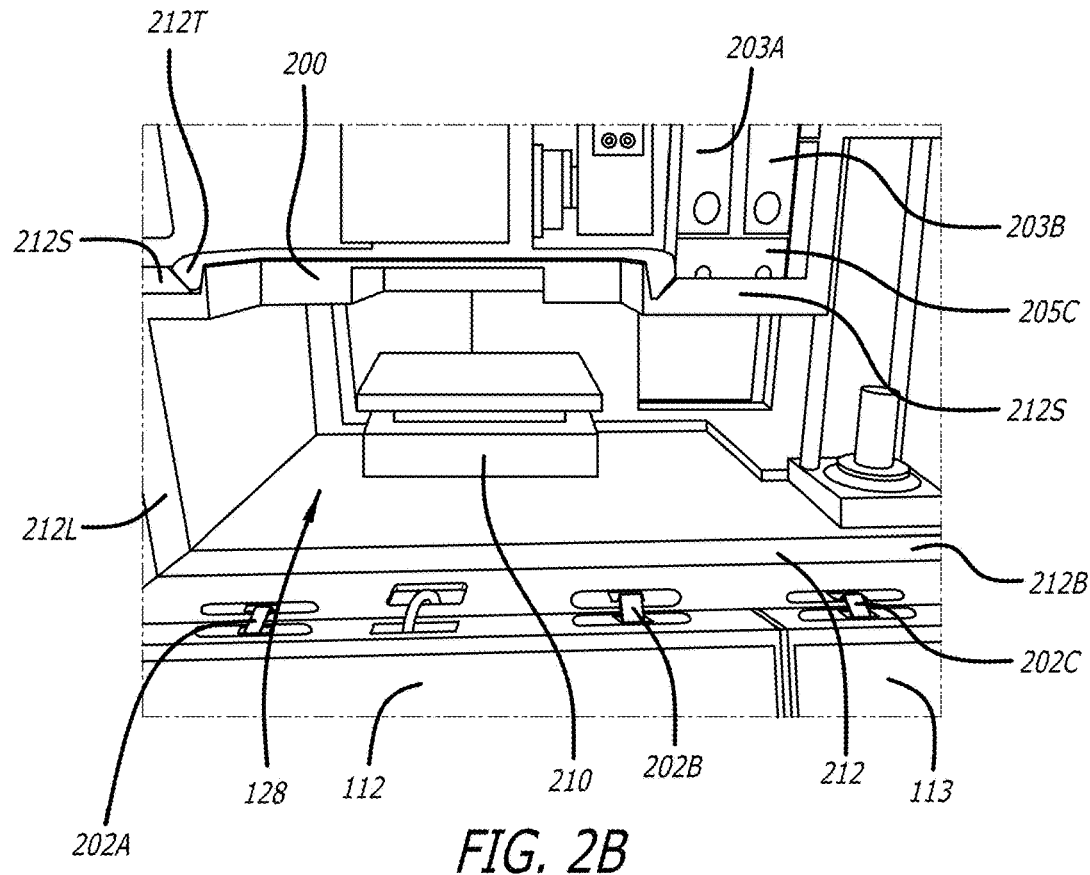

FIG. 2B illustrates a seal 212 that is mounted along edges of the DDU chamber 128 and the sample input station 130 to provide air resistive seal when the DDU door 112 and sample door 113 are closed. The DDU door 112 has a shelf 133 (shown in FIG. 1C) that presses down on a top seal portion 212T when closed. Other portions of the seal 212, such as the bottom portion 212B and side portions 212S, 212L, are pushed on by the doors 112-113 and squeezed up against the edges of the DDU chamber 128. With the doors closed, the DDU chamber 128 is sealed off from the ambient air of the environment (e.g., laboratory) where the cell sorter 100 is stationed. Furthermore, the DDU chamber 128 and SIS 130 are under negative pressure from a vacuum to additionally help prevent cells/molecules/gases from escaping out of the cell sorter into the ambient air of the environment, such as a laboratory.

The DDU door 112 and sample input door 113 provide a good seal to isolate the DDU chamber 128 from other parts of the flow cytometer/cell sorter 100 as well as the ambient environment. The sample drops sorted out and captured in the DDU chamber 128 may desire a temperature-controlled environment to maintain them. Furthermore, the cells that are captured may be a pathogen that are not desired to be an aerosol and escape into the environment. Accordingly, with the magnetic loading system and the sealed doors, the cell sorter can provide an integrated filtration system and temperature-controlled environment to the DDU chamber 128.

Fluidics Bucket [WEA Left Off Here]

Figure 3A:
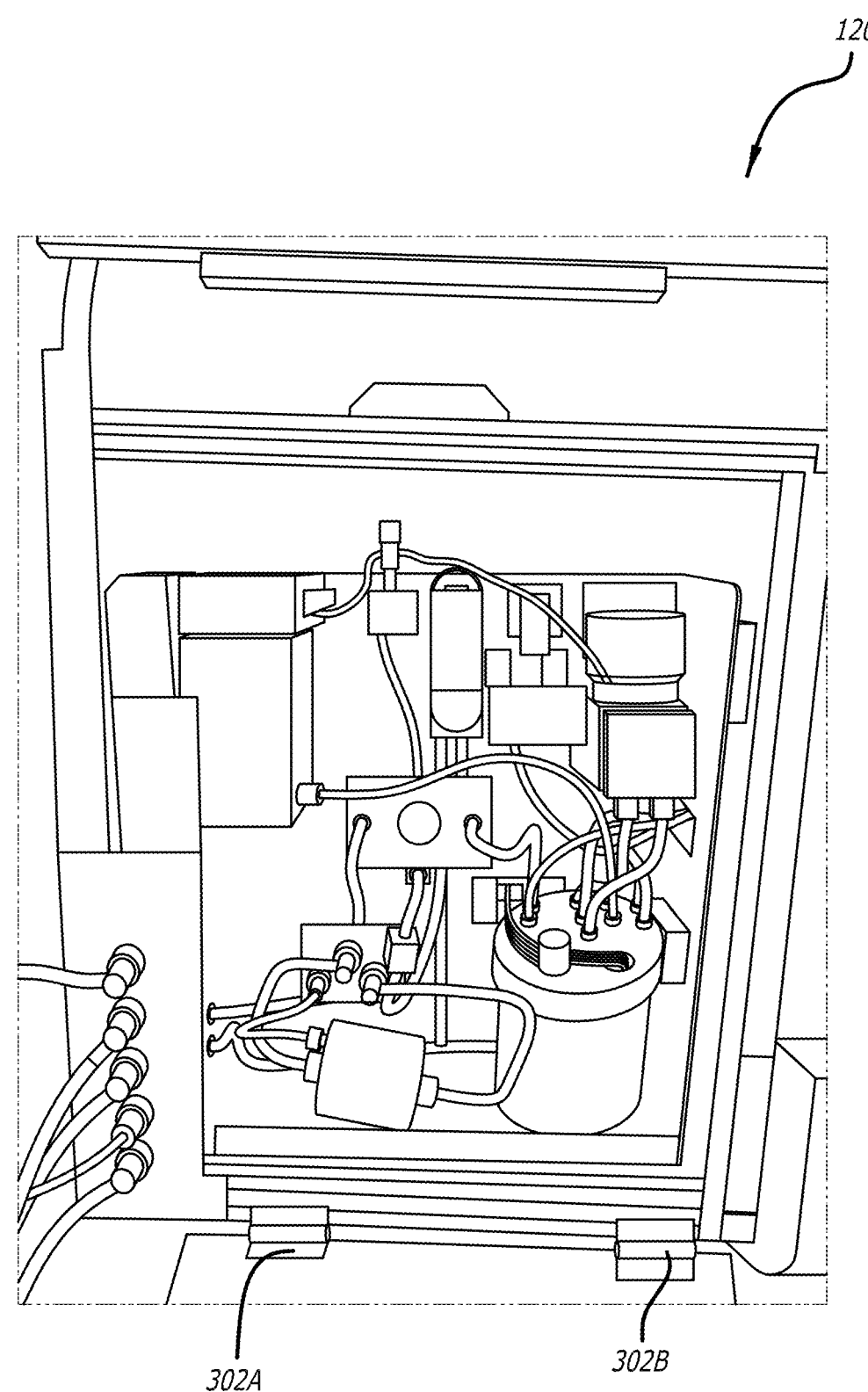
FIGS. 3A-3B are views of the fluidics bucket in the fluidics system of the compact cell sorter system.
Figure 3B:
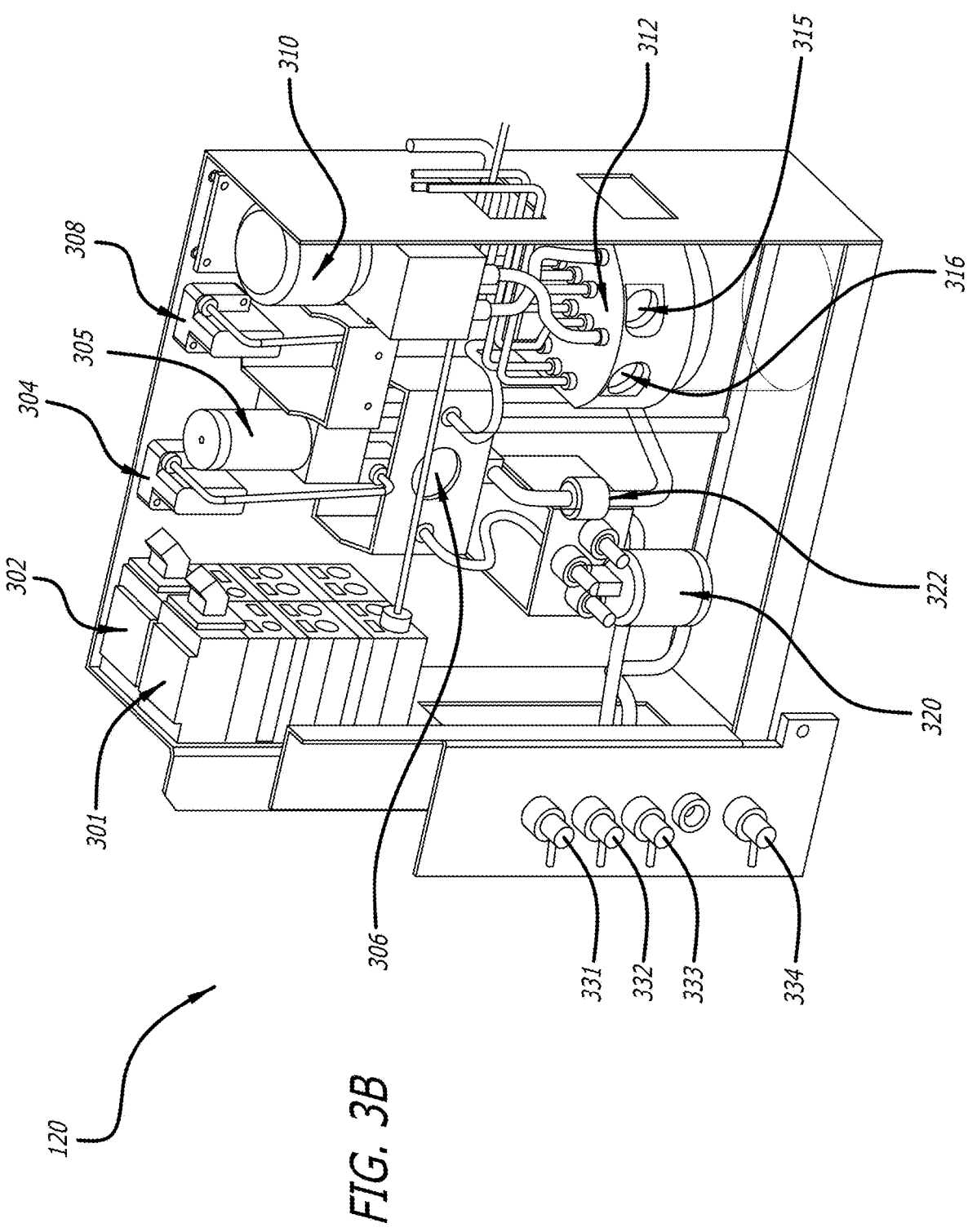
Figure 18:
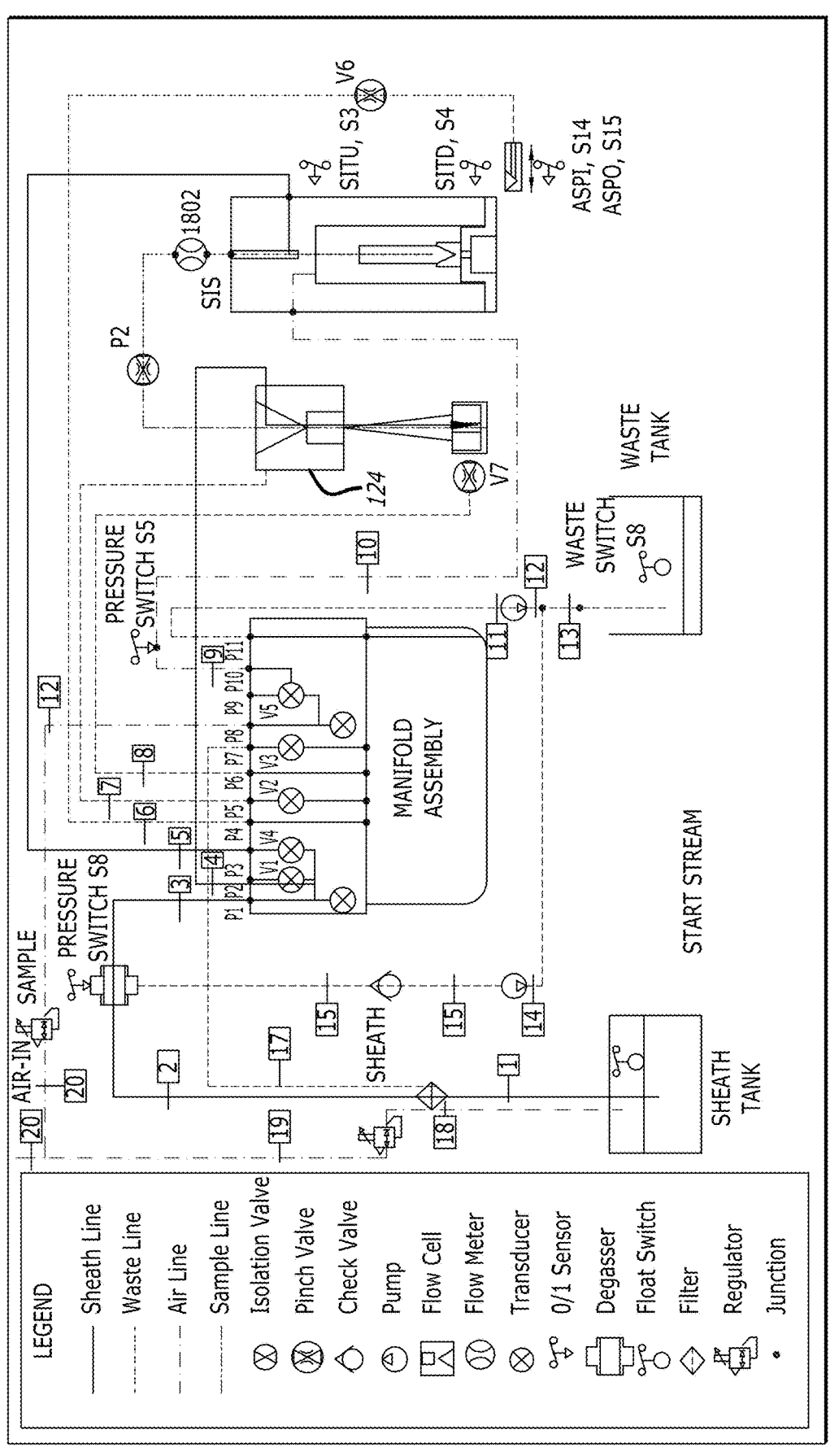
FIG. 18 is a schematic diagram of the fluidics system of the compact cell sorter system.

FIGS. 3A-3B illustrate various views of the fluidics bucket 120 which is a part of the fluidics system of the cell sorter system 100. FIG. 18 illustrates a schematic diagram of elements in the fluids bucket 120.

In FIG. 3B, the fluidic bucket 120 includes a sample regulator 301 and a sheath regulator 302 that control the fluidic pressure of the sample fluid and the sheath fluid, respectively. The fluidics bucket 120 further includes a degasser switch 304 and a degasser pump 305 to provide air pressure so that the degasser 306 can remove bubbles from the sheath fluid. Fluidics bucket further includes an aspirator pump 310 to externally aspirate waste out of the cell sorter system through the waste output port 334. The valve manifold 312 includes a plurality of valves to control the fluid system and a sample transducer 315 and a sheath transducer 316. The fluidics input output panel 104 includes a supply air input 331, sheath air output 332, a sheath fluid input 333, and a waste output 334. The sheath fluid 333 flows through a sheath filter 320 before entering the flow cytometer system 120. The fluids bucket includes a pressure switch that controls opening pressure of the Sample Pressure Chamber. The aspirator pump maintains the vacuum in the tank below the valve manifold 312.

Flow Cell Assembly

Figure 4A:
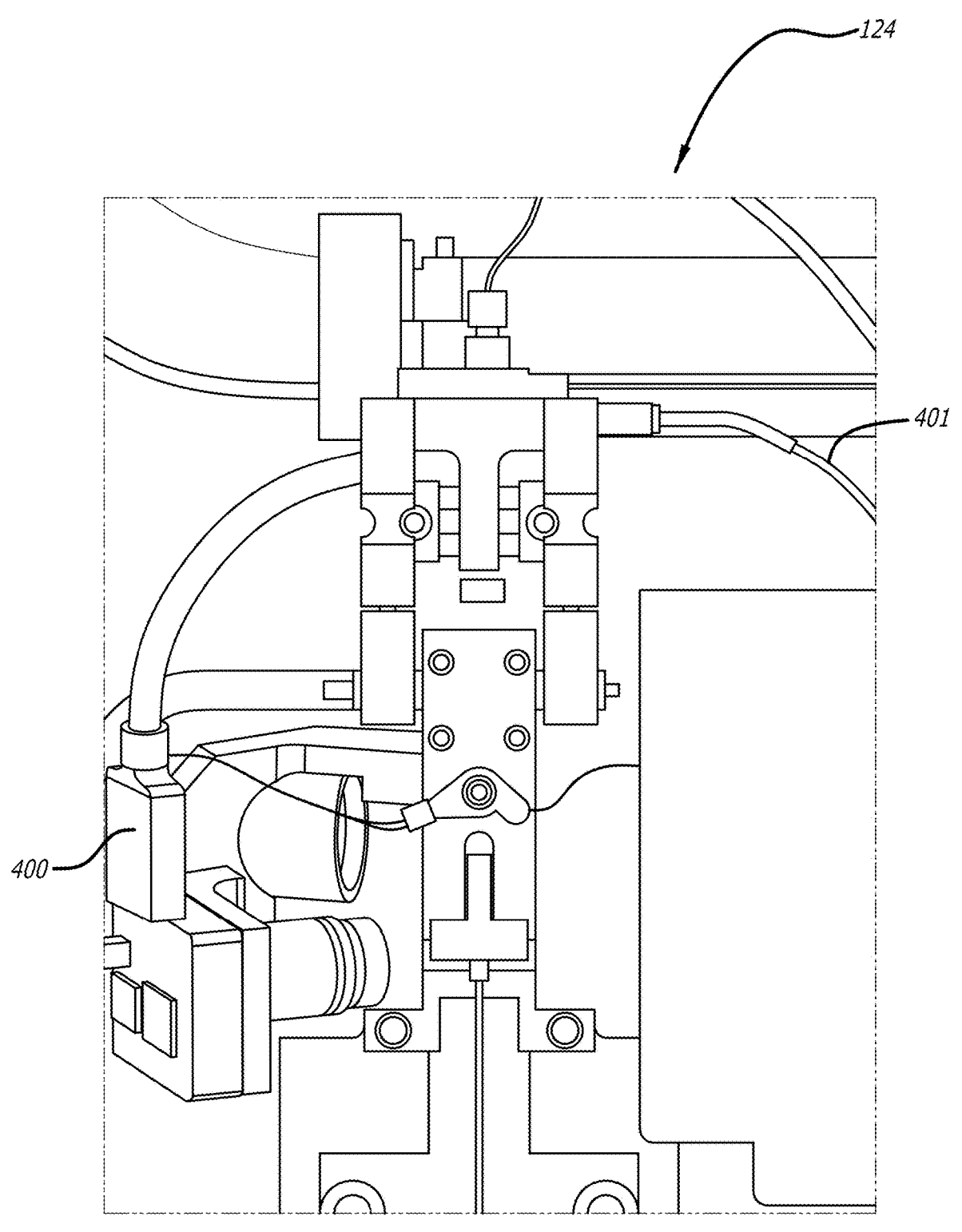
FIGS. 4A-4G are views of the flow cell in the fluidics system of the compact cell sorter system.

FIGS. 4A-4G illustrate various views and components of the flow cell assembly 124. In FIG. 4A the flow cell 124 has a ground connection 400 to a metal surface. This is to shield the sample fluid from charges being generated by the deflection unit and to remove charges that may have been already present.

Figure 4B:
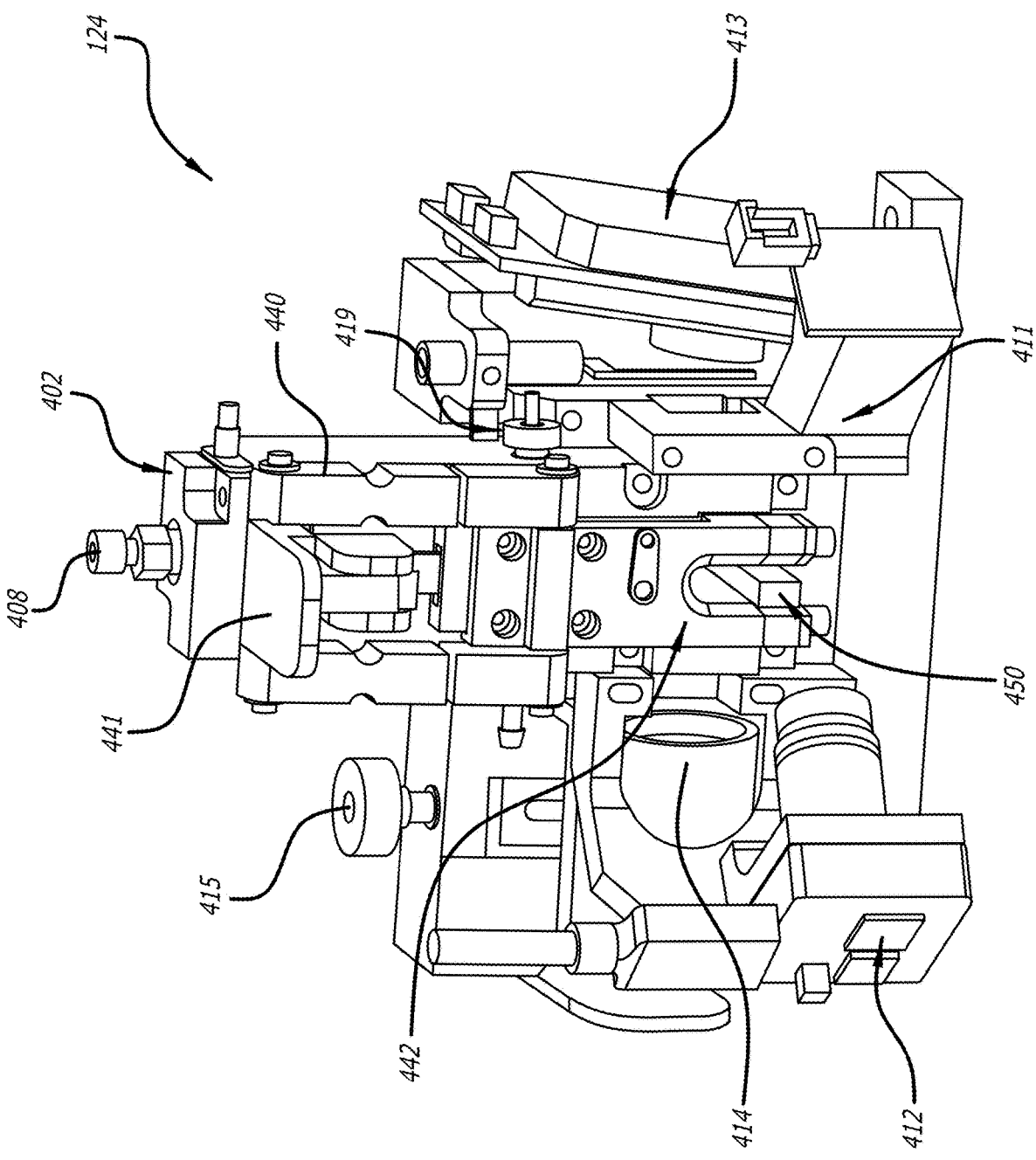

Referring now to FIG. 4B, the flow cell 124 includes a drop drive assembly 402, the nozzle assembly 450 and nozzle carriage assembly 442 a carriage release lever 441 of a flow cell linkage 440. The flow cell 124 has a number of optical components including a drop camera for 412, drop strobe assembly 411, forward scatter assembly 413, and a final focus lens 414. The final focus lens for 414 can be focused by a final focus adjustment 415. The drop drive assembly 402 has a sample input port 408 to receive a hose or pipe that carries the sample fluid.

Figure 4C:
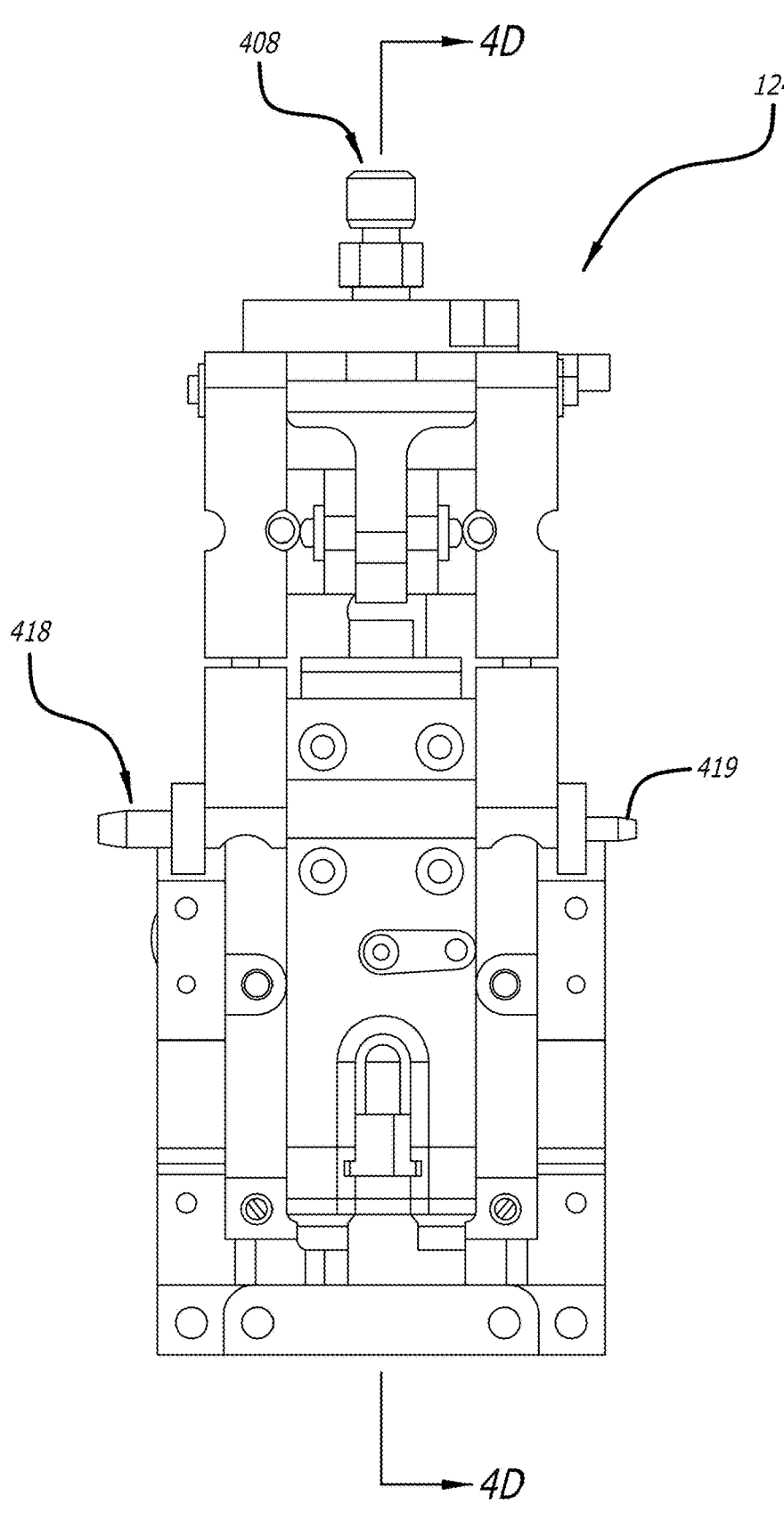

Referring now to FIG. 4C, the fluid ports for the flow cell 124 are shown. The flow cell 124 receives the sample fluid through a sample inlet port 408. The flow cell 124 receives the sheath fluid through a sheath input port 418. The flow cell 124 surrounds a stream of the sample fluid with sheath fluid. The flow cell 124 includes a conductive drain port fitting 419 threaded into the drain port (see right side port 1256 in FIG. 12C) of the flow cell body 404 to evacuate fluids from chambers inside the flow cell, and to impart charge onto the drops of sample fluid with a cell/particle. An electrical wire and a hose both couple to the conductive drain port fitting 419. The electrical wire is in communication with the sort controller to receive a signal that is synchronized with the drops. Over time the signal may be ground, one or more levels of positive charge voltages (e.g., +150, +300), or one or more levels of negative charge voltages (e.g., −150, −300) to respectively keep a drop uncharged, to positively charge a drop, or to negatively charge.

Figure 4D:
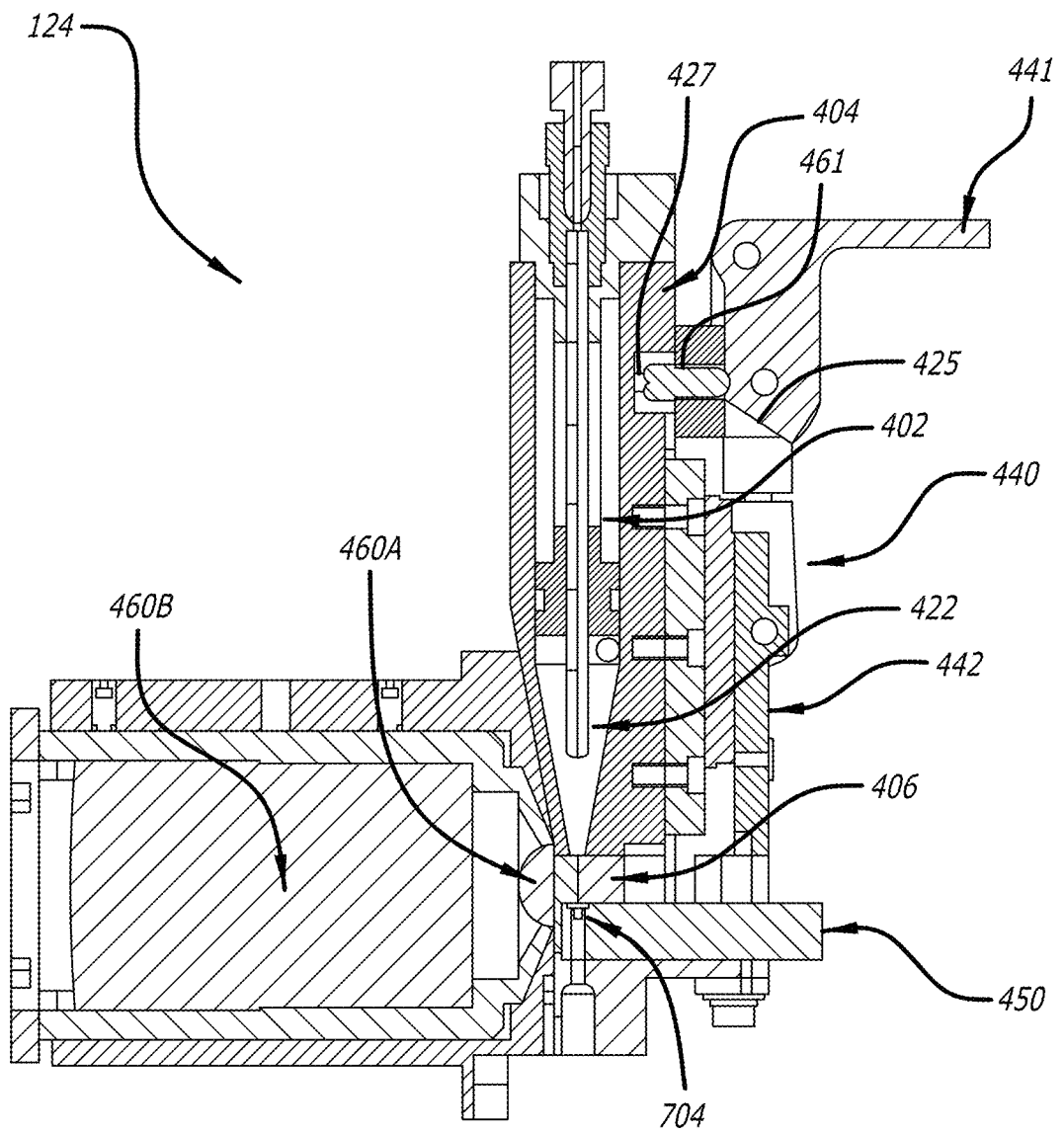

Referring now to FIG. 4D, a side cross-section of the flow cell 124 shown. the flow cell 124 includes a flow cell body 404, a drop drive assembly 402, a cuvette 406, a linkage assembly 440, a carriage assembly 442, and a nozzle assembly 450 with a nozzle 704. The linkage assembly 440 includes a carriage release lever 441 that pivots to move the nozzle assembly up and down with respect to the cuvette 406. The drop drive assembly 402 includes a sample injection tube 422.

Laser light from one or more lasers is sent into one or more interrogation regions in the flow channel of a cuvette to excite flowing cells/particles and/or one or more fluorescent dye markers attached thereto that pass by. The flow cell 124 further includes one or more objective lenses 460A-460B in order to capture light (e.g., reflected light, scattered light, fluorescent light) from the cells/particles and/or the one or more fluorescent dyes attached to the cells/particles on one side. On an opposite side, the one or more objective lenses 460A-460B can launch the captured light into a fiber optic cable.

Figure 4E:
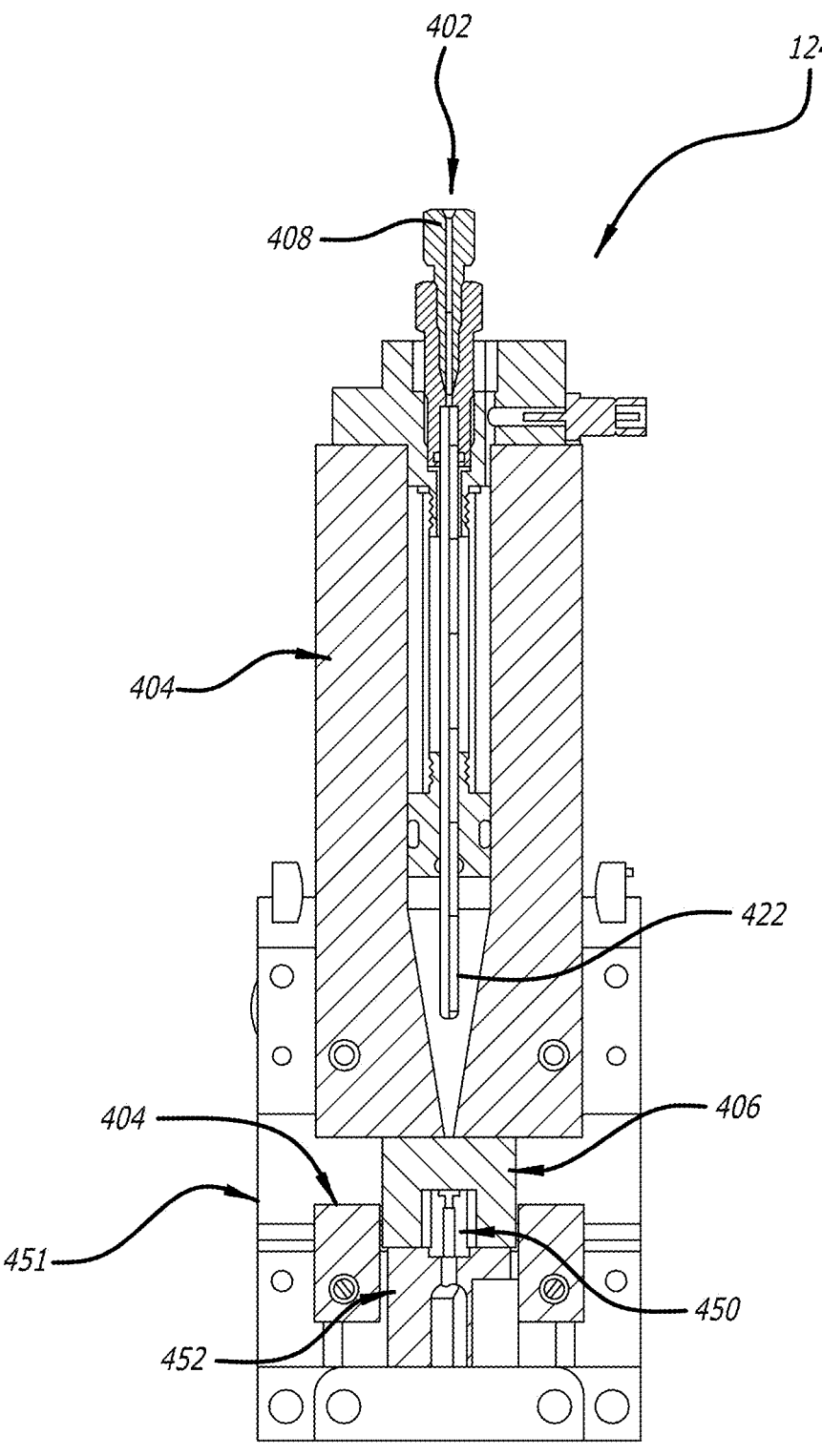

Referring now to FIG. 4E, a front cross-sectional view of the flow cell 124 is shown. The flow cell 124 includes a flow cell body 404 to receive the drop drive assembly 402. The nozzle assembly 450 is slid into a mount 452 that is coupled to the carriage assembly. The sample injection tube 422 is preferably formed of glass to avoid surface etching in the presence of electrical currents in the sheath fluid for drop charging and vibration of the drop-drive for drop separation that can cause leakage. The drop drive assembly 402 includes a sample inlet 408 to receive the sample fluid.

Figure 4F:
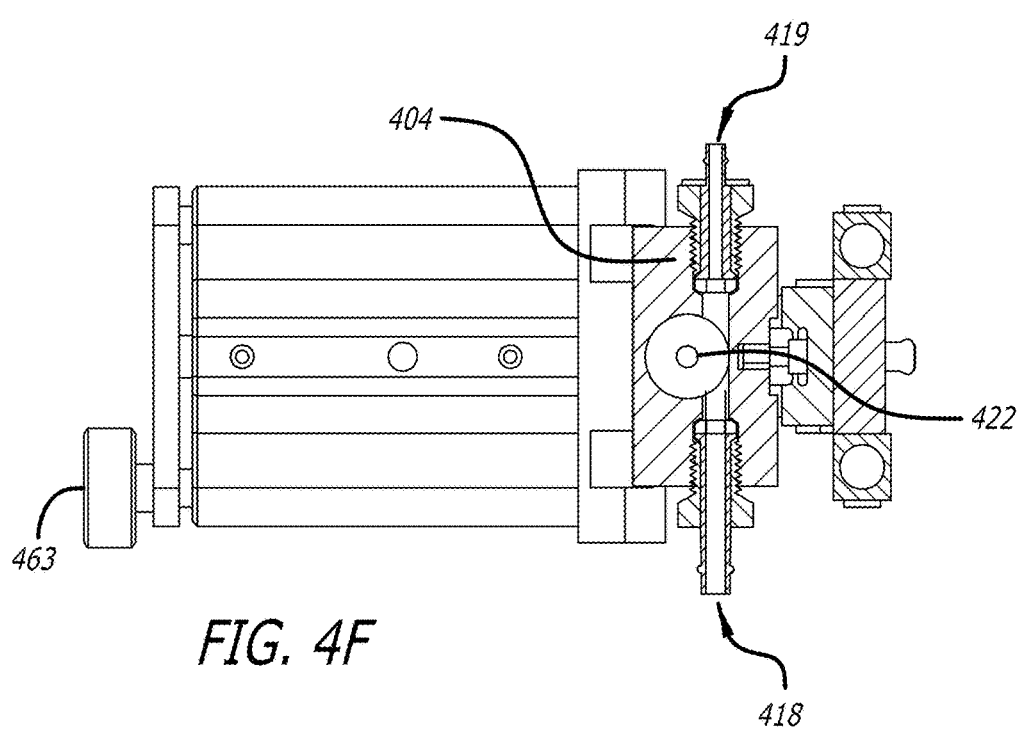

Referring now to FIG. 4F, a cross-sectional view of the flow cell 124 is shown cut through the drain port/charging port with the conductive hose fitting 419 and the sheath inlet port with its hose fitting 418. The sample injection tube 422 is centered in a chamber within the flow cell body 404. The flow cell 124 includes a rear focus adjustment 463 for the one or more objective lenses.

Figure 4G:
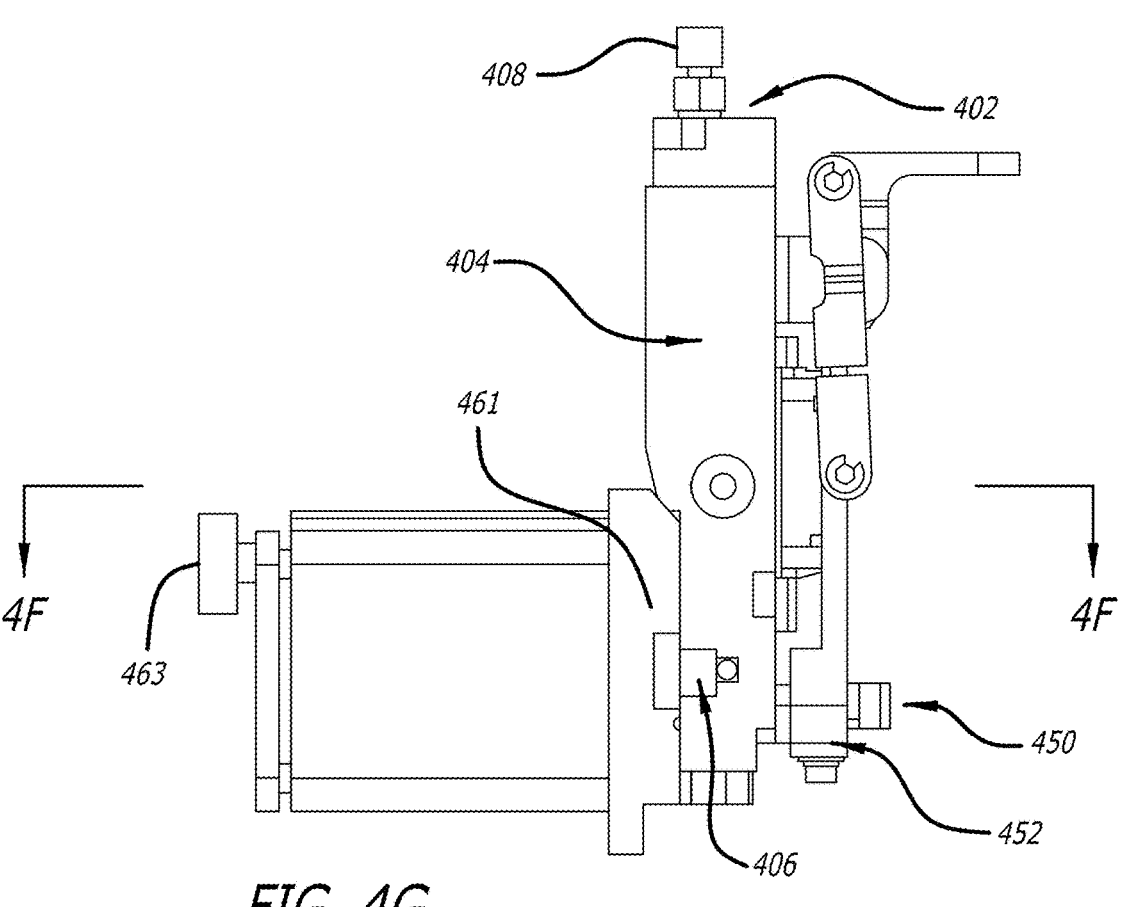

FIG. 4G illustrates a side view of the flow cell 124. The center optical axes of the objective lenses 460A-460B are shown lined up to receive light only from the cuvette. The objective lens mount 461 assures that the objective lenses 460A-460B remain in alignment. The flow cell body 404 is opaque so that light from other sources, such as ambient, is not captured by the objective lenses for 460A-460B.

The nozzle assembly 450 slides in and out of the mount 452 in order to service or repair components of the nozzle assembly or swap for a different diameter of opening in the nozzle. The nozzle of the nozzle assembly receives a sample flow of fluid from a cuvette and forms drops with preferably a single cell/particle each for sorting out.

Flow Cell Linkage and Nozzle Carriage

FIGS. 4H-4L illustrate various views and components of the flow cell linkage 440 and nozzle carriage assembly 442 for the flow cell assembly 124 of the cell sorter system 100. FIGS. 5A-5B and 6A-6B respectively illustrate side views and cross section views of the flow cell assembly 124 to show operation of the flow cell linkage 440 and nozzle carriage assembly 442.

Figure 4H:
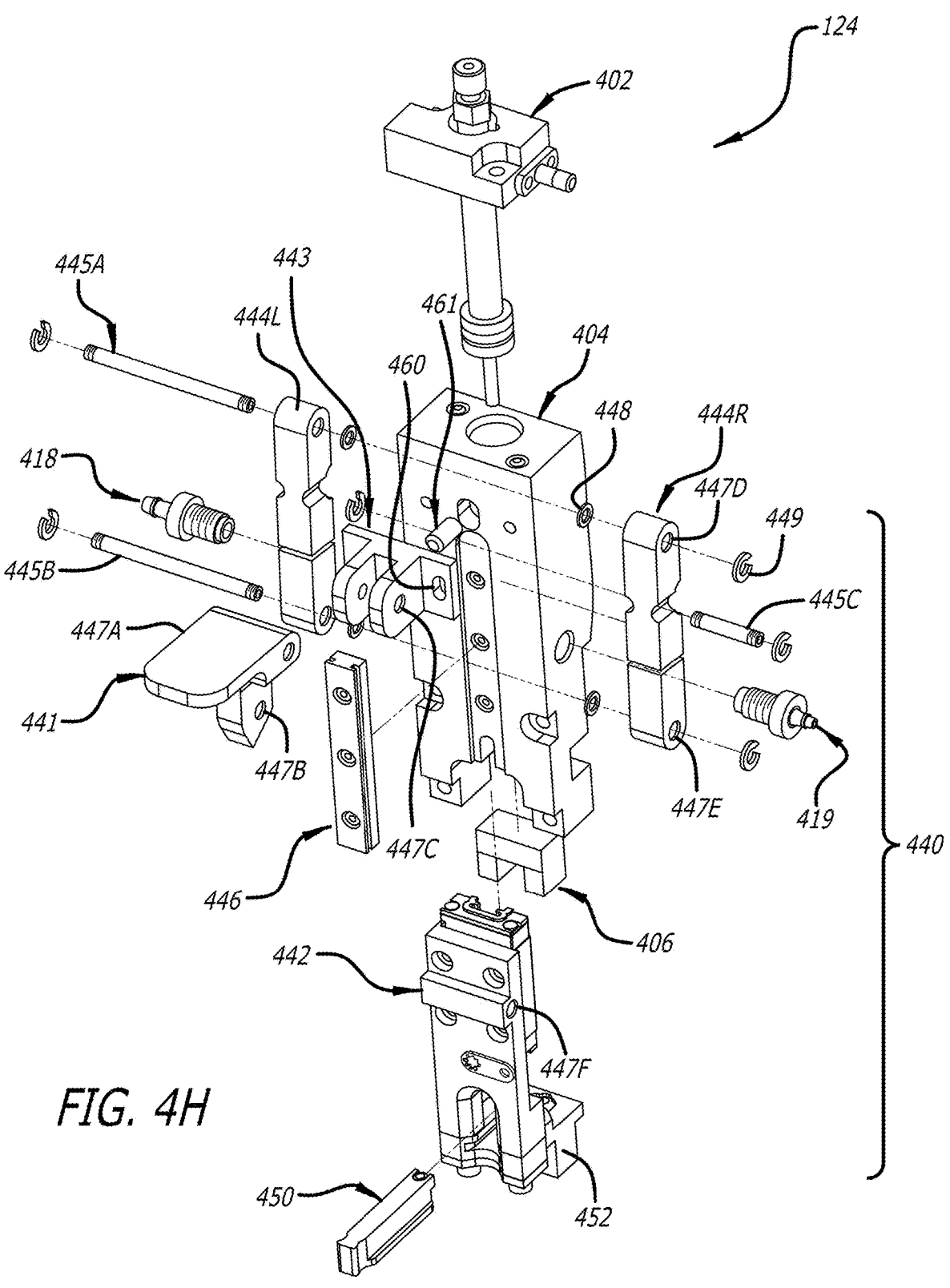
FIG. 4H is an exploded view of the flow cell of the compact cell sorter system.
Figure 4I:
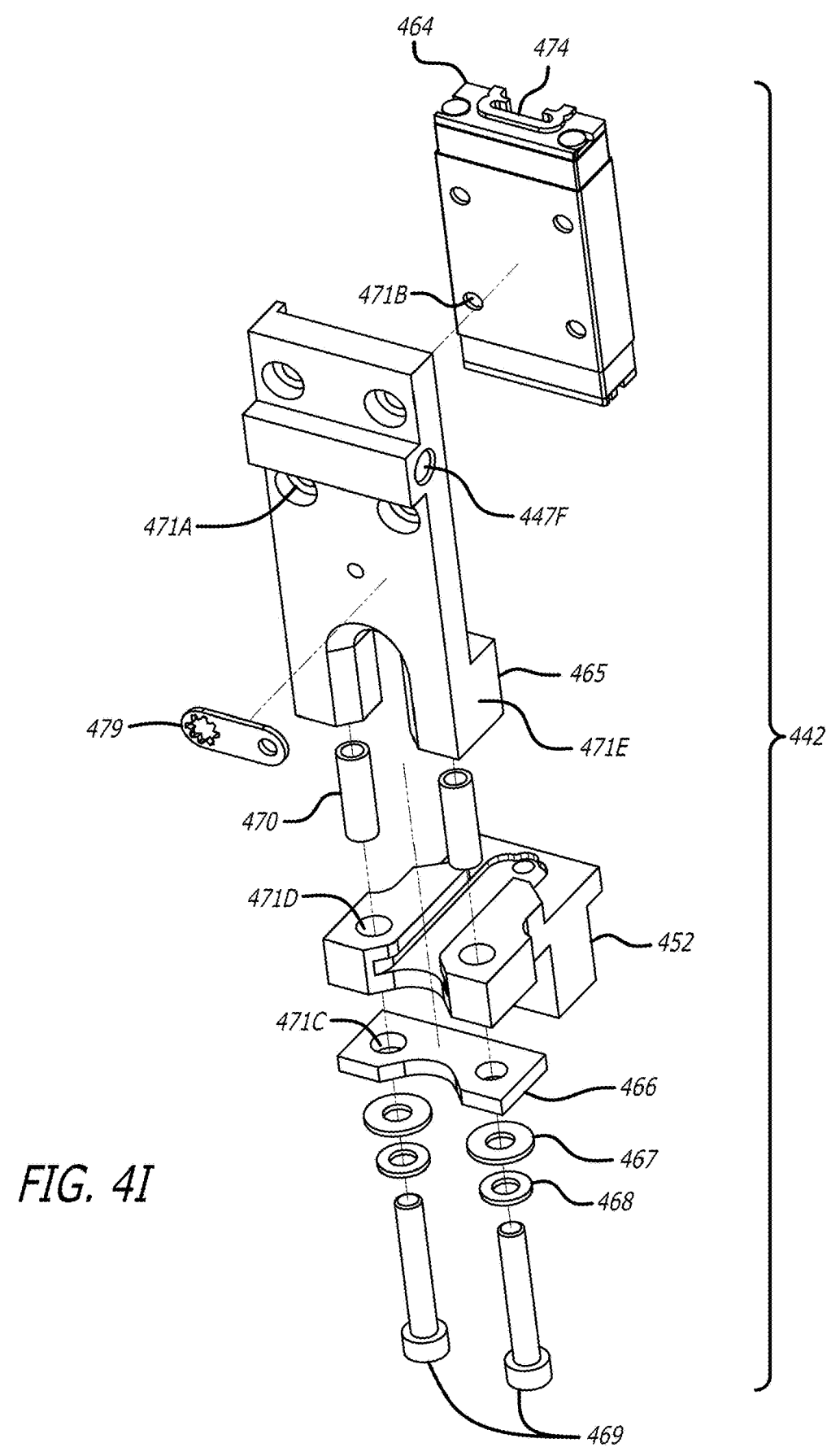
FIG. 4I is an exploded view of the nozzle carriage assembly of the flow cell shown in FIG. 4H.

Referring now to FIG. 4H an exploded view of the flow cell 124 is shown. The flow cell 124 includes flow cell linkage 440 and the nozzle carriage assembly 442. The nozzle assembly 450 slides into and out of the mount 452. an exploded view of the nozzle carriage assembly 442 is shown in FIG. 4I.

The flow cell linkage 440 includes a carriage lever 441, left and right spring-loaded lever arms 444L-444R, nozzle carriage assembly 442 pivotally coupled together at pivot points by pivotal shafts 445A-445C. Each of the pivotal shafts 445A-445C can include washers along the shaft between the lever arms and the pivotal openings 447A,

447C, and 447F. Each of the pivotal shafts 445A-445C is retained within the pivotal openings by a circlip (retention fastener) 449.

The carriage lever 441 is pivotally mounted to a pair of pivot point openings 447C in arms of a leverage hinge bracket 443 by shaft 445C at a pivot point opening 447B in a protrusion extending from the lever.

A top pivot point opening 447D in each of the left and right lever 444L-444R arms is pivotally coupled to the lever 441 at a pivot point opening 447A by the shaft 445A. A lower pivot point opening 447E in each of the left and right lever arms 444L-444R is pivotally coupled to the nozzle carriage assembly 442 at pivot point opening 447F by the pivotal shaft 445B. The nozzle carriage assembly 442 is slidingly coupled to a linear slide rail 446 that is mounted to the flow cell body 404 by one or more fasteners (e.g., threaded screws or bolts).

In operation, the carriage lever 441 pivots about pivot point opening 447B thereby lifting up or letting down at the top of the lever arms 444L-444R through the shaft 445A at pivot point openings 447A,447D. This translates through the lever arms into linear motion at the bottom pivot point openings 447E. By the shaft 445B through the bottom pivot openings 447E in the lever arms 444L-444R and the pivot opening 447F in the nozzle carriage assembly 442, the liner motion in the lever arms is translated into a linear motion in the carriage assembly 442. With a nozzle assembly 450 slid into the mount 452, the carriage assembly 442 can lift up and lower down the nozzle assembly to engage and disengage with the cuvette 406.

The lever arms 444L-444R are spring-loaded between an upper portion and a lower portion to be sure a proper force is exerted upward on the nozzle assembly 450. This assures that an O-ring is squeezed to properly seal up against a surface the cuvette 406.

The flow cell linkage 440 is adjustable upward and downward by the hinge bracket 443. The hinge bracket 443 has a pair of elongated openings 460 in opposite sides of the flanges that mount to the flow cell 404. A pair of screws or bolts (not shown) are inserted through the elongated openings 460 through the elongated openings 460 and into threaded openings in the flow cell 404. The elongated openings 460 allow the bracket 443 to shift up or down around the pair of screws or bolts when loosened. The movement of the bracket 443 adjusts the entire flow cell linkage 440, including the carriage assembly 442, up or down.

The flow cell linkage 440 further includes a spring loaded lever detent 461 with one end inserted into an opening in the flow cell 404 that can couple against a spring 427 (see FIG. 4D). As shown in FIG. 4D, an opposite end of the lever detent 461 rides up against a backside cam 425 in the lever hinge 441 to maintain the flow cell linkage 440 in either of an upward position or a downward position.

Referring now to FIG. 4I, an exploded view of the nozzle carriage assembly 442 is shown. The nozzle carriage assembly 442 includes a carriage plate 465, a linear bearing 464, the nozzle mount 452, a clamping plate 466, flat washers 467, lock washers 468, threaded bolts 469, and alignment tubes 470 assembled together. The threaded bolts 469 are inserted through the lock washers 468, the flat washers 467, through holes 471C in the clamping plate 466, holes 471D in the nozzle mount 452, and inner hollow cylinders of the alignment tubes 470. The threads of the bolts 469 are screwed or threaded into threaded holes 471E in the base of the carriage plate 465 to hold the mount 452 coupled to the plate. Fasteners, such as metal screws, are inserted through a plurality of through holes 471A in the front of the carriage plate 465 and screwed into threaded holes 471B in the linear bearing 464 to couple the plate and bearing together.

The linear bearing 464 includes a pair of guide rails 474 in a backside to slide along the linear slide rail 446 shown in FIG. 4H. The front side of the carriage plate 465 includes the pivotal opening 447F to receive the shaft 445B. A rectangular shaped portion of the carriage plate extends out from the front face of the plate to form the pivotal opening 447F.

To electrically ground the carriage assembly 442, a ground wire lug 479 coupled to a ground wire is mounted by a fastener to near a front center portion of the carriage plate 465.

Referring now to FIGS. 4J through 4M, various views of the lever arm 444L-444R are shown. Each of the lever arms 444L-444R can include at least one small side cutout to allow the lever arms to pass by the ends of the shaft 445C. Each of the lever arms can also include a back side cutout adjacent the side cutout.

Figures 4J, 4K, 4L, 4M:
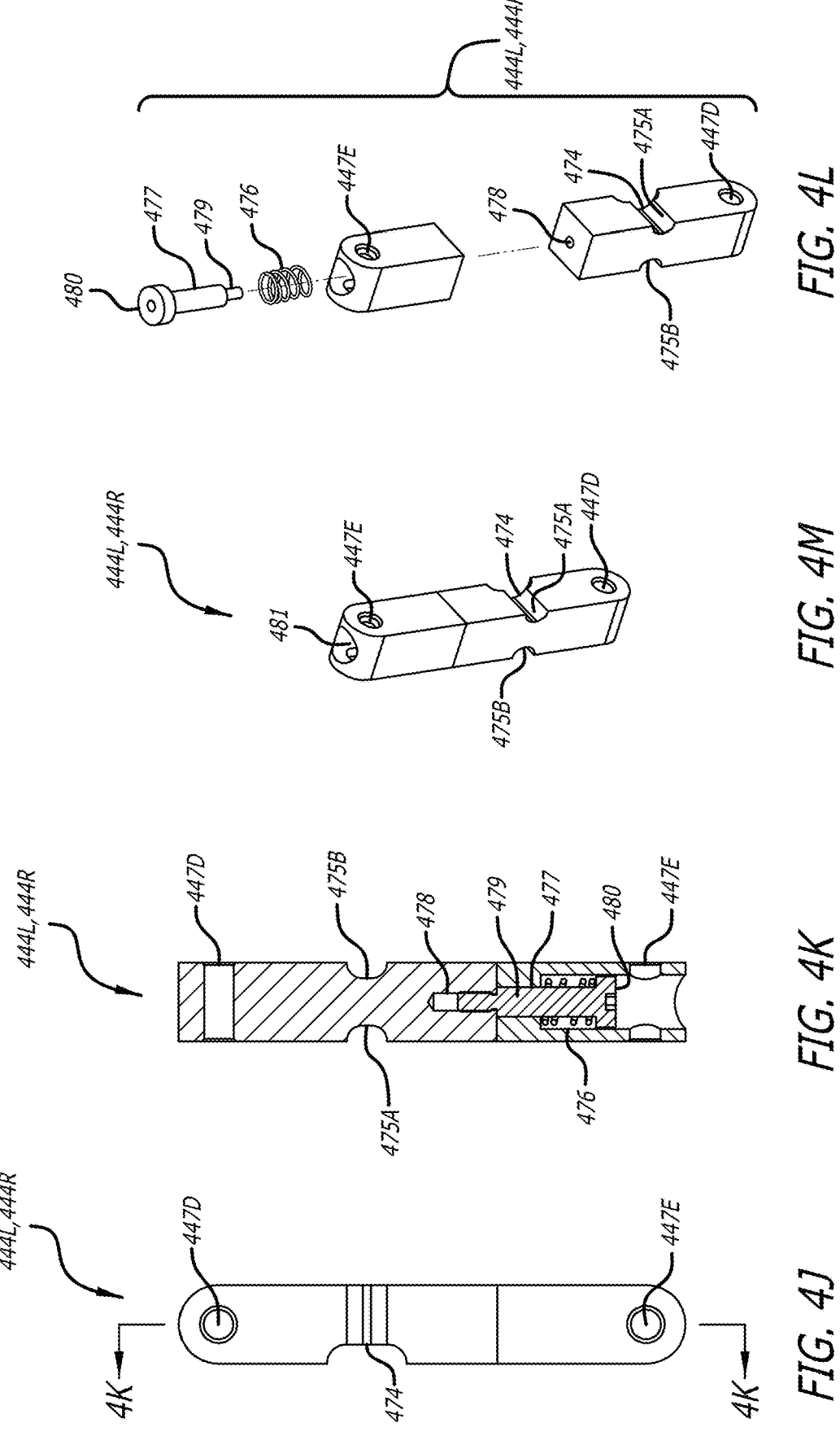
FIGS. 4J-4M illustrate various views of an instance of a left and right spring-loaded lever arm for the carriage linkage.

FIG. 4J illustrates the back notch 474 in each of the lever arms 444L-444R. The back notch provides clearance for the bracket 443 mounting screw heads.

FIG. 4K illustrates the spring-loaded assembly of each lever arm. FIG. 4K further illustrates the through holes 447D-447E. A bolt 480 holds the spring 476 and the upper and lower portions of each lever arm spring loaded together. The bolt 480 includes a shaft 477 with a smaller threaded portion 479 screwed into a threaded opening 478 in the upper portion up until the larger shaft buts up against a lower surface of the upper portion.

As shown in FIG. 4L, the shaft of the bolt 480 is inserted into and through the spring into the opening 481 in an end of the lower portion. The bolt 480 can have a hex head, a socket head, a screw head or otherwise a type of head rotatable by a tool inserted into the opening 481 in the end to reach the head deep in the opening.

The spring 476 presses up against the head of the bolt 480 at one end and presses against the bottom of the opening 481 in the lower portion at the opposite end. Accordingly, the lower portion and the upper portion of the lever arm can be slightly pulled apart and placed in tension up until the spring is fully compressed. The spring provides tension against the cam to help hold a position of the carriage release lever 441 and the carriage assembly.

Figures 5A, 5B:
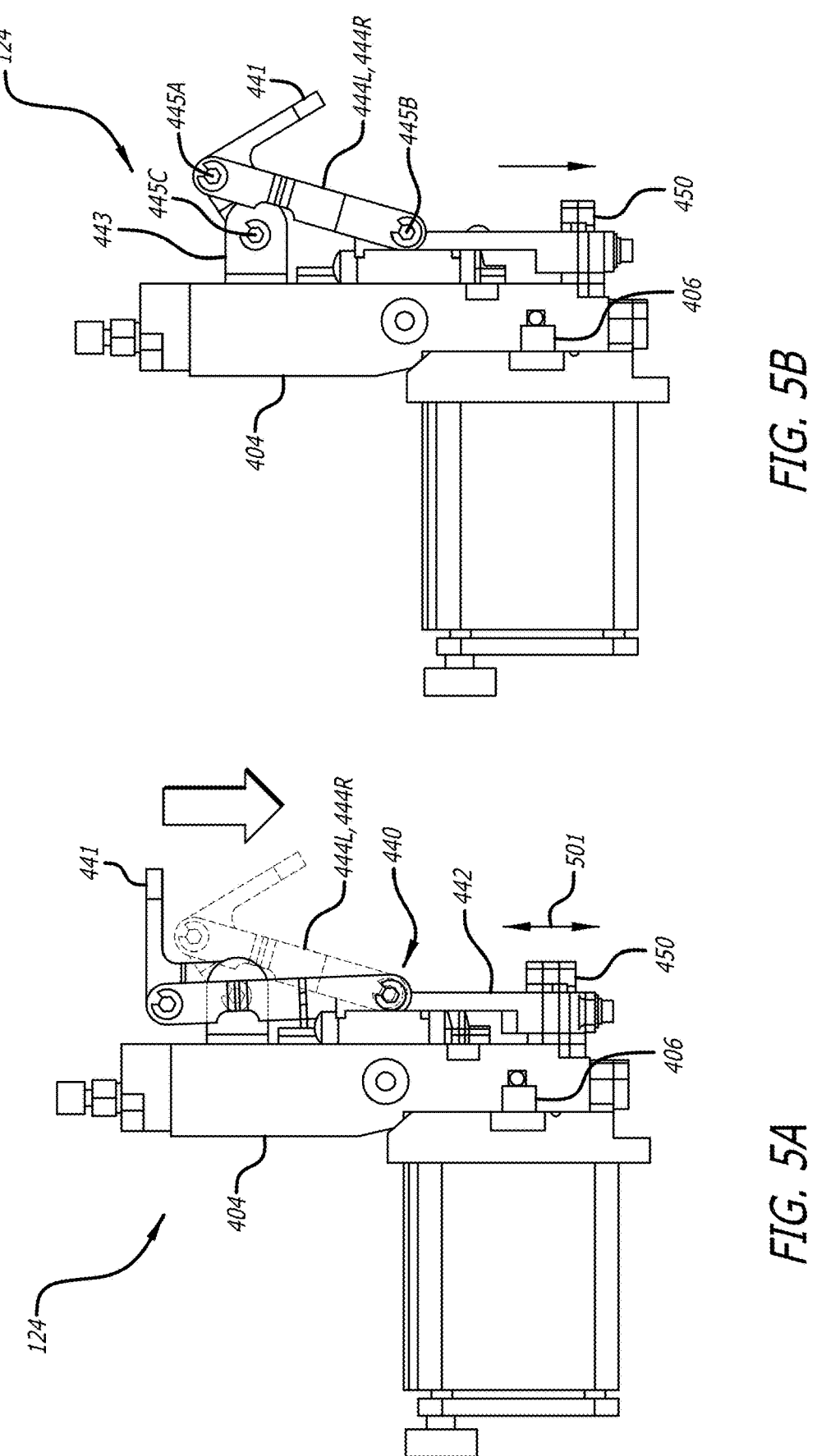
FIGS. 5A-5B are side views illustrating carriage movement of the flow cell as the lever is raised and lowered, respectively.

Referring now to FIGS. 5A-5B, the motion in the flow cell linkage 440 is shown under control of the carriage release lever 441. In the upward position of the release lever 441, the nozzle carriage assembly 442 is in its highest position so that the nozzle assembly 450 engages the cuvette 406. In this highest position, the lever arms 444L-444R are in a substantially vertical position. The cam in the release lever 441 is held in the upright position by friction from the detente. Pressing down on the release lever 441 causes the lever arms 444L-444R to pivot in parallel together away from the flow cell body 404 and allows the nozzle carriage assembly 442 to slide down in the guide rails. This lowering of the nozzle carriage assembly 442 disengages the nozzle assembly 450 from the cuvette 406.

As can be seen in FIG. 5B, the carriage release lever 441 pivots around the shaft 445C in the lever hinge/bracket 443. A lower end of the lever arms 444L-444R pivot around the shaft 445B in the carriage plate of the carriage assembly 442. An upper end of the lever arms pivot about shaft 445A in the release lever 441. The L shape of the release lever 441 pushes the lever arms 444L-444R out and slightly downward with respect to the flow cell body 404.

Figures 6A, 6B:
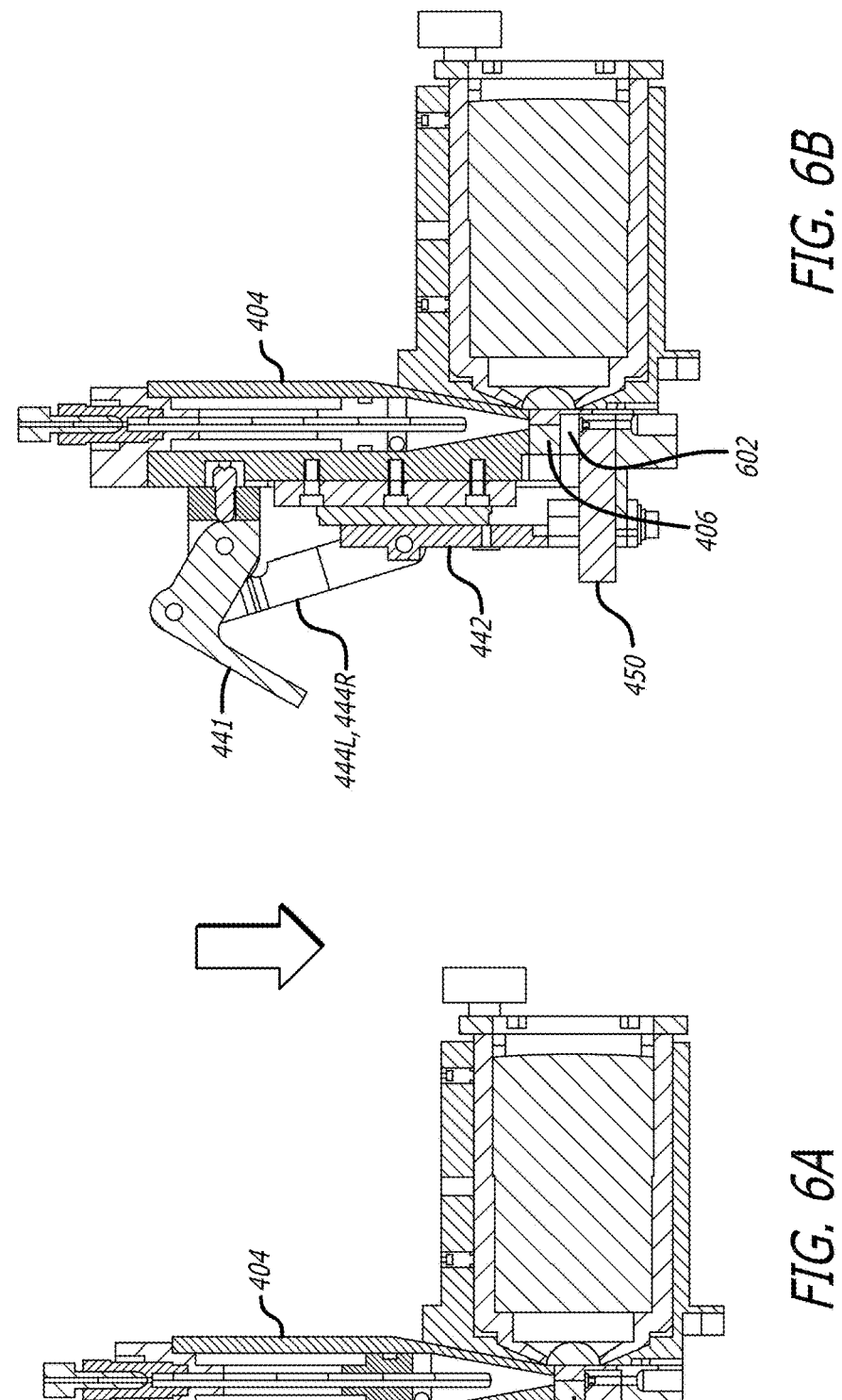
FIGS. 6A-6B are cross-sectional views illustrating carriage movement of the flow cell as the lever is raised and lowered, respectively.

FIGS. 6A-6B better show the disengagement of the nozzle assembly from the cuvette 406. In FIG. 6A, the release lever 441 is in its upward position. The lever arms 444L-444R (see FIG. 5A) are in their upward vertical position. The nozzle assembly 450 is in an upward position engaging the cuvette 406. The O-ring seal of the nozzle assembly 450 is pressed up against the cuvette 406 to seal around the nozzle.

In FIG. 6B, the release lever 441 is in its lower position, the lever arms are pivot away from the flow cell body 404 and the carriage assembly is in a lower position along with the nozzle assembly 450. Accordingly, the nozzle assembly 450 is disengaged from the cuvette 406. A gap 602 is shown between the nozzle assembly 450 and the cuvette 406. In this lowered position, the nozzle assembly 450 can be slid out and away from the mount 452 of the carriage assembly 442.

Nozzle Assembly

Figure 7A:
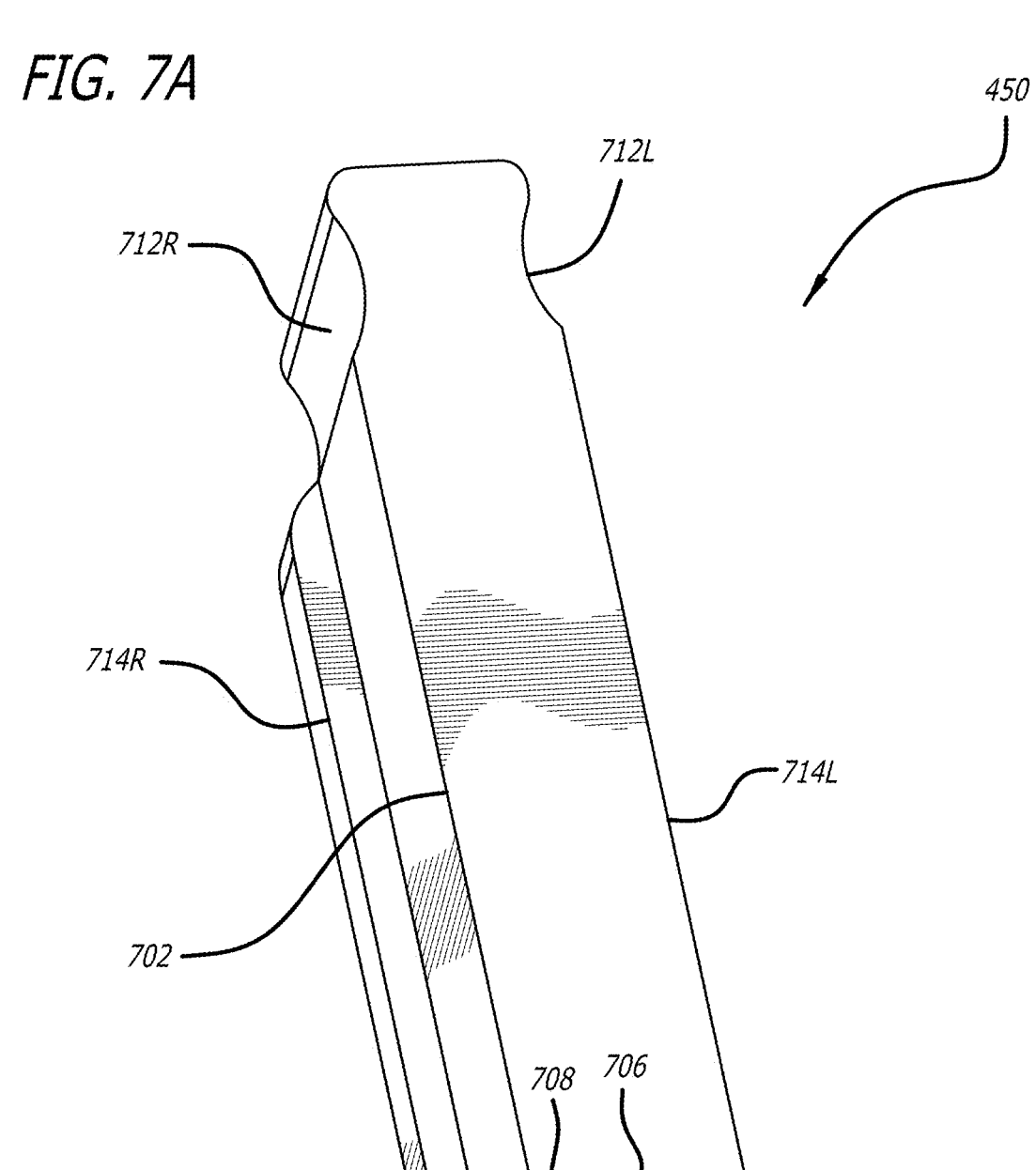
FIG. 7A is a perspective view of the nozzle assembly in the flow cell of the compact cell sorter system.
Figures 7B, 7C, 7D:
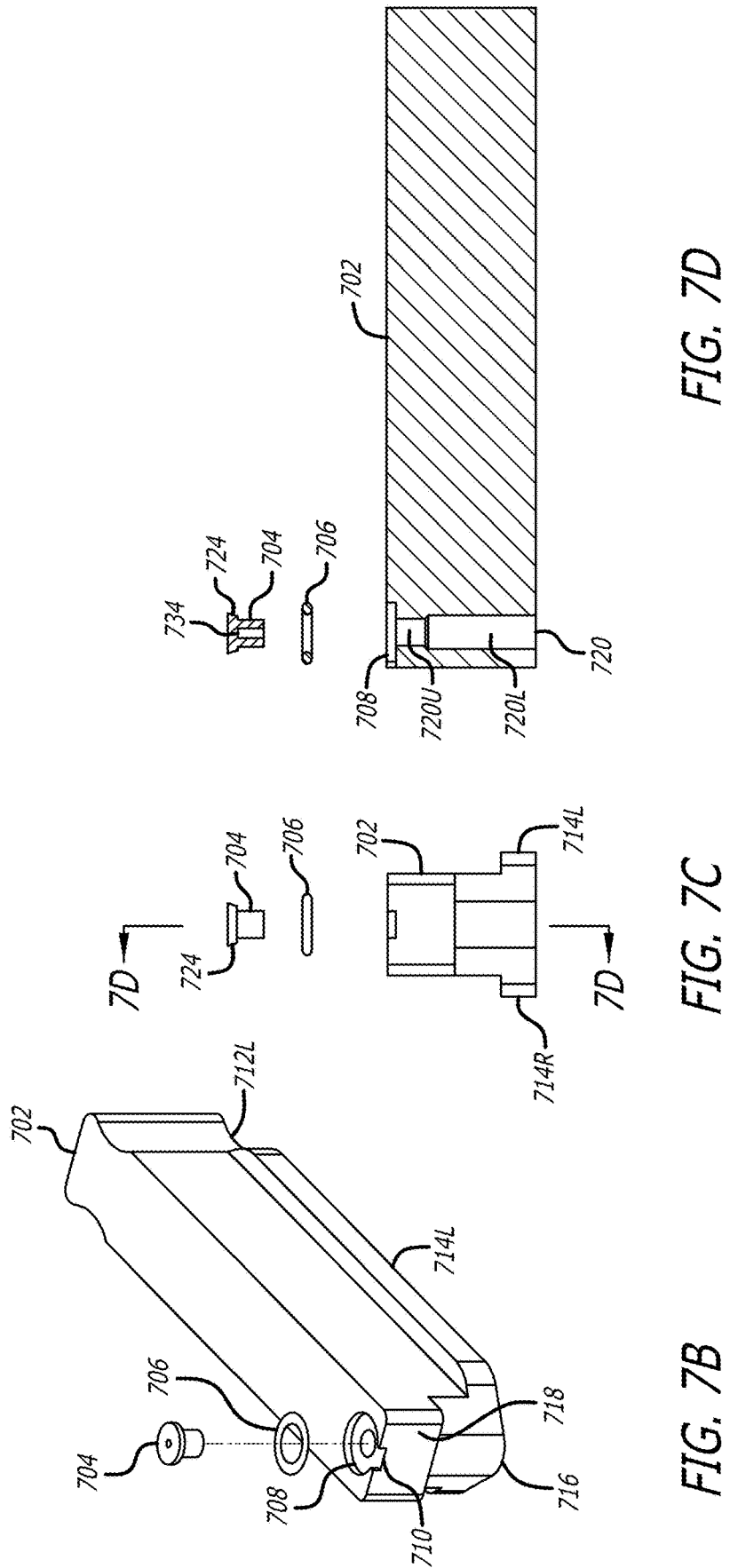
FIGS. 7B-7D are exploded views of the nozzle assembly in the flow cell of the compact cell sorter system.

Referring now to FIGS. 7A-7F, various views of the nozzle assembly 450 are illustrated. FIGS. 7B-7D illustrate various exploded views of the nozzle assembly 450. FIGS. 7A and 7E-7F illustrate various assembled views of the nozzle assembly 450.

The nozzle assembly 450 includes a three dimensional body 702, a ceramic nozzle 704, a replaceable O-ring 706, and a partial gland opening 708. The partial gland opening 708 is washer shaped opening that includes a slot 710 at a back end for easy O-ring removal by finger nail or a small tool. Despite having the slot 710, the O-ring 706 in the partial gland opening 708 can still provide a seal around the nozzle 704 capable of withstanding high pressures when pressed against a cuvette. The cross-section of the three-dimensional body 702 generally has a top portion, a mid-section portion under the top portion, and a base portion under the top and midsection portions. The three-dimensional body 702 further includes a left rail 714L and a right rail 714R along left and right sides in the base portion.

The three-dimensional body 702 is elongated and provides a handle at a front end by a left indentation 712L and a right indentation 712R in top, midsection, and bottom portions. At a back end opposite the front end, the three-dimensional body 702 provides a nose or arch-shaped stop 716 in the base portion to make two points of contact. The nose or arch-shaped stop 716 extends up from the base through the midsection up to the top portion of the body. The end 718 of the top portion extends slightly out over the nose or arch-shaped stop 716 to be sure the O-ring has sufficient support in the partial gland to seal up against the cuvette. Because it provides a handle, the three-dimensional body 702 may be referred to herein as the nozzle handle 702.

As shown in FIG. 7D, the three-dimensional body 702 includes a through hole 720 starting at the base of the partial gland 708 with an upper receptacle portion 720U to receive the nozzle 704 and a lower drop channel portion 720L to allow drops to flow through without interference from the sidewalls.

The three-dimensional body 702 is formed of a high performance engineered thermoplastic polymer, such as polyether-ether-keytone (PEEK) in the polyaryletherketone (PAEK) family, to provide mechanical strength and high temperature and chemical resistance. The three-dimensional body 702 is generally formed with low tolerances. The low tolerances allow the nozzle assembly to readily slide in and out of guides in a mount. The low tolerances also provide a somewhat sloppy friction fit to the mount and allow a slight pivotal motion to clear debris from two stop points at the arch shaped stop 716. Other thermoplastic polymers may be used to form the three-dimensional body 702 at low cost and low tolerances.

The size (e.g., diameters, depth) and shape of the gland and the nozzle, allow a low cost standard rubber O-ring to be used as the replaceable O-ring 706. The O-ring may be formed of ethylene propylene diene monomer (EPDM), a synthetic rubber, having good resistance to various environmental factors. In alternate embodiments, the O-ring can be formed of silicon rubber or natural rubber.

The nozzle 704 is preferably a ceramic nozzle formed of a ceramic material given its insulative electrical properties to avoid grounding of the charges being transferred to the drops of sample fluid before reaching the deflection unit. As shown in FIGS. 7C-7F, the top of the nozzle 704 has a beveled ring 724 to properly receive and hold the circular cross section of the O-ring in the depth of the partial gland. The top of the nozzle 704 has a drop inlet 734 that leads to a somewhat larger diameter drop channel 735 in the nozzle. When the nozzle 704 is friction fitted into the receptacle 720U of the body 702, the nozzle channel 735 of the nozzle 704 is in communication with a somewhat larger diameter drop channel 720L of the through hole 720 extending the width of the body 702.

FIGS. 7E and 7F illustrate how the nozzle 704 and O-ring 706 are assembled into through hole and partial gland opening in the body 702 of the nozzle assembly. The O-ring 706 is held in the partial gland opening 708 by the beveled ring 724 in the top portion of the nozzle 704.

The nozzle assembly 450 is selectively slidingly coupled into and decoupled from the nozzle mount 452. The tolerances between the nozzle body of the nozzle assembly 450 and the nozzle mount 452 is about 0.25 microns or more for a lose fit. It is not a tight fit. This allows the nozzle assembly 450 to pivot somewhat about an axis through the orifice of the nozzle. The lose fit facilitates clearing of debris between the nose and the receiver of the nozzle mount for a proper registration of the nozzle orifice with the fluid flow channel in the cuvette 406.

The cuvette 406 can be formed of one or more pieces of optical grade quartz to receive laser light and allow reflected light, scattered light, fluorescent light to be captured.

The sample droplets can become charged by the conductive host fitting mounted in a drain/charge port of the flow cell. Accordingly, the nozzle assembly must be formed of non-conductive or insulative materials to avoid charge loss through a ground path to the carriage assembly. The nozzle mount 452 and the nozzle carriage assembly 442 are electrically grounded to shield the charged droplets from the charges on deflection plates below the nozzle mount.

FIGS. 8A-8B, 9A-9B, 10A-10B, and 11A-11B illustrate views of sliding the nozzle assembly 450 into and out of the nozzle mount 452 of the carriage assembly 442 in the flow cell 124. This allows for maintenance of the nozzle assembly 450, including replacement of its O-ring seal.

Assume the nozzle assembly 450 is pushed into the slot 910 in the mount 452. Initially, as better shown in FIGS. 9A-9B, bottom rails 714L-714R of the nozzle assembly 450 are lined up and respectively inserted into guide rail openings 914L-914R in the mount 452. The nozzle assembly 450 is pushed into the mount within the slot 910 as far as possible so that the nose stop 716 of the body 702 engages the end wall of the mount in the slot 910.

In operation of the cell sorter (sorting flow cytometer), a stream of sample drops with marked cells/particles flow from the SIT into the flow cell body and then into the flow channel 906 of the cuvette 406 for analysis by lasers and detectors. If the nozzle assembly 450 is properly aligned in the mount 452, such as shown by axis 1000 in FIG. 10B, the stream of drops from the flow channel in the cuvette 406 are received by the opening in nozzle of the nozzle assembly. The mount 452 has an opening 916 in the slot 910 that allows a stream of drops received from the opening in the nozzle of the nozzle assembly 450 to pass through. Accordingly, it is desirable to achieve proper alignment of the nozzle assembly 450 in the mount 452.

In FIG. 11A, the nozzle assembly 450 is ready to be inserted into the slot 910 of the mount 452. The mount 452 includes a pair of nubs 1101-1102 formed in the end wall of the slot 910. The nozzle assembly 450 is pushed into the slot 910 as far as possible so that the nose stop 716 of the body 702 engages the nubs 1101-1102.

In FIGS. 11B-11C, the nozzle assembly 450 is fully inserted into the slot 910 of the mount 452. The opening in nozzle of the nozzle assembly 450 is lined up with the flow channel in the cuvette 406 along the axis 1100. Preferably, the opening in the nozzle of the nozzle assembly is concentric with the opening 906 in the mount 452 along the axis 1100. However, debris can come between the nozzle assembly and the mount so that center of the opening in the nozzle is offset from center of the opening 906 in the mount. Because the center of the flow channel in the cuvette is aligned with the center of the opening in the mount, the center of the flow channel can also be offset from the center of the opening of the nozzle in the nozzle assembly by the debris. Addressing the debris and misalignment of centers of the holes is desirable.

Figure 11E:
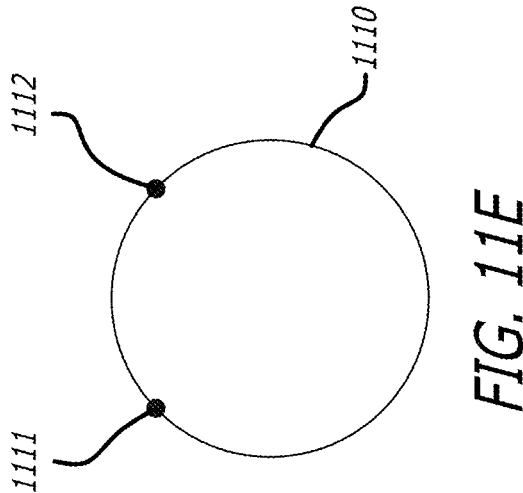
FIG. 11E is a circle with two dots illustrating points of contact of the end of the nozzle assembly registered with the nozzle mount of the flow cell.
Figure 11D:
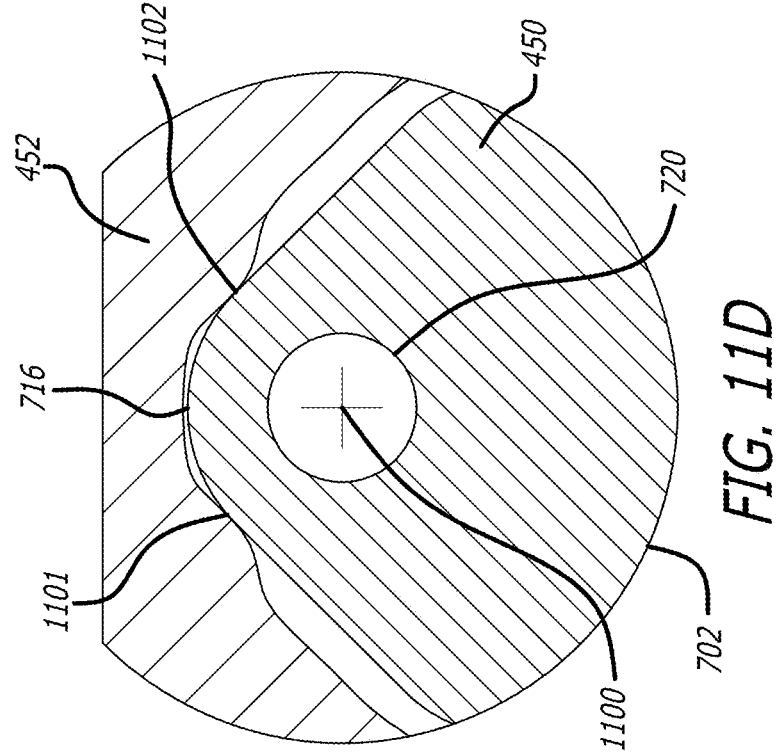
FIG. 11D is a magnified cross-sectional view of the end of the nozzle assembly registered with the nozzle mount of the flow cell.

FIG. 11D illustrates a magnified cross-sectional view of the nose stop 716 of the body 402 of the nozzle assembly 450 engaged with the mount 452. The nozzle of the nozzle assembly 450 is to line up with the flow channel in the cuvette 406 along the axis 1100. The nose stop 716 in the body 702 of the nozzle assembly 450 butts up against nubs 1101-1102 in the mount 452 making two points of contact. Occasionally debris may come in between the two points of contact. The design of the nose stop 716 and the nubs in the mount 452 allows for the debris to be cleared. The left and right finger grabs 712L-712R invite a user to slightly pivot the nozzle assembly 450 about the axis 1100 as it is pushed into the slot 910 to help clear any debris.

FIG. 11E schematically illustrates the two point contact 1111-1112 between the nose stop 716 of the body 702 of the nozzle assembly 450 and nubs 1101-1102 at the end of the slot 910 in the mount 452 forming a circle 1110. The looseness of the body 702 of the nozzle assembly in the mount 452 allows the nozzle assembly to pivot slightly about the axis 1100, and the nose end 716 to grind debris away from the two points of contact with the nubs. This assures the opening in the nozzle is more aligned along the axis 1100 with the flow channel in the cuvette 406.

Alternatively, assume the nozzle assembly 450 is pulled out of the slot 910 from the mount 452 for maintenance. A user squeezes two fingers into the left and right finger grabs 712L-712R of the body 702 and pulls out on the nozzle assembly 450 sliding it out of the slot 910 and away from the mount 452.

FIGS. 8B-8C, 9B-9C, and 10B-10C illustrate views how the nozzle assembly 450 in the mount 452 is raised and lowered by the flow cell linkage 440 and carriage assembly 442 to respectively press and un-press an O-ring seal of the nozzle assembly 450 up against the cuvette 406.

Figures 8A, 8B:
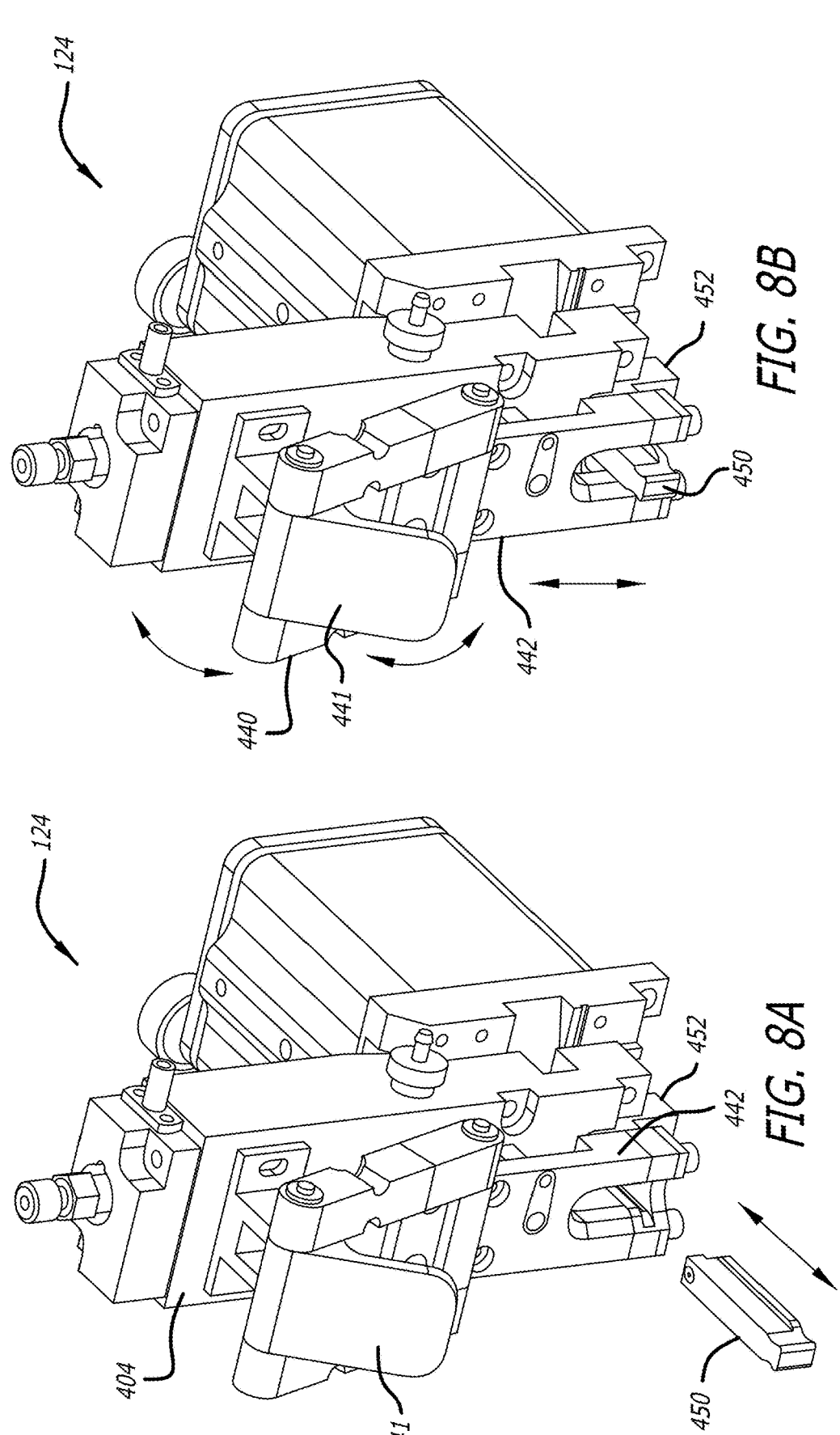
FIG. 8A is a view of engagement/disengagement of the nozzle assembly with the flow cell of the compact cell sorter system.
FIGS. 8B-8C are perspective views of the flow cell illustrating carriage and nozzle assembly movement down and up as the lever arm is pivoted.
Figures 9A, 9B, 9C:
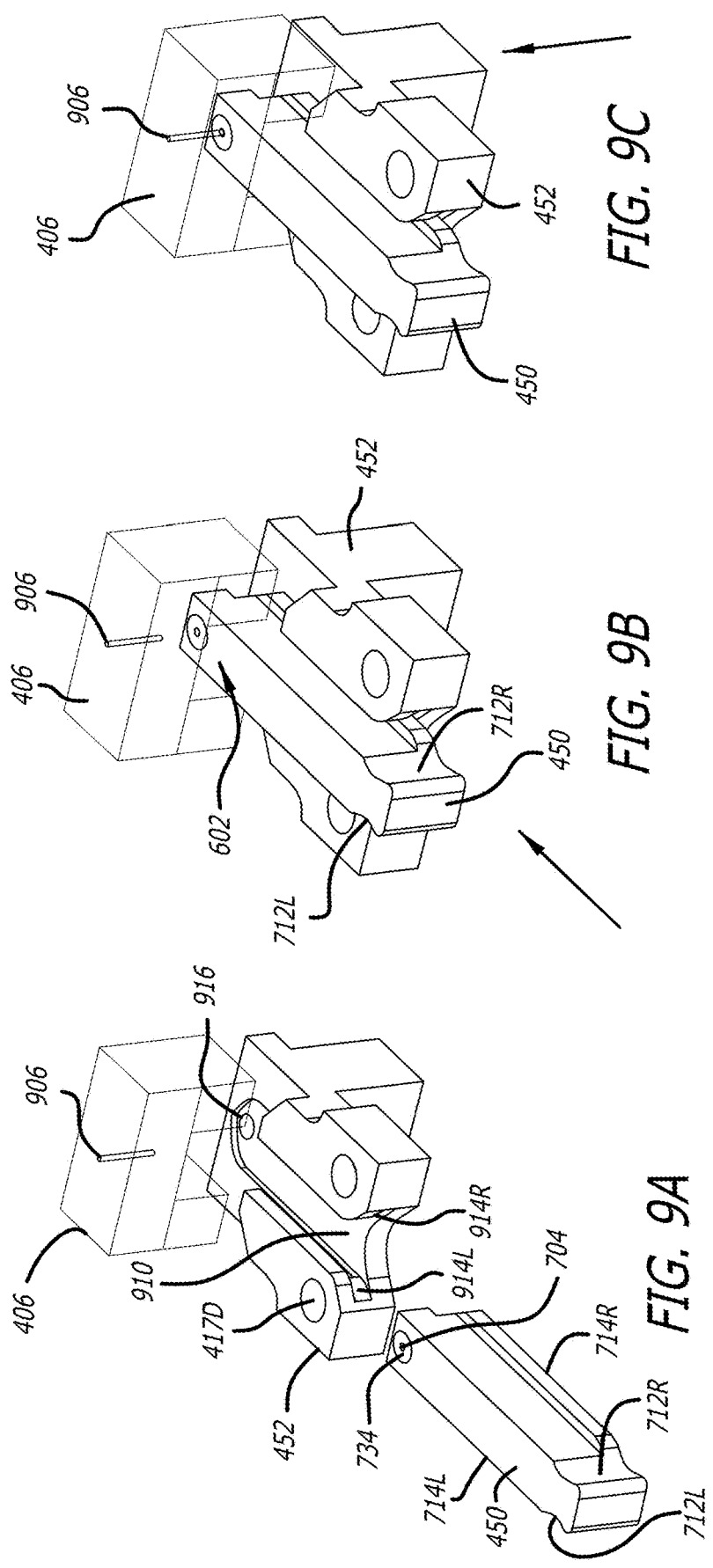
FIG. 9A is a perspective view of engagement/disengagement of the nozzle assembly with the nozzle mount of the flow cell.
FIGS. 9B-9C are perspective views of the registered nozzle assembly moving up to engage the cuvette as the lever arm is pivoted.
Figures 10A, 10B, 10C:
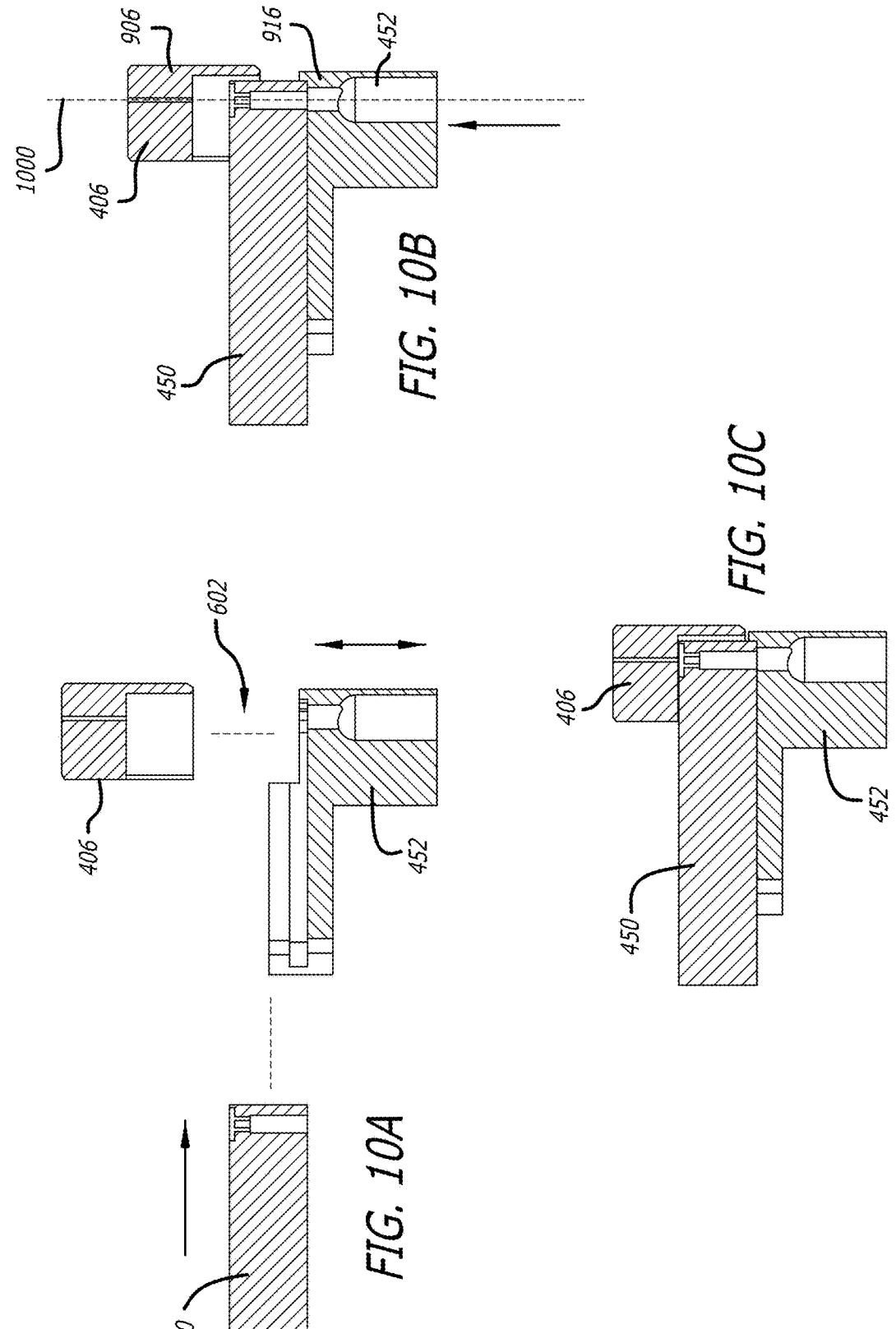
FIG. 10A is a cross-sectional view of engagement/disengagement of the nozzle assembly with the nozzle mount of the flow cell.
FIGS. 10B-10C are cross-sectional views of the registered nozzle assembly moving up to engage the cuvette as the lever arm is pivoted.

In FIGS. 8B, 9B, and 10B, release lever 441 and the nozzle assembly 450, engaged in the mount 452 of the carriage assembly 442, are in a lowered position. In the lowered position, a gap 602 exists between the cuvette 406 and the nozzle assembly 450 as shown in FIGS. 9B and 10B. To engage the nozzle assembly 450 with the Cuvette 406, a user lifts up on the release lever 441 pivoting it about the shaft 445C. This causes the linkage assembly 440 to pivot forward into the flow cell body about the shaft 445B and lift up on the lever arms 444L-444R and the carriage assembly 442. With the nozzle assembly 450 mounted in the mount 452 of the carriage assembly 442, the nozzle assembly is lifted up together with the carriage assembly.

Figure 8C:
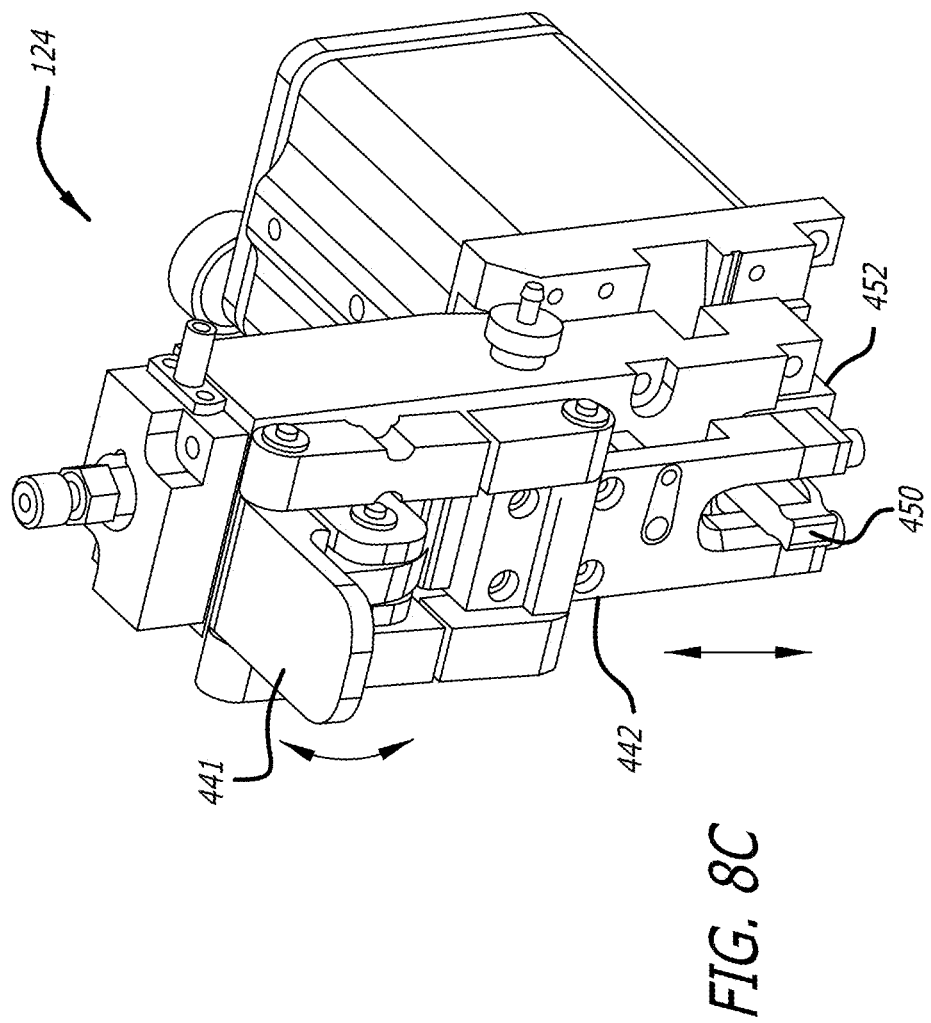

In FIGS. 8C, 9C, and 10C, the release lever 441 and the nozzle assembly 450, engaged in the mount 452, are in a raised or upper position. The gap 602 between the nozzle assembly and the cuvette 406 is substantially reduced and forces the O-ring seal of the nozzle assembly up against a base of the cuvette 406 around the flow channel 906.

The spring loaded detent slidingly engages the backside cam 425 of the release lever 441 to maintain a selected position of the linkage, carriage assembly, and nozzle assembly. From the lower position to the upper position of the release lever 441, the spring loaded detent 461 rides on a lower part of the backside cam 425 and comes to rest against an upper part of the backside cam as shown in FIG. 4D. Between the lower part and the upper part of the backside cam 425 is a bump that has a larger radial distance from the shaft 445C than that of the lower part of the cam. The upper part of the cam can have a similar radial distance or smaller radial distance to the shaft than the bump. Accordingly, with the release lever in the upper position, the compression spring 427 behind the detent 461 is compressed more and applies more force against the cam 425. This spring force on the detent and the upper portion of the cam helps maintain the release lever in the upper position. A user pushes down on the release lever 441 to overcome the force and friction applied by the spring loaded detent in the upper portion and move the cam to the lower portion actuating the linkage 440 in order to lower the carriage 442 and the nozzle assembly 450.

To disengage the nozzle assembly 450 from the cuvette 406, a user pushes down on the release lever 441 pivoting it about the shaft 445C. This causes the linkage assembly 440 to pivot forward away from the flow cell body about the shaft 445B and let down the lever arms 444L-444R and the carriage assembly 442. With the nozzle assembly 450 mounted in the mount 452 of the carriage assembly 442, the nozzle assembly is lowered down together with the carriage assembly. Accordingly, in the lowered position, the large gap 602 is formed between the cuvette 406 and the nozzle assembly 450 to allow the nozzle assembly 450 to be slid out from the mount 452 without damaging the cuvette 406. With the nozzle assembly 450 slid out and away from the mount, a new nozzle assembly may be installed in its place and/or maintenance can performed on the used nozzle assembly and reinstalled when completed.

Flow Cell Body

FIGS. 12A-12F illustrate various views of the flow cell body 404. FIGS. 13A-13B illustrate the advantages of the flow cell body 404 being formed out of an opaque material. In accordance with some embodiments, the opaque material of which a majority of the flow cell body is formed is from out of an opaque polymer with a solid three dimensional body that is machined into a desired shape with openings and chambers. In some embodiments, the opaque polymer is a black polymer.

The flow cell body has top, bottom, left, right, front and back sides. In the top side, the flow cell body includes a top chamber opening 1200 into a chamber 1250 of the flow cell body 404. As shown in FIG. 12G, the chamber 1250 includes an upper circular cylindrical portion 1252 and a lower funnel portion 1253. In the top side, the flow cell body further includes one or more top side female threaded openings (screw hole openings) 1202A-1202B to receive one or more male threaded fasteners (e.g., threaded screws or threaded bolts) to couple a hub of the drop drive assembly to the flow cell body. But for the hub, the drop drive assembly (including the sample injection tube) is mounted through the top opening 1200 into the chamber 1250. The flow cell body receives the sample fluid from the sample injection tube of the drop drive assembly.

In one side (e.g., left side), the flow cell body includes an input port 1254 coupled in communication with the fluidics system of the cytometer to receive sheath fluid. The input port receives a hose fitting 418 as shown in FIG. 4C. The input port 1254 provides an opening into the upper portion 1252 of the chamber adjacent the top of the lower funnel portion 1253.

In an opposite side (e.g., right side), the flow cell body includes an output port 1256 in line with the input port 1254. The output port 1256 receives a conductive hose fitting 419 as shown in FIG. 4C. The conductive hose fitting 419 is formed of a metal so that an electrical connection can be made to it by the sort controller. Through this electrical connection and conductive hose fitting, the sort controller can impart a positive or negative charge to the sheath fluid which is communicated to the droplet(s) generated by the nozzle by virtue of the conductivity of the sheath fluid (salt water). The sort controller can also hold the conductive hose fitting to a ground signal level such that no charge is imparted to the sheath fluid and the drops out of the nozzle are uncharged. The metal hub of the drop drive assembly 402 is grounded above the flow cell body and the metal nozzle mount of the nozzle assembly 450 below the flow cell body are grounded to avoid changing the charge added to drops by the conductive hose fitting 419 in the drain/charge port. It is desirable to maintain the charge transferred to a drop by the fitting 419, if any, as much as possible so it properly reaches the deflection unit below the flow cell 124.

Similar to the input port, the output port 1256 similarly provides an opening into the upper portion 1252 of the chamber adjacent the top of the lower funnel portion 1253. The output port 1256 can evacuate the sheath fluid to a waste tank. Upon start up, the output port 1256 is used in combination with the input port 1254 to start the sheath fluid to circulate in the lower chamber to eliminate air bubbles that might otherwise disturb the sample stream.

The funnel portion 1253 of the chamber 1250 forms the fluid stream of the sample fluid surrounded by the sheath fluid and directs the sample fluid out of the chamber through a lower chamber opening 1255. The pressure of the sheath fluid and the sample fluid are independently controlled to achieve a desired flow rate of sample fluid surround by sheath fluid out of the chamber 1250 and into the flow channel 906 of the cuvette 406.

Figure 12B:
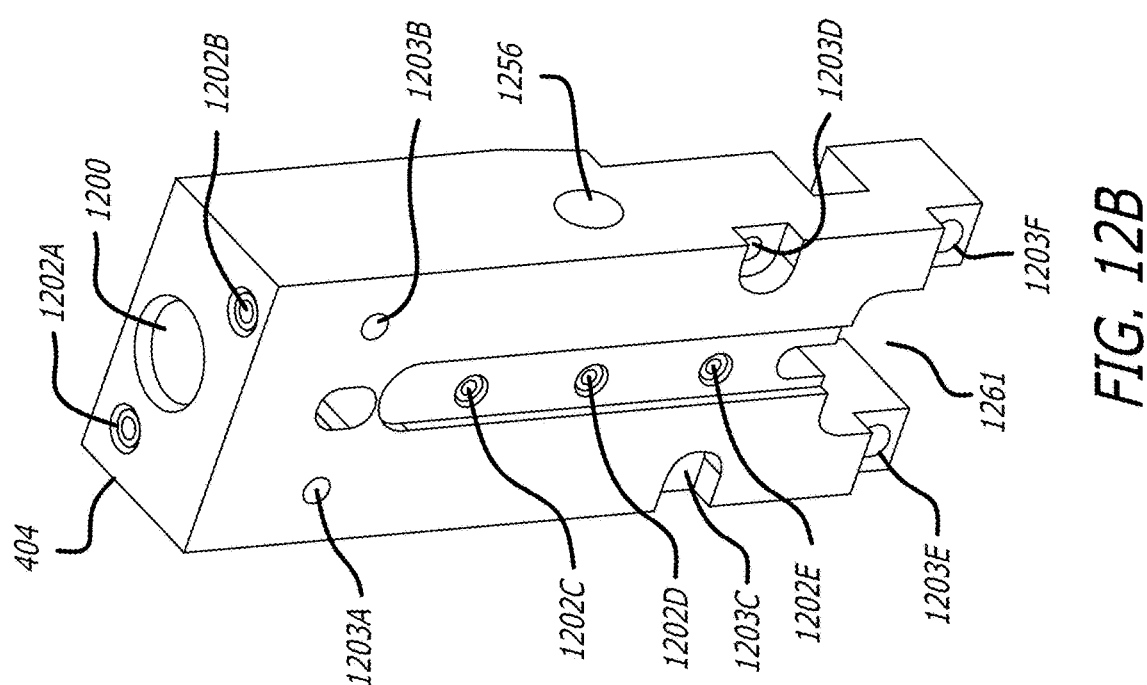
FIGS. 12A-12B are perspective views of the flow cell body.
Figure 12A:
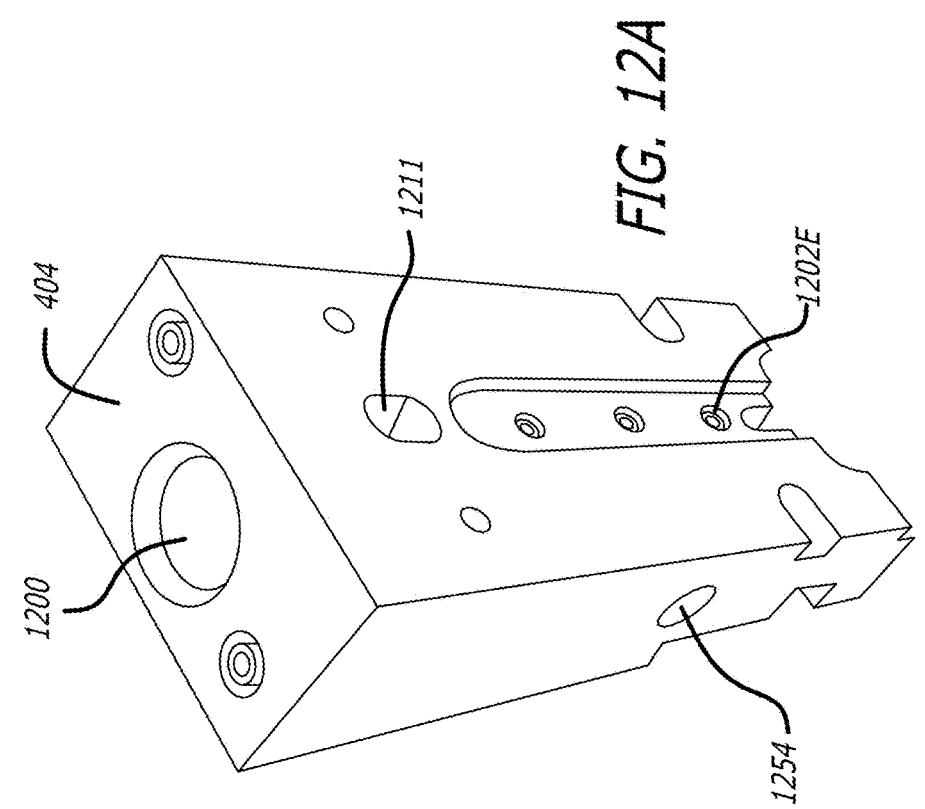
Figures 12C, 12D, 12E, 12F:
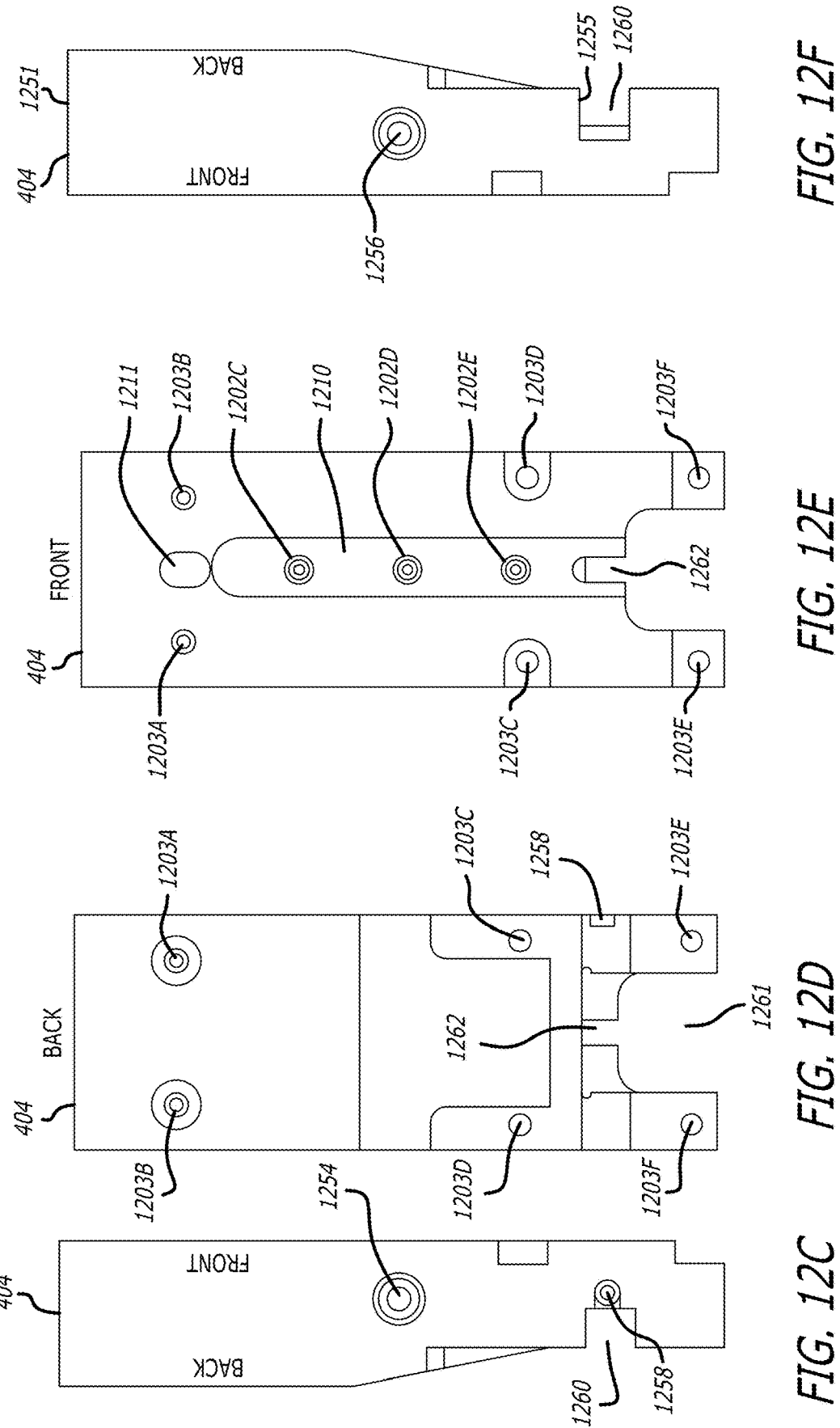
Figure 12I:
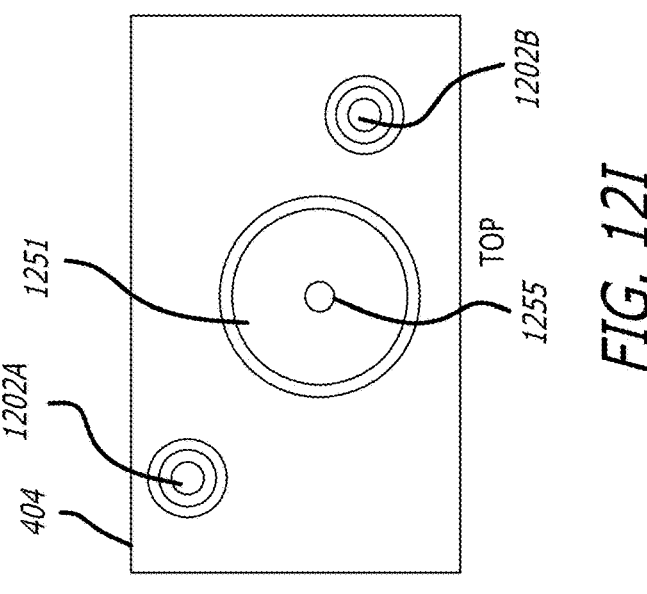
Figure 12H:
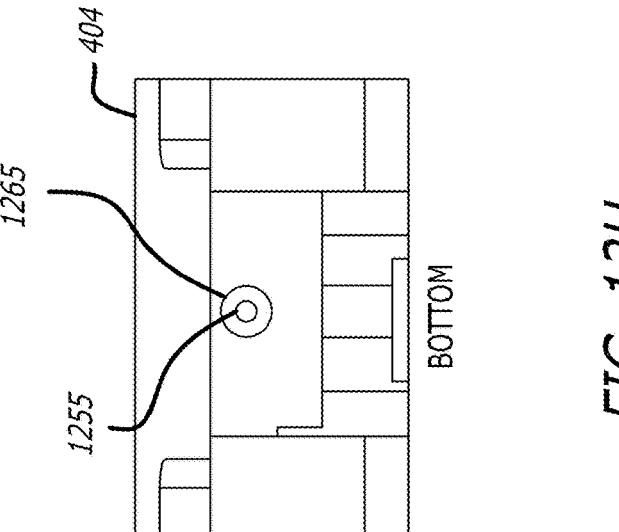
Figure 12G:
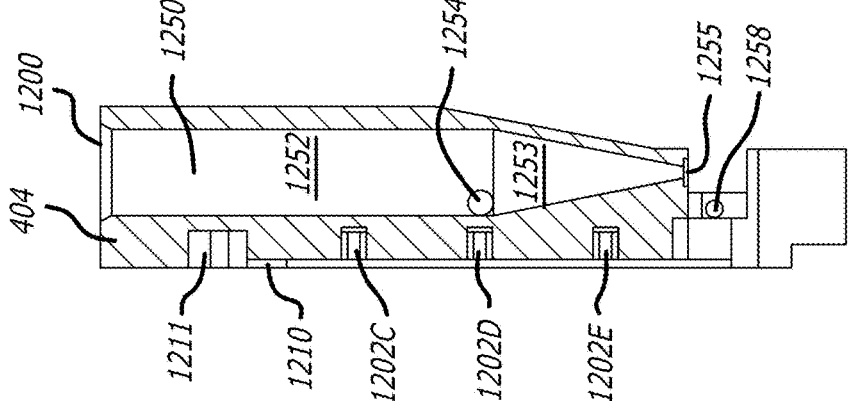
Figures 13A, 13B:
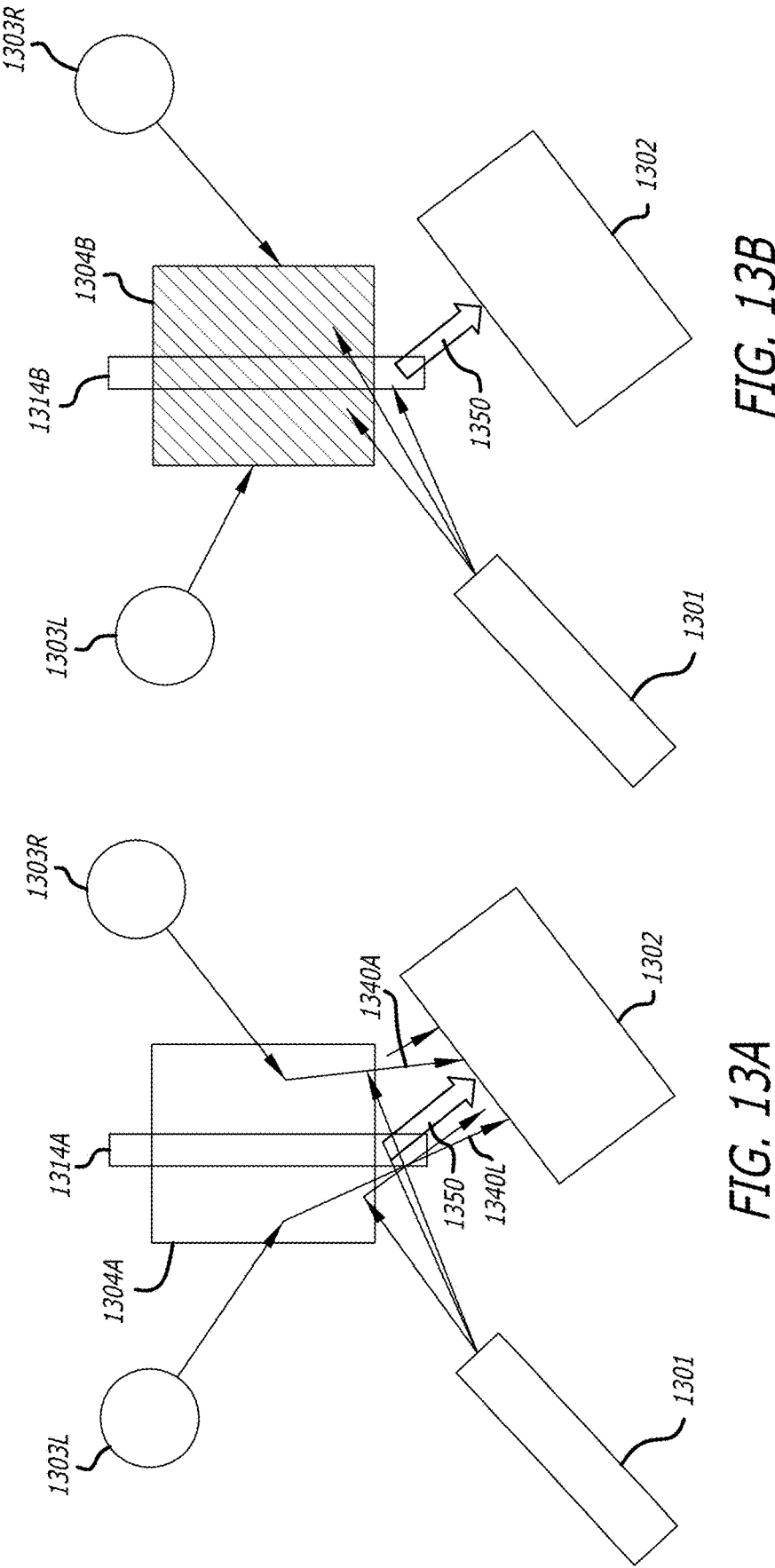
FIGS. 13A-13B are diagrams illustrating the benefit of a black flow cell body.

To support the movement of the linkage 440 and the carriage assembly 442, the flow cell body 404 can include a plurality of threaded openings 1202C-1202E in a slot 1210 of the front side as best shown in FIG. 12E. The threaded openings 1202C-1202E can receive threaded fasteners through holes in the linear slide rail 446 to mount it to the front side of the flow cell body. The linear slide rail 446 is used to allow the nozzle carriage assembly 442 to slide up and down with respect to the release lever 441 and the linkage 440. The flow cell body can further include a shallow oval opening 1211 in the front side to receive the spring 427 and the detent 461 (spring loaded detent) for holding the position of the release lever 441, the linkage, the carriage assembly, and the nozzle assembly. The hole or opening 1211 is oval in order to allow the spring and the detent to move up and down with adjustments in position of the hinge bracket 443.

In the front side and back side, the flow cell body can include through holes 1203C-1203F near the left and right sides to receive threaded fasteners with threaded shafts that extend though the flow cell body from the front and into threaded holes in the Objective Lens Mount. The top two through holes 1203A-1203B are used to mount the hinge bracket 443 to the front of the flow cell body. The threaded shaft of the threaded fasteners is inserted through the though holes 460 in the left and right sides of the base of the hinge bracket 443 and threaded into the threaded inserts installed in the holes 1203A-1203B in the flow cell body. In an alternate embodiment, the top two through holes 1203A-1203B can be threaded openings instead of using a threaded insert.

An opening or pocket 1260 in the back side of the flow cell body, from left side to right side, is formed in the flow cell body 404. The pocket 1260 receives the cuvette 406 so that the flow channel 906 lines up with the stream of drops from the bottom opening 1255 in the chamber 1250. A threaded side opening 1258 receives a threaded set screw with a soft nylon tip to press against the side of the cuvette 406 and hold it in place mounted within the opening 1260 to the flow cell body.

For the most part, the cuvette 406 is hidden from view in the front side by the opaque body of the flow cell 404 and the carriage assembly and nozzle assembly mounted in the mount. The pocket 1260 has an open left side and an open right side that allow laser light from one or more lasers to pass into the side of the cuvette and strike the cells/particles flowing in the flow channel. The laser light may be injected into the cuvette on one side and collected on an opposite side by an optical fiber or forward scatter detector.

A base or bottom side of the flow cell body 404 has a large cutout (pocket opening) 1261 from front to back that leads into a small cutout (upper arched cutaway) 1262 from front side to back side. Because the cuvette is fairly well hidden, the small cutout 1262 allows a microscope test instrument to be inserted through the front side of the flow cell body to view the flow channel in the cuvette 406 from the front side of the flow assembly 124.

The large cutout 1261 in the base of the flow cell body allows the nozzle assembly 450 to be mounted into the mount 452 below the cuvette 406. The large cutout 1261 further allows the nozzle assembly 450 to be moved up and down by the linkage 450 and the carriage assembly below the flow cell body and the cuvette.

Through holes 1203C-1203F in the flow cell body allow shafts of threaded fasteners (e.g., bolts or screws) to pass through from front side and back side and thread into a threaded hole in the frame of the cell sorter or the lens assembly behind the flow cell body. That is, the threaded bolts couple the flow cell body 404 directly or indirectly to the frame of the cell sorter. The front surface of the flow cell body can be cut back so that the heads of the fasteners are below the main front surface of the flow cell body.

In some embodiments, some or all of the threaded openings (collectively referred to as threaded openings 1202) in the flow cell body 404 may include a female threaded insert mounted into a hole in the flow cell body to form the threaded opening and receive the male threaded fastener. Some groups of the threaded openings can have similar dimensions or different dimensions from other groups of threaded openings. In which case, the dimensions of the various threaded fasteners would differ.

FIG. 13A shows a flow cell body 1304A formed out of a non-opaque or a somewhat reflective material. A laser 1301 generates a laser light that is used to excite fluorescent dyes attached to a cell or strike the cell itself to determine certain characteristics of the cell. The laser light is mostly directed to an interrogation region in the flow channel 1314A to strike passing cells/particles in a sample. A detector 1302 is used to detect the wavelengths of fluorescent light that is given off by an excited dye and/or reflect or scatter off of a cell in the flow channel 1314A as a light signal 1350. Unfortunately, a portion of the laser light may strike the non-opaque flow cell body 1304A and can be directed by light piping, reflected or deflected as light noise back 1340L towards the detector 1302. The extra light noise decreases a signal to noise ratio at the detector 1302 of the fluorescent light (or scattered light off the cell) that is desirable to capture and analyze. Ambient light sources 1303L and 1303R can also decrease the signal to noise ratio at the detector 1302 around the non-opaque flow cell body 1304A.

Another source of light noise into a detector 1302 can be ambient light. The left ambient light source 1303L emits light that strikes the non-opaque flow cell body 1304A and is directed, deflected or reflected into the detector 1302 as light noise 1340A. Similarly, the right ambient light source 1303R emits light that can strike the non-opaque flow cell body 1304A and be deflected or reflected as light noise 1341 into the detector 1302 as light noise 1340A. Accordingly, the ambient light from ambient light sources can also be deflected or reflected off the non-opaque flow cell body 1304A as light noise and reduce the signal to noise ratio at the detector 1302.

FIG. 13B shows a flow cell body 1304B formed out of an opaque material that does not deflect or reflect light very well. A portion of the laser light generated by the laser 1301 that may stray and strike the opaque flow cell body 1304B is generally not directed, reflected or deflected towards the detector 1302. Similarly, the ambient light from ambient light sources 1303L and 1303R that may stray and strike the opaque flow cell body 1304B is generally not directed, reflected or deflected towards the detector 1302.

The opaque flow cell body 1304B advantageously reduces the background light and avoids light piping of light noise sources into the detectors of the cell sorter. The light signal 1350 from the fluorescent light (or scattered light off the cell) that is desirable to capture and analyze, enjoys greater signal strength over the light noise. Accordingly, the detector 1302 around the flow cell body 1304B enjoys an improved signal to noise ratio over that of detector 1302 around the flow cell body 1304A shown in FIG. 13A.

Drop Drive Assembly

FIGS. 14A-14C and 15 illustrate views of the drop drive assembly 402. The drop drive assembly 402 of the flow cell 124 is in communication with the sample input station 130 of the fluidics system to receive sample fluid. Tubing couples the flow cell and sample input station in communication together. Generally, the drop drive assembly 402 receives the sample fluid under pressure through the sample input port 408 at one end. At an opposite end, the drop drive assembly 402 forms a stream of sample fluid out of sample injection tube (SIT) 422.

Figure 15:
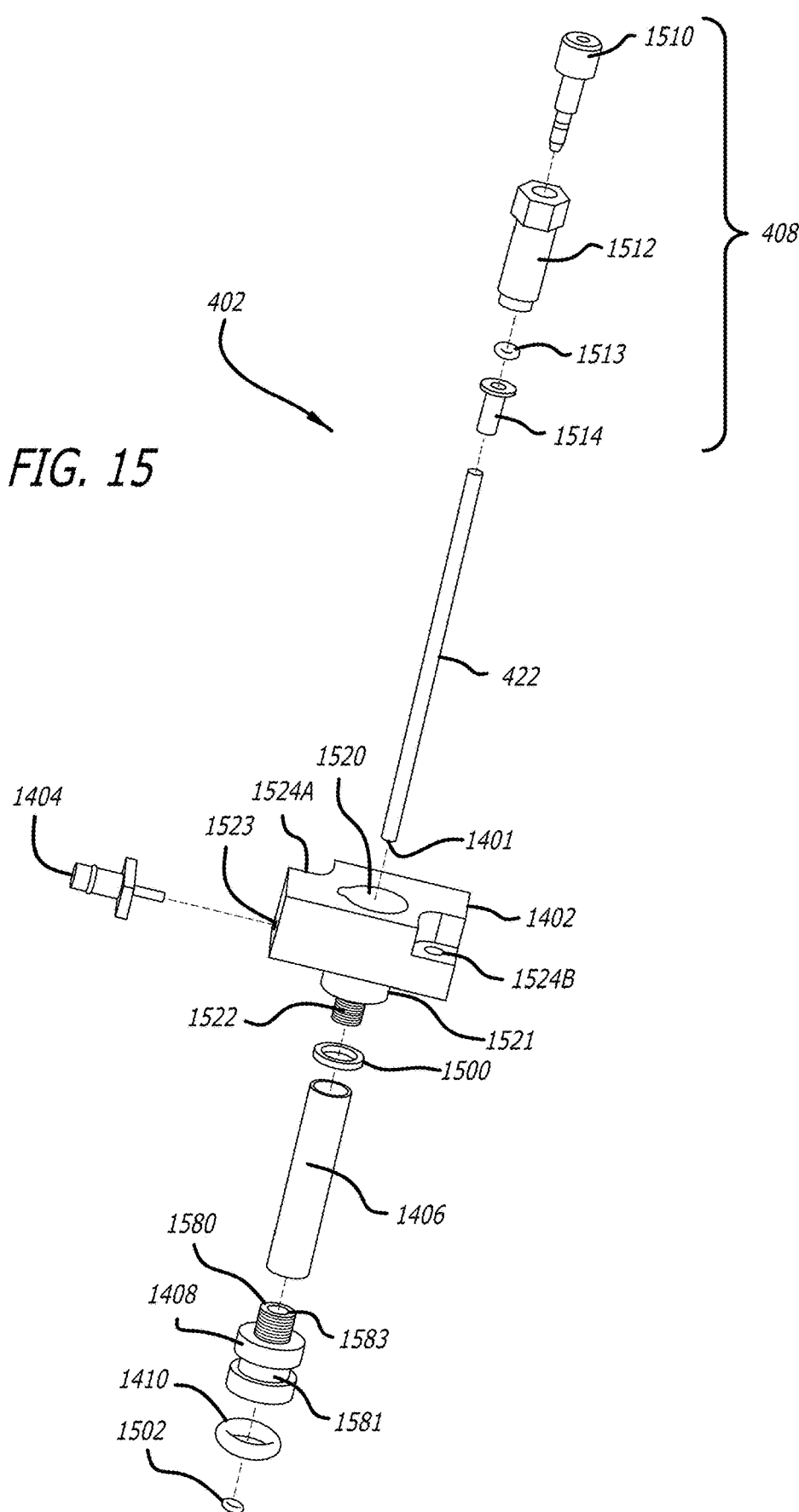
FIG. 15 is an exploded view of the drop drive assembly with a glass sample input tube (SIT) that is insertable into the flow cell body of the compact cell sorter system.

As shown in FIG. 15, the drop drive assembly 402 includes the sample input port 408, the sample injection tube (SIT) 422, an outer metal hub 1402, an electrical jack 1404, an insulating spacer 1500, a hollow piezoelectric cylindrical transducer 1406, an insulated cylindrical sealing base 1408, a first sealing O-ring 1410, and a second sealing O-ring 1502. These components are assembled together about the outer metal hub 1402. The sample input port 408 into the SIT 422 can include a male nut 1510 with or without an integrated ferrule, a pipe adapter 1512, one or more ferrules if the male nut does not include an integrated ferrule, a third sealing O-ring 1513, and a hollow PEEK sleeve 1514. The mail nut 1510, the pipe adapter 1512 and ferrule receive hollow tubing (see FIG. 1C) and couple it to the drop drive assembly to receive the sample fluid.

Figures 14A, 14B:
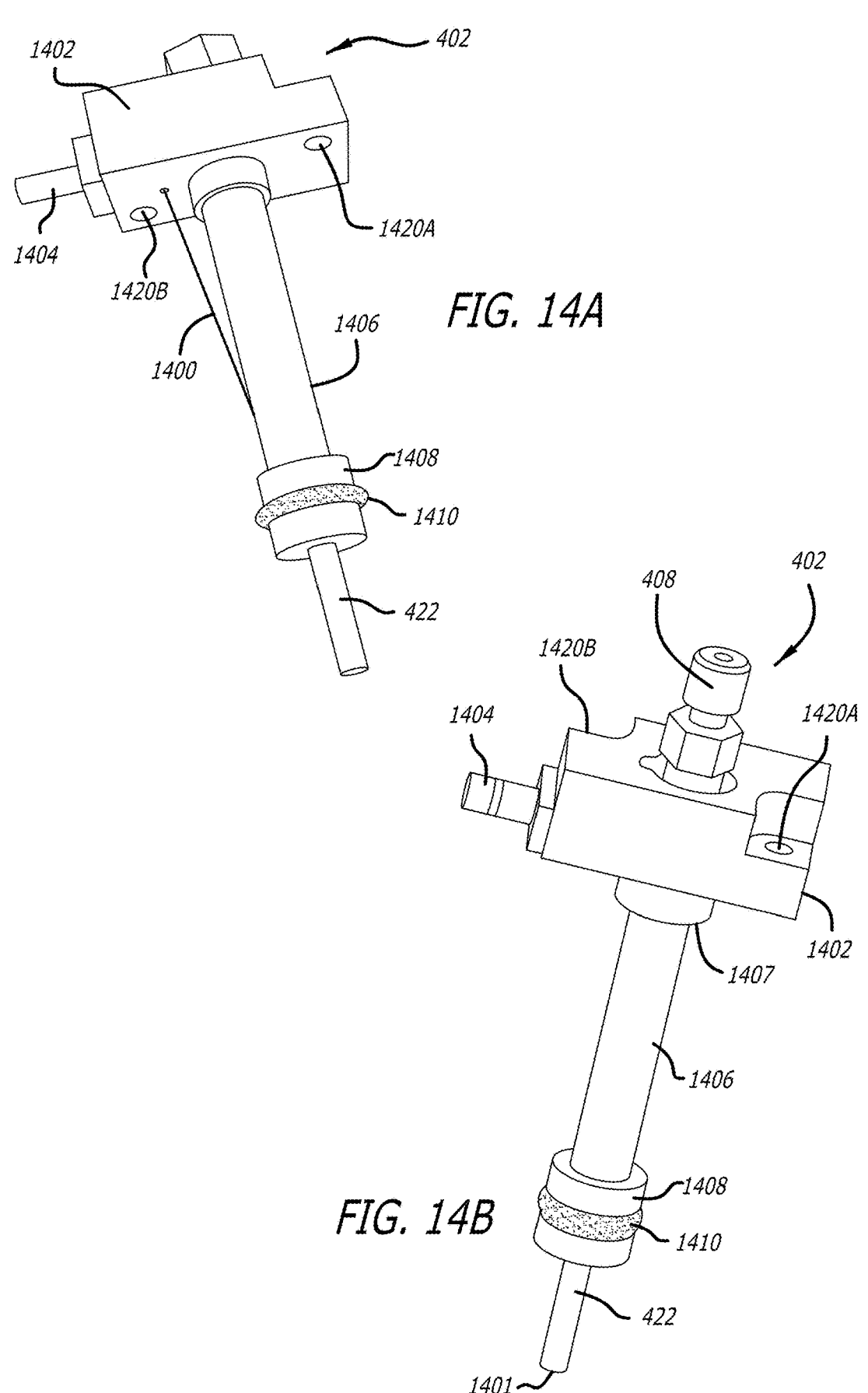
FIGS. 14A-14B are perspective views of the drop drive assembly with a glass sample input tube (SIT) that is insertable into the flow cell body of the compact cell sorter system.
Figure 14C:
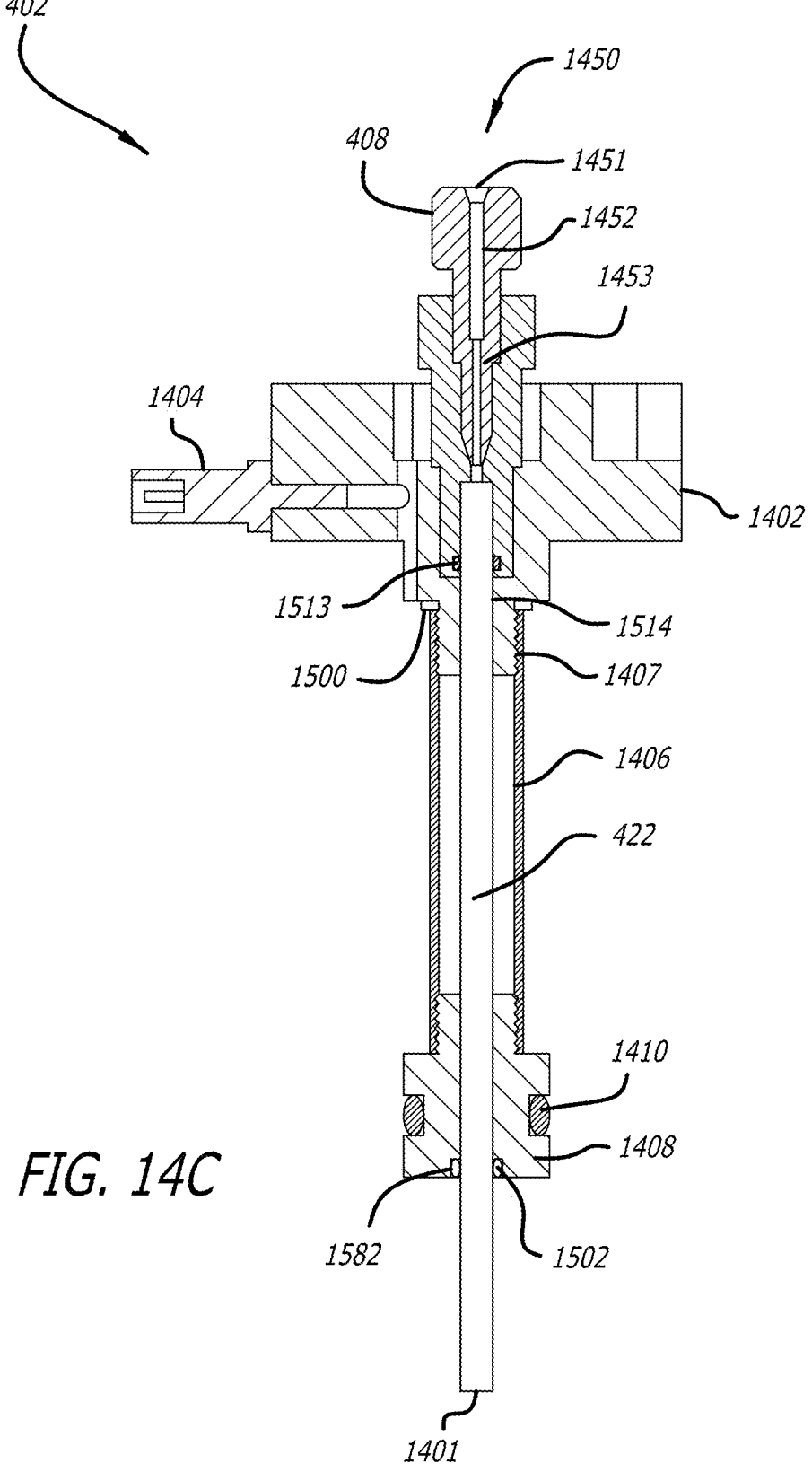
FIG. 14C is a cross sectional view of the drop drive assembly with a glass sample input tube (SIT) that is insertable into the flow cell body of the compact cell sorter system.

As shown in FIG. 14C, the sample input port 408 has a center channel 1450 through which the tubing is received. The center channel 1450 starts with a beveled opening 1451 enters into a center portion 1452, and ends with an end portion 1453 that is slightly narrower than the center portion. The end portion 1453 can allow the end of the tubing to be inserted into the upper end of the SIT 422. The center channel 1450 is formed by the male nut 1510 threaded into the pipe adapter 1512. The pipe adapter 1512 includes male threads on one end to threadingly engage the threads in the opening 1520 in the hub 1402. The pipe adapter 1512 has a lower opening at a lower end in communication with the center channel 1450. The lower opening of the pipe adapter receives the top end of the SIT 422.

A hollow PEEK sleeve (SIT Shell Isolator) 1514 with a top flange slides over the top end of the SIT 422. The top flange of the sleeve engages a base in the center opening 1520 of the hub 1402. The sleeve electrically isolates the glass SIT from the metal hub 1402. A third sealing O-ring 1513 is slid over the upper end of the SIT 422 and butts up against the top flange of the sleeve 1514. The pipe adapter 1512 has external threads at its lower end to engage the internal threads in the center opening 1520 of the hub. As the pipe adapter 1512 is screwed into the hub, it compresses the third sealing O-ring 1513 against the top flange of the sleeve 1514 to seal around and hold the glass SIT in position. The pipe adapter has internal female fitting (threads) at a top end opposite the lower end to engage the male nut 1510. The male nut has a through hole opening and male threads in an outer surface to engage the pipe adapter. Hollow tubing can be inserted through the through hole opening in the male nut with an end thereof extending just beyond an end of the male nut. A ferrule can be integrated into the male nut 1510. Alternatively, with the hollow tubing extending just beyond the end of the male nut, a ferrule can be added over the end of the hollow tubing. In either case, the ferrule is received and engages the pipe adapter.

As can be seen in FIGS. 14C and 15, the outer metal (piezo) hub 1402 has a center opening 1520 extending from top to bottom and through a flange 1521 and through an extended hollow circular plug 1522. The wall of the center opening 1520 in the outer metal hub is partially threaded to receive the components of the sample input port 408 and an upper end of the SIT 422. The hub 1402 can further include a threaded side port 1523 to receive the electrical jack 1404 and a plurality of bolt through holes 1524A-1524B to receive a plurality of fasteners to mount and couple the hub of drop drive assembly to the flow cell body 404.

The lower portion of the drop drive assembly below the hub 1402 is inserted into the chamber 1250 of the flow cell body 404, such as can be seen in FIGS. 4D-4G and 12G. As shown in FIGS. 4E-4F, when the drop drive assembly 402 is mounted into the flow cell body 404, the lower end 1401 of the sample injection tube 422 is located in the funnel portion 1253 of the chamber 1250. The insulated cylindrical sealing base 1408 of the drop drive assembly 402 is located in the upper portion 1252 of the chamber just above the input port 1254 in the chamber. With the O-rings 1410,1502, the insulated cylindrical sealing base 1408 seals off the chamber 1250 of the flow cell body so that the sheath fluid and the sample fluid are kept from reaching the hollow piezoelectric cylindrical transducer 1406 and shorting out power and ground terminals supplied by the electrical jack 1404. The insulating spacer 1500 extends over the extended hollow circular plug 1522 up to a flange 1521 in a base of the outer metal hub 1402. This helps keep the piezoelectric cylindrical transducer 1406 from shorting to ground to which the hub is coupled by the electrical jack 1404.

The hollow piezoelectric cylindrical transducer 1406 has a hollow upper end coupled over the extended hollow circular plug 1522 of the hub up to the insulating spacer 1500. The hollow piezoelectric cylindrical transducer has an inner terminal that can couple to the extended hollow circular plug 1522 and form a first electrical connection to the outer metal hub 1402 and ground through the electrical jack 1404. A wire 1400 coupled to a power terminal of the jack 1404 at one end couples to the second (outer) terminal of the hollow piezoelectric cylindrical transducer 1406. As best viewed in FIG. 15, the insulated cylindrical sealing base 1408 has an extended hollow circular plug 1580 that couples into a lower end of the hollow piezoelectric cylindrical transducer 1406. The hollow ends of the hollow piezoelectric cylindrical transducer are glued to the extended hollow circular plugs 1522,1580. Each of the extended hollow circular plugs 1522,1580 includes a plurality of ridges to retain the adhesive glue between the circular plug and the inner surface of the hollow piezoelectric cylindrical transducer.

The insulated cylindrical sealing base 1408 has a ring groove 1581 around an outer cylindrical surface. The ring groove 1581 receives the outer O-ring 1410 to seal against the cylindrical wall of the chamber as shown in FIGS. 4E-4D. This seal keeps fluid from flowing up into the chamber around the outside of the hollow piezoelectric cylindrical transducer. The insulated cylindrical sealing base 1408 has a through hole 1583 to receive a portion of the SIT 422. The insulated cylindrical sealing base 1408 further has a gland ring 1582 in the inner cylindrical surface of the through hole 1583 near the lower end opposite the plug 1580. The gland ring 1582 receives the inner O-ring 1502 to seal around the SIT 422 as show in FIG. 14C. This seal keeps fluid from flowing up through the through hole 1583 into the interior of the hollow piezoelectric cylindrical transducer.

The hollow piezoelectric cylindrical transducer 1406 mounts around a portion of the SIT 422 when assembled together. Sample fluid with cells/particles flows within the hollow center cylinder of the SIT 422. When energized by an alternating current (AC) signal (amplitude and frequency selectable) from the electronics system, the hollow piezoelectric cylindrical transducer 1406 vibrates based on frequency and amplitude of the AC signal. The vibrations are coupled into the insulated cylindrical sealing base 1408 such that the sample fluid receives acoustical energy that can help convert the sample fluid into a stream of small drops spread out in a single file line out of the nozzle. Ideally, each drop has a single cell/particle but cells/particles of interest can vary in size. The diameter of the opening in the nozzle, the sheath pressure, and fluid viscosity can vary the size of drops and their frequency of generation. For a given sheath fluid pressure, the AC signal frequency and amplitude can be set for resonance where droplet formation is stable and yields a desired drop size. The nozzle assembly can be readily swapped in and out to get a different diameter of nozzle opening.

The sample injection tube (SIT) 422 has a lower end inserted into and through the center opening 1520 in the outer metal (piezo) hub, the center of the hollow piezoelectric cylindrical transducer 1406, and the through hole 1583 in the insulated cylindrical sealing base 1581. As seen in FIGS. 14A-14C, the lower end of the sample injection tube (SIT) 422 extends out of the through hole 1583 in the insulated cylindrical sealing base 1408 to inject the sample fluid into the funnel portion 1253 of the chamber 1250 in the flow cell body. The upper end of the SIT 422 is in communication with the sample input port 408 and the tubing to receive the flow of sample fluid.

The SIT 422 is a hollow cylindrical glass SIT formed out of a hollow cylindrical glass tube with a minimum external diameter of about 2.00 millimeters (e.g., between 2.05 mm to 3.18 mm) and an internal diameter of about 0.17 millimeter (e.g., between 0.17 mm to 0.45 mm). The minimum diameter of the glass SIT is greater than the minimum diameter of a stainless steel SIT. The total length of the glass SIT is not more than 70 millimeters to provide sufficient stiffness and avoid breakage during installation and service. An outside edge of the end 1401 of the SIT 422 is chamfered or beveled to allow the stream of sample fluid to merge with the sheath fluid in a stable manner.

The O-ring seal 1502 can be a low cost standard off the shelf O-ring to seal around the glass sample injection tube 422. In some embodiments, the O-ring seal has an unstretched inside diameter in the range of 2.0 millimeters to 3.0 millimeters, dependent upon the outside diameter of the glass sample injection tube. The O-ring seal is just small enough to provide sealing contact around the glass sample injection tube below the lower hollow circular plug.

The glass SIT 422 has a number of advantages over a stainless steel SIT. A stainless steel SIT can become etched by the chemicals in the presence of electrical charge and vibration around an O-ring seal such that it can allow fluids to leak past and damage the electronics associated with the piezoelectric crystal. Two O-ring seals are often used around stainless steel SITs to try to improve reliability as the stainless steel is etched. The glass SIT 422 will not be etched by chemicals in the presence of electrical charge and vibration around its O-ring seal. Accordingly, the drop drive with the glass SIT 422 will be more reliable and require less maintenance than a drop drive with a stainless steel SIT. A single O-ring seal is only needed around a glass SIT. Moreover, the single O-ring seal can be a low cost standard size O-ring when used with the glass SIT. The glass SIT is also less expensive than a stainless steel SIT to manufacture and replace.

Deflection Chamber

The nozzle, in the nozzle assembly of the flow cell, breaks up the sample fluid into droplets. The drops with cells of interest in a center stream are sorted out by deflecting drops away from the center stream. The drops are charged so they can be deflected away from the center stream by charged deflecting plates in the deflection chamber (unit) 122. The drops with cells of interest can be collected into separate vessels (test tubes, wells) by the DDU for further testing in a lab.

Figure 16A:
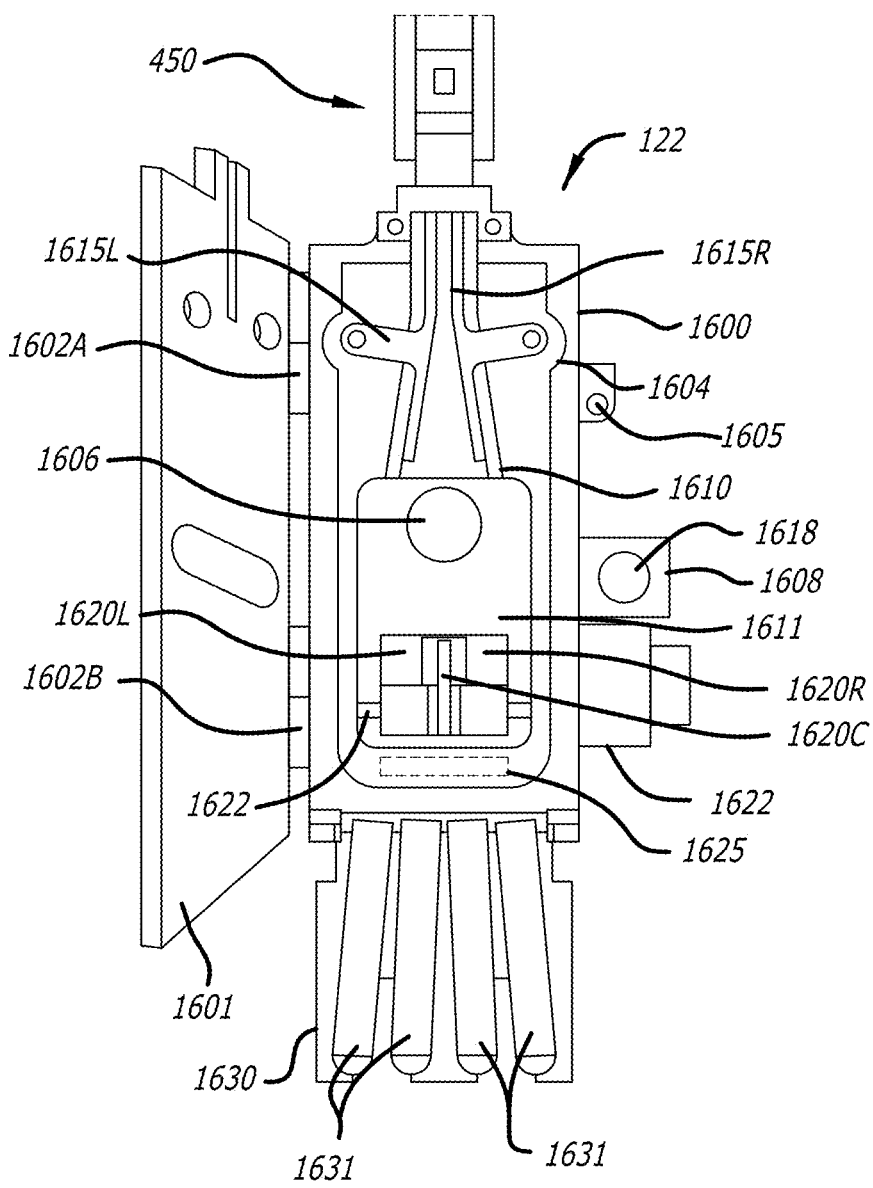
FIG. 16A is a front view of the deflection unit, with covered removed, of the sorting system of the compact cell sorter system.
Figure 16B:
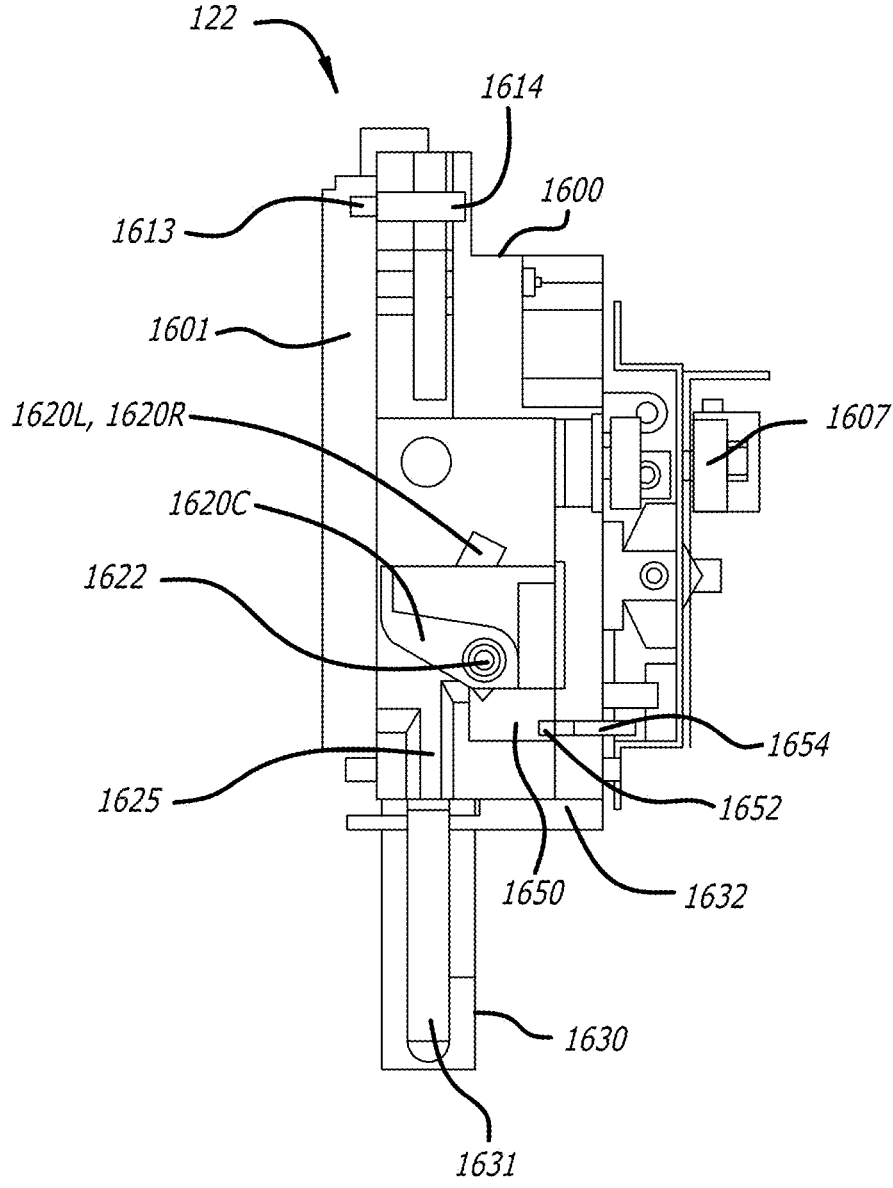
FIG. 16B is a side view of the deflection unit of the sorting system of the compact cell sorter system.

FIGS. 16A-16B illustrate the deflection (deflecting) unit 122 under nozzle assembly 450 of the flow cell 124. Accordingly, the deflection unit is in communication with the flow cell 124 to receive a plurality of drops of the sample biological fluid that are in a center stream. The back of the deflection unit 122 is mounted to a rail so that it can be horizontally adjusted from side to side.

The deflection unit 122 includes a case 1600 with a door 1601 pivotally coupled to the case by a plurality of hinges 1602A-1602B. The door 1601 includes a fastener (e.g., a catch) that can engage a latch to keep the door securely closed against the case. The case 1600 has a deflection cone cutout 1610 that opens up into a deflection chamber 1611. A seal 1604 is in a channel around the deflection cone cutout 1610 and the deflection chamber 1611 to which the door 1610 presses against. This seals the sample drops within the cutout and chamber so they are not released into ambient air.

A left electrostatic charge (deflection) plate 1615L and a right electrostatic charge (deflection) plate 1615R are mounted in the deflection cone cutout 1610 and are progressively separated further from each other from top to bottom in the cone. A left high voltage charge is applied to the left electrostatic charge plate 1615L and a right high voltage charge of opposite polarity is applied the right electrostatic charge plate 1615R to impose an electrostatic charge field through which droplets pass. If a drop is to be sorted by moving it away from a center stream of drops, a positive charge or a negative charge is synchronously applied to a drop by the conductive hose fitting in the drain/charge port and a charge signal from the sort controller. If the droplets are uncharged (grounded), they remain in the center stream. Only if a droplet is charged, by applying a charge signal (positive or negative) to the charge port on the flow cell, will it be deflected as it passes through the electro static charge field formed by the electrostatic charge plates. The degree of deflection depends on both the magnitude of the electrostatic charge field imparted by the left and right electrostatic charge plates and the polarity and magnitude of the charge imparted to the droplet by the charge port.

For example, the left electrostatic charge plate may be charged at negative 2000 Volts and the right electrostatic charge plate may be charged at positive 2000 volts to provide a 4000 volt electrostatic field between them. The voltages on the electrostatic charge plates are held constant during a sort of droplets in a sample. Droplets then may be selectively charged instantaneously (by applying charge to the conductive hose fitting in the charge/drain port on the flow cell) to achieve a desired deflection away from center. Accordingly, the precise magnitude and polarity of voltage applied to cells associated with each stream path will depend on the desired direction and magnitude of deflection needed to get the droplet into a receiving receptacle. Accordingly, multiple (e.g., 2, 3, 4, 5, 6) left deflected stream paths and multiple (e.g., 2, 3, 4, 5, 6) right deflected stream paths can be formed about the center stream path. For simplicity of the explanation herein, we will collectively refer to them herein as a left stream path (left stream) and a right stream path (right stream).

A backside of the case 1600 has a side laser window and a stream camera window 1606. A side laser light generated by a laser 1608 is directed into the deflection chamber 1611 through the side laser window. The position of the laser 1608 behind the side laser window can be adjusted by the laser position adjuster 1618. The side laser light is adjusted front to back to strike the drops of biological fluid to sense the path position of the drops. A stream camera 1607 is mounted outside the case in line with and behind the stream camera window 1606 to view the drops and determine whether or not they are in a center stream path, a left deflected stream path, or a right deflected stream path. The stream camera 1607 provides a feedback mechanism to the sort controller to be sure the charges on the charge plates are appropriate for deflection of drops into the left deflected stream path and the right deflected stream path, as well as equally charged (or no charge) for dropping in the center stream path inside the deflection unit 122.

At the base of the deflection chamber 1611 is an aspirator well (tub) 1650 with a drain to aspirate drops into the waste line out of the cell sorter. In front and below the tub in the base of the deflection chamber is a horizontal drop slot 1625. Inside the chamber 1611, a left pivotal sidestream scupper 1620L, a non-pivotal center collector 1620C, and a right pivotal sidestream scupper 1620R are mounted along a drive shaft 1622 in the tub of the deflection chamber. The non-pivotal center collector 1620C is around the drive shaft between the left and right pivotal sidestream scuppers but is undriven by the drive shaft. The left pivotal sidestream scupper and the right pivotal sidestream scupper pivot with the drive shaft between a raised position and a lowered position. The non-pivotal center collector 1620C is non-pivotal and remains in a fixed rotational position regardless, but is free to move left and right with the scuppers. Drops that are deflected and not captured by the sidestream scuppers 1620L-1620R or the center collector 1620C can fall out of the deflection unit 122 through the drop slot 1625.

With no deflection by the deflection plates, the center stream of drops from the nozzle assembly drop through the deflection cone 1610 into the deflection chamber 1611 and are caught by the center collector 1620C. The center collector 1620C and the sidestream scuppers 1620L-1620R, when in the lowered position, act somewhat like rain gutters directing the flow of drops of sample fluid. The center collector 1620C directs the drops it catches into the tub 1650 for aspiration down the drain 1652 as waste. In a lowered position, the left and right pivotal sidestream scuppers 1620L-1620R catch drops that are deflected away from the center stream and direct the drops they catch by means of a tunnel into the tub 1650 for aspiration down a drain 1652 as waste. As can be seen in FIG. 16B, the drops in the tub 1650 can be aspirated down the drain 1652 and out through the waste port 1654 by a vacuum.

In a raised position, the left and right pivotal sidestream scuppers 1620L-1620R do not catch any drops. When left and right pivotal sidestream scuppers are in the raised position and selected drops are deflected away from the center stream as deflected drops, those deflected drops of sample fluid drop past the sidestream scuppers and through the drop slot 1625 in the base of the case 1600. The deflected drops pass through the drop slot 1625 for collection in the DDU chamber 128 below the deflection unit 122.

In the case of an urgent sorter shutdown, the sorter 100 pivots the shaft and the sidestream scuppers into the lowered position such that they and the center non-pivotal aspirator 1620C catch all drops of sample fluid formed by the nozzle assembly 450, whether deflected or not, and direct the drops into the tub 1652 for aspiration down the drain and out the waste port.

Ends of the drive shaft 1622 extend outside the chamber 1611. A scupper pulley 1623 is mounted to the shaft 1622 near one end (e.g., right end). A reversable electric motor has a shaft with appropriately sized drive pulley. A belt 1624 is mounted between the drive pulley and the scupper pulley to pivot the shaft in response to the rotation by the reversable electric motor and raise or lower the sidestream scuppers.

Figures 16C, 16D:
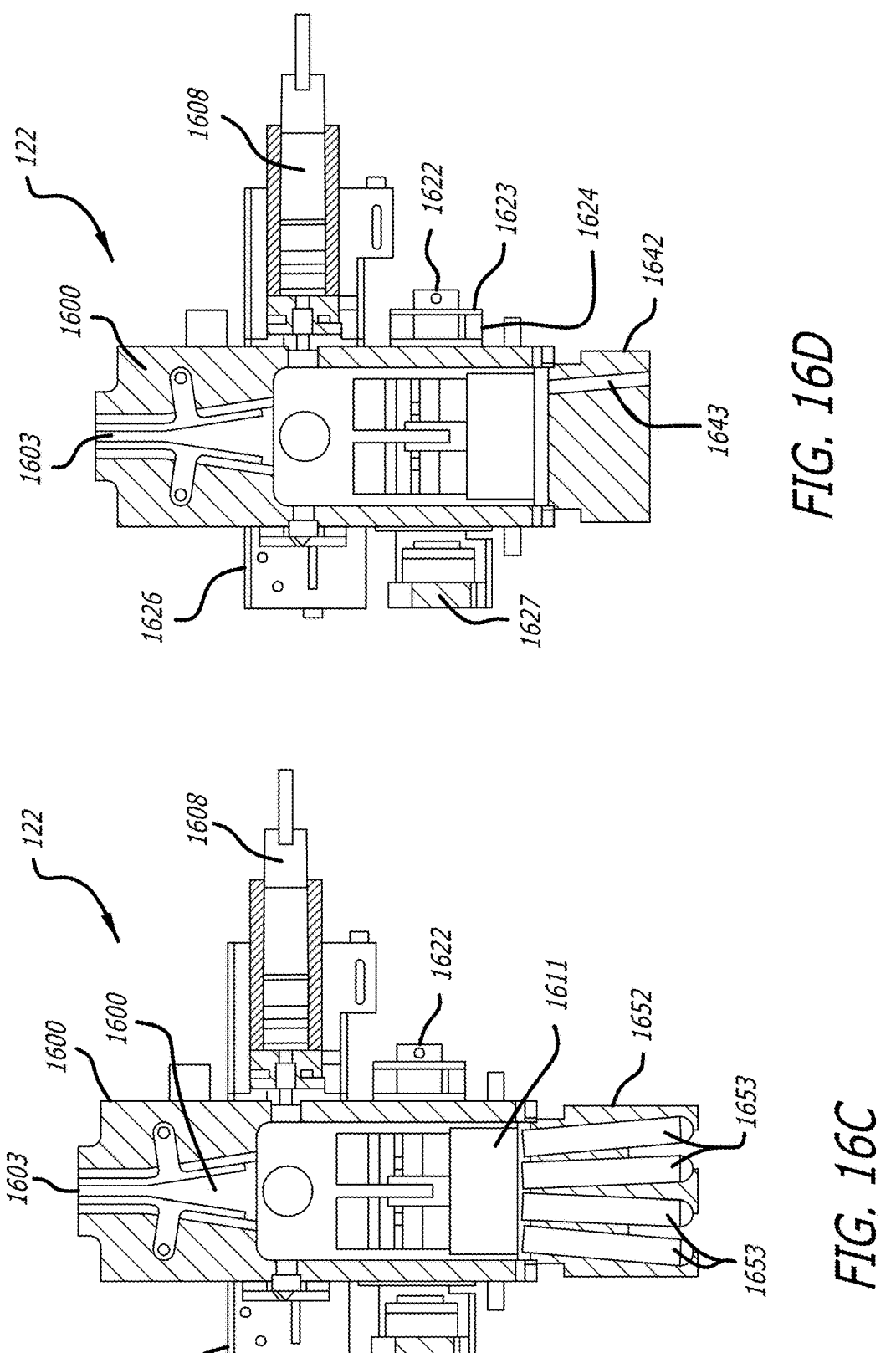
FIGS. 16C-16D are front cross sectional views of the deflection unit of the sorting system of the compact cell sorter system illustrating differences between a tube sort collection holder and a plate guide.

The deflection unit (chamber) 122 is horizontally adjustable. As shown in FIGS. 16C-16D, the deflection unit 122 can be slidingly mounted to a rail 1626 and horizontally adjustable from side to side, in order to adjust its position to the center stream path of drops that enter at a top opening 1603. The deflection unit 122 can be horizontally adjusted so that the center stream of drops is selectively positioned (equidistant or as otherwise desired) between the left charge plate 1615L and the right charge 1615R plate as the drops enter the deflection cone cutout 1610.

Because the drops can be initially charged and the charge plates may unequally influence entering drops, the left pivotal sidestream scupper 1620L, the center non-pivotal aspirator 1620C, and the right pivotal sidestream scupper 1620R are horizontally adjustable together from side to side together. An adjustment knob 1627 shown in FIGS. 16C-16D is provided to horizontally adjust the position of the scuppers 1620L-1620R and the center aspirator 1620C together along the drive shaft 1622. Accordingly, without charges deflecting the stream of drops, the center non-pivotal aspirator 1620C can be centered under the center stream of drops of sample fluid with an adjustment to direct them into the tub and down the drain for aspiration out from the cell sorter through the waste outlet.

As mentioned herein, the deflected drops pass through the drop slot 1625 in the case 1600 for collection in the drop collection chamber 128 below the deflection unit 122. Coupled to the base of the case 1600 of the deflection unit 122 is a collection retainer 1632 in the drop collection chamber 128. A sort collection holder 1630 can be slid into the collection retainer 1632 in the drop collection chamber 128. A plurality of test tubes 34, such as shown in FIG. 1A, may be inserted into the openings 1631 in the sort collection holder 1630 to receive the drops sorted out by the cell sorter. As shown in FIG. 16B, the openings 1631 are aligned (front to back in depth) with the drop slot 1625 such that test tubes mounted therein can capture drops of sample fluid.

Drops in one or more left deflected stream paths may be received in test tubes to the left of center. Drops in one or more right deflected stream paths may be received in test tubes to the right of center. FIG. 16C illustrates a four tube sort collection holder 1652 coupled to the base of the case 1600 with four openings 1653 to hold four test tubes, two test tubes to receive drops in two left deflected stream paths and two test tubes to receive drops in two right deflected stream paths.

FIG. 16D illustrates a plate guide 1642 instead of a tube collection retainer. The plate guide 1642 has a stream path opening 1643 in which selected drops fall through and out of the plate guide. A plate 35, such as shown in FIG. 1A, with a plurality of wells is moved around underneath the plate guide by the loading system to catch drops in the one or more wells. A plate can have a plurality of wells (e.g., 32 or 64) in which to capture drops with different types of cells/particles. The plate is moved to align a selected well underneath the stream path opening 1643 to receive the drops of sample fluid with the desired cells/particles.

Sample Input Station

Figure 17A:
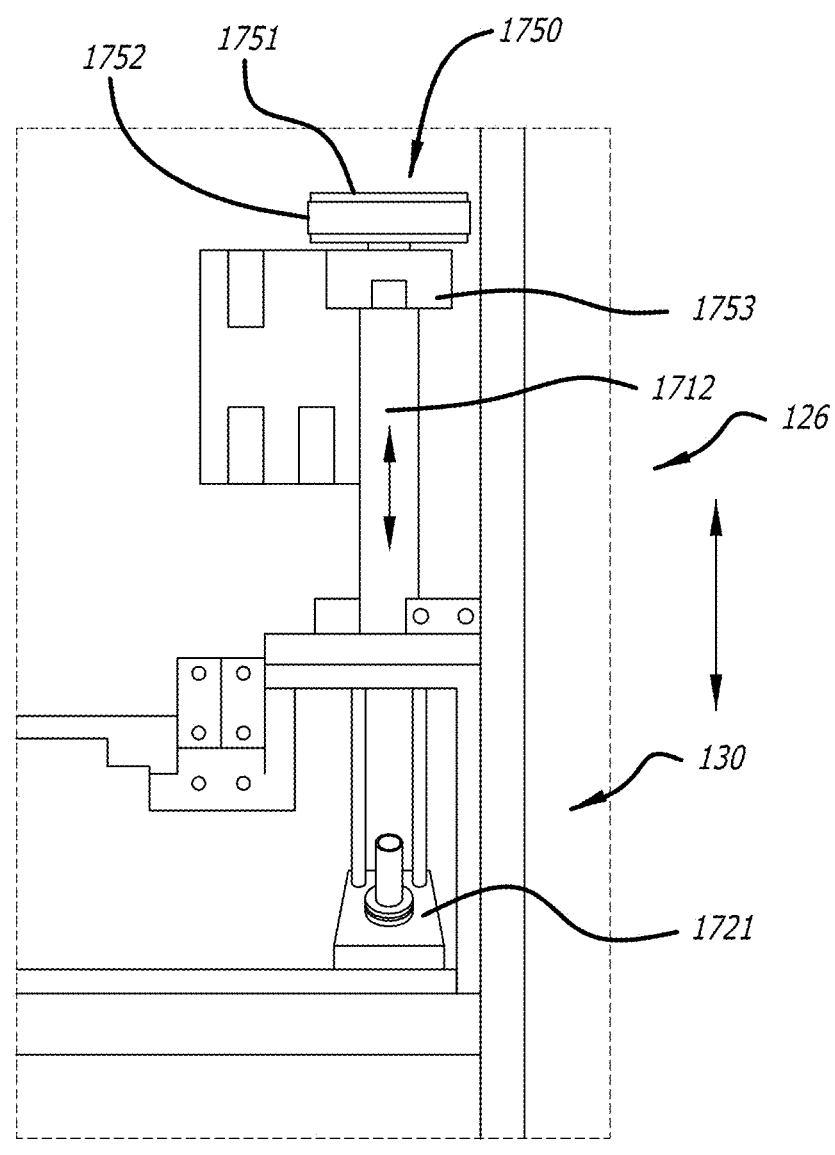
FIGS. 17A-17C are views of the sample input station (SIS) of the compact cell sorter system.
Figure 17B:
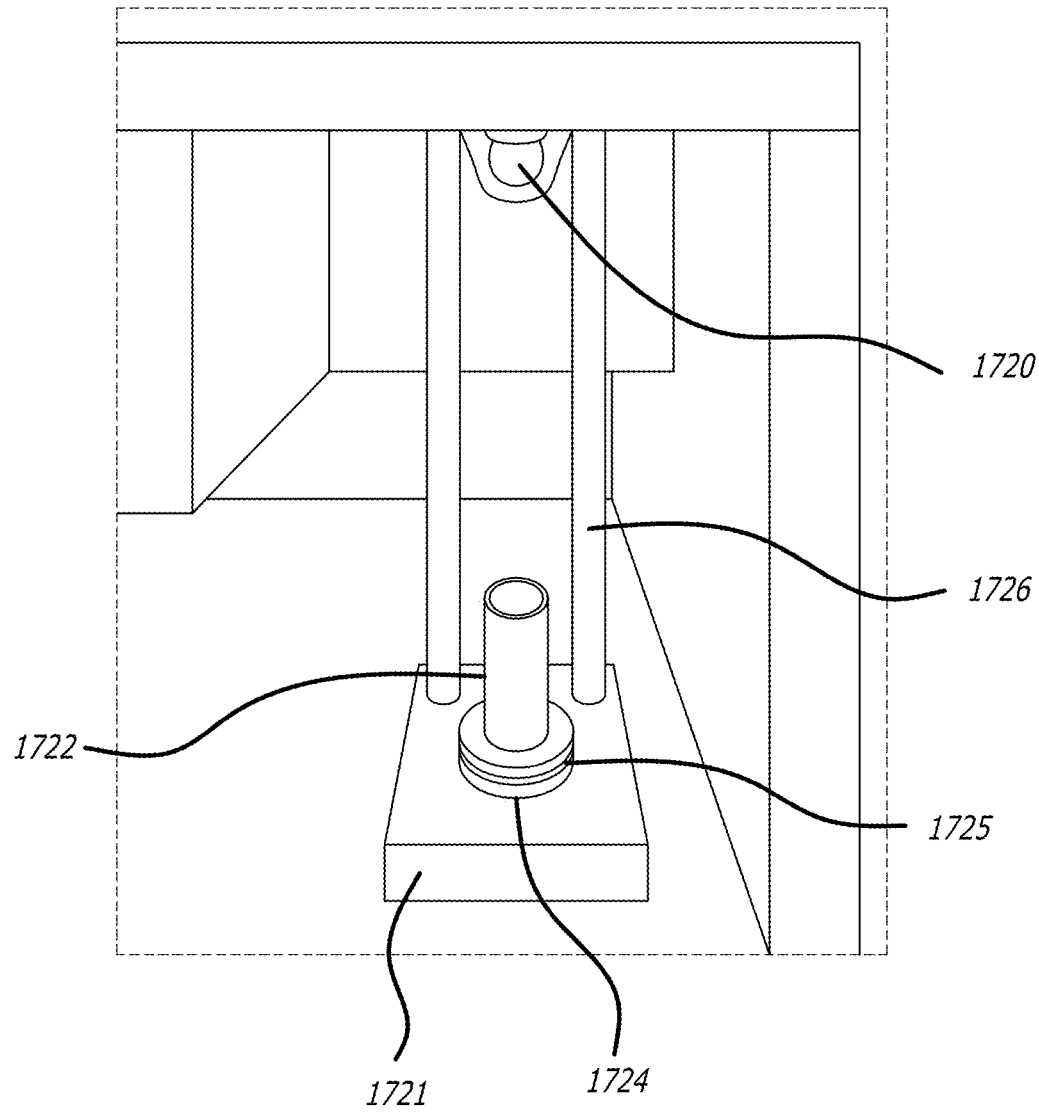
Figure 17C:
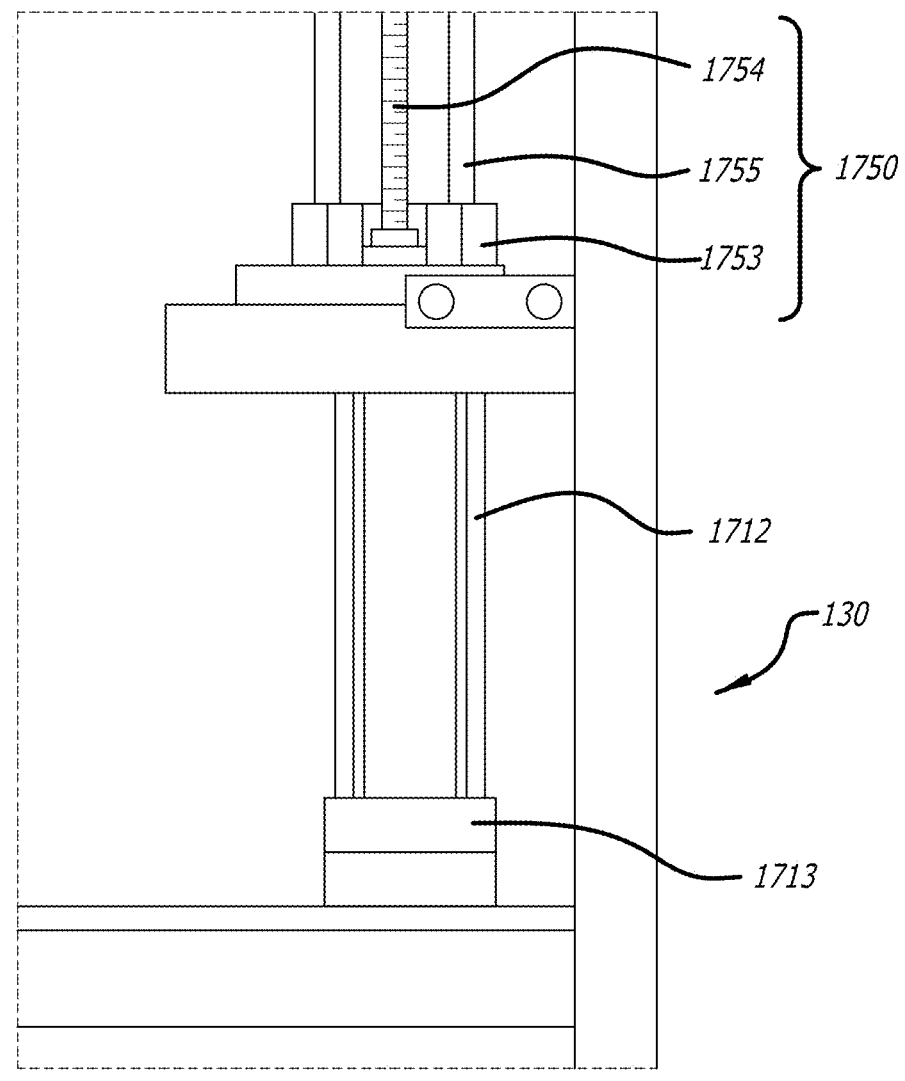

Referring now to FIGS. 17A-17C, the sample input station (SIS) 130 is shown. The sample input station (SIS) 130 includes a moveable pressure chamber (pressure cylinder) 126 with a chamber body 1712 that moves up and down by a threaded drive mechanism 1750 guided by a pair of guide rods 1750. The SIS 130 further includes, without limitation, an aspirator 1720, a tube holder 1722, and an agitation stage 1724.

FIG. 17A-17B illustrate an open position of the pressure chamber (pressure cylinder) 126 of the sample input station (SIS) 130. In contrast, FIG. 17C illustrates the closed position of the pressure chamber (pressure cylinder) 126. The chamber 1712 is driven down into the closed position over the agitation stage 1724 as shown in FIG. 17B. A top switch 1902 and a bottom switch 1903 (see FIG. 19) are used to sense the two positions (open and closed) of chamber body 1712 over which the threaded drive mechanism 1750 can run and the points at which it should stop.

Sample test tubes (e.g., Fluorescence Activated Cell Sorting (FACS) tubes) can be mounted in the tube holder 1722. A cell strainer may be used to filter out certain types of cells. The moveable pressure chamber (pressure cylinder) 126 includes a sample input tube 1912 that is insertable into the test tubes as it is lowered into closed position. The sample input tube 1912 can be flushed by a fluid, such as water or sheath fluid, before reusing the sample input tube on the next test tube. With the moveable pressure chamber (pressure cylinder) 126 in the down position, the air in the moveable pressure chamber (pressure cylinder) 126 can be pressurized to force sample fluid into the sample input tube 1912.

As shown in FIG. 17C, the drive mechanism 1750 includes a male threaded lead screw 1754 engaged with a female threaded nut in a platform 1753. The platform 1753 is coupled to the chamber body 1712 at the bottom by means of a single guide rod and a base plate to raise and lower the pressure chamber (pressure cylinder) 126 as the drive mechanism is activated. The platform 1753 includes a pair of openings over a pair of upper guide rods 1755 to maintain the orientation of the platform and guide it up and down. As shown in FIG. 17A, a driven pulley 1751 is mounted near an end of a threaded lead screw of the threaded drive mechanism 1750. A continuous (circular) belt 1752 is mounted to the driven pulley 1751. At the opposite end of the belt 1752, in the back of the system 100, a drive pulley is coupled to a shaft of a reversable electric motor to rotate the belt and pulley 1751 to turn the threaded lead screw 1754 until reaching the top and bottom switches. The bottom base of the chamber body 1712 is coupled to the threaded nut platform 1753 with a single guide rod. The threaded lead screw 1754 is coupled to the threaded nut platform. A bottom open end of the chamber body 1712 is coupled to a sealing ring 1713 to assist in sealing off the chamber around the agitation stage and its O-ring.

The SIS 130 further includes an aspirator 1720 to evacuate out aerosols and fluids from the test tube as waste. The SIS 130 further includes a tube holder 1722, and an agitation stage 1724, and a pair of guide rods 1726 mounted to a base 1721. The agitation stage 1724 has an O-ring seal 1726 to seal against the inside surface of the cylindrical wall of the chamber body (a pressure cylinder) 1712. As its name implies, the agitation stage 1724 can be rotated to agitate a test tube in the test tube holder 1722 and any sample fluid with its cells/particles in the test tube.

The DDU chamber 128 and the SIS 130 are in the same cavity formed by the case of the system 100. The air in the cavity can be conditioned to a desired temperature and filtered to avoid contamination. One or more fans and at least one heating/air conditioning element force air through air filters and maintain a desirable range of temperatures of the sample in the SIS 130 and the sorted cells/molecules in the DDU chamber 128. To avoid disturbing drops being collected, the input air flow comes into the shared cavity nearer the SIS 130. The DDU chamber 128 and SIS 130 are under negative pressure from a vacuum to additionally help prevent cells/molecules/gases from escaping out of the cell sorter into the ambient air of the environment.

FIG. 18 is a schematic diagram of the central source pressure-based cytometer fluidics system 1800 during an operation for a start stream path 1802 of sheath fluid. The pressure chamber 126 is coupled to the flow cell 124 via a pressure valve P2 and a flow meter 1802.

Figure 19:
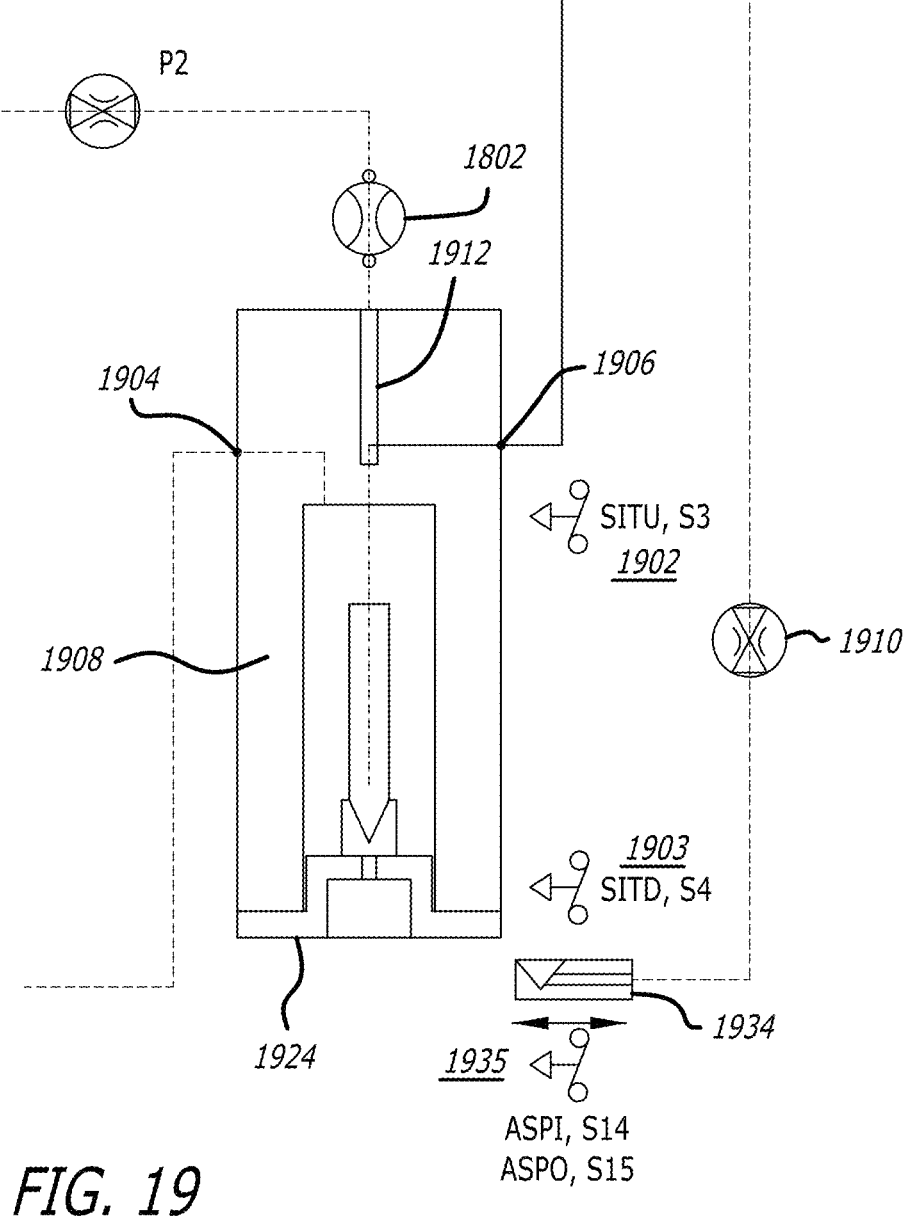
FIG. 19 is a schematic diagram of the pressure chamber and system of the sample input station (SIS) of the compact cell sorter system.

FIG. 19 is a schematic diagram of the pressure chamber 126. The pressure chamber 126 includes, without limitation, the following coupled components: a sample input station 130, an air inlet/vent port 1904, a sample injection tube (SIT) 1912, an outer diameter (OD) flush port 1906, a chamber body 1908, an aspirator pinch valve 1910, a stepper agitator 1924, a SIT aspirator 1934, a sample pinch valve P2, and a flow meter 1802. Switches 1902,1903 are provided to are used to sense the two positions (open and closed) of chamber body 1908. Switch 1935 is provided to sense the location of the SIT aspirator 1934 to evacuate fluids from the sample test tube.

Advantages

There are a number of advantages to the cell sorter 100, its assemblies and sub-assemblies. The cell sorter 100 is designed to be used with lower cost components (e.g., PEEK nozzle body; standard O-ring seals, fewer components) to make it less expensive to purchase and maintain. The cell sorter 100 is designed to require less maintenance and fewer service calls due to better isolation (e.g., glass SIT, loading system) from fluids. Some of the maintenance has been made easier to perform (e.g., replacement of nozzle O-ring seal) such that the user can perform maintenance on his/her own. Accordingly, maintenance costs of the cell sorter 100 are expected to be lower.

This disclosure contemplates other embodiments or purposes. It will be appreciated that the embodiments of the invention can be practiced by other means than that of the described embodiments, which are presented in this description for purposes of illustration and not of limitation. The specification and drawings are not intended to limit the exclusionary scope of this patent document. It is noted that various equivalents for the particular embodiments discussed in this description may be practiced by the claimed invention as well. That is, while specific embodiments of the invention have been described, it is evident that many alternatives, modifications, permutations and variations will become apparent in light of the foregoing description. Accordingly, it is intended that the claimed invention embrace all such alternatives, modifications and variations as fall within the scope of the appended claims. The fact that a product, process, or method exhibits differences from one or more of the described exemplary embodiments does not mean that the product or process is outside the scope (literal scope and/or other legally-recognized scope) of the following claims.

What is claimed is:

1. A system for flow cytometry or cell sorting, the system comprising:

a fluidics system under pressure to cause a sheath fluid and a sample biological fluid to flow, the fluidics system including a gas bubble remover eliminating gas bubbles in the sheath fluid;

a flow cell coupled in communication with the fluidics system to receive the sheath fluid, wherein a sample biological fluid flows with cells or particles through the flow cell to be surrounded by the sheath fluid and formed into drops, the flow cell having a conductive hose fitting to selectively receive a charge and transfer the charge to a desired drop for sorting as a charged drop, the flow cell further having a nozzle assembly through which fluid can pass, the nozzle assembly having a partial gland and a gasket positioned in the partial gland, the gasket having a portion extending beyond a surface of the nozzle assembly;

a deflection chamber under the flow cell to receive the drops of sample biological fluid and sheath fluid out of the flow cell, the deflection chamber to deflect the charge drop along one or more deflection paths;

a droplet deposition unit (DDU) system in communication with the deflection chamber to receive selectively deflected drops in the stream of the sample biological fluid with the one or more biological cells or particles into one or more containers; and wherein the flow cell further includes:

a flow cell body coupled in communication with the fluidics system to receive the sheath fluid and the sample biological fluid, the flow cell body having a funnel portion to form a fluid stream of the sample fluid surrounded by the sheath fluid out of an opening, a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein, the nozzle assembly selectively engaged with the cuvette, the nozzle assembly having a nozzle, a carriage assembly slidingly coupled to the flow cell body, the carriage assembly to slidingly receive the nozzle assembly, and a linkage pivotally coupled to the carriage assembly and the flow cell body, the linkage including a lever arm to selectively engage the nozzle with the cuvette to receive a fluid stream or selectively disengage the nozzle from the cuvette to service the nozzle.

2. The system of claim 1, wherein the flow cell includes a flow cell body coupled in communication with the fluidics system to receive the sheath fluid, the flow cell body having a chamber with a circular cylindrical portion and a funnel portion, the funnel portion to form a fluid stream of the sample fluid surrounded by the sheath fluid out of a bottom side opening;

a drop drive assembly coupled to the flow cell body, the drop drive assembly including a glass sample injection tube (SIT) inserted into the chamber of the flow cell body and having a first end located in the funnel portion of the chamber, the glass sample injection tube having a second end coupled in communication with the fluidics system to receive the sample fluid and inject the sample fluid into the funnel portion of the chamber; and a cuvette coupled to a base of the flow cell body, the cuvette having a flow channel adjacent the bottom side opening of the flow cell body, the cuvette to receive the fluid stream of the sample fluid surrounded by the sheath fluid out of the bottom side opening, the cuvette being transparent to light and allowing the sample fluid to undergo interrogation in the flow channel by a plurality of different lasers to determine a plurality of different types of cells or particles in the sample fluid.

3. The system of claim 1, the flow cell further including:

a lever hinge formed to be statically coupled to the flow cell body;

a carriage release lever rotatably coupled to the lever hinge; and two lever arms rotatably coupled to the carriage release lever and to a carriage plate of the carriage assembly, wherein the two lever arms, the carriage plate, the carriage release lever, and the lever hinge have a kinematic linkage that enables a mount of the carriage assembly to maintain a vertical movement along the center axis.

4. The system of claim 1, the nozzle assembly further having:

a nozzle handle having a body with a gripping end and a nozzle end, the body having a through hole between top and bottom surfaces near the nozzle end with the partial gland in the top surface extending around the through hole, the partial gland having a slot extending out from the through hole to the nozzle end of the nozzle handle;

a nozzle insert positioned in a portion of the through hole of the body of the nozzle handle, the nozzle insert having a circular body with a center nozzle orifice concentric with the through hole to flow drops of a sample fluid, and a beveled ring in a top surface extending out from the circular body;

the gasket positioned in the partial gland against the beveled ring of the nozzle insert with a portion extending above the top surface of the nozzle insert and the top surface of the nozzle handle, the gasket to provide a seal around the center nozzle orifice; and, wherein the slot extending out from the partial gland to the nozzle end facilitates removal of the gasket.

5. The system of claim 1, the DDU system including a case or a housing with an open face surround by edges of the case, the case forming a portion of a containment chamber, the case having a top side opening aligned with the deflection chamber to receive the selectively deflected drops in the stream of the sample biological fluid into one or more containers in the containment chamber, a seal mounted around edges of the case, one or more hinges coupled to a bottom portion of the case, and a door coupled to the one or more hinges to pivot the door about the one or more hinges, the door when closed to press against the seal and close off the containment chamber from an external environment.

6. The system of claim 5, the DDU system including an electromagnetic lock comprising at least one electromagnet mounted to the case and a metal latch coupled to an inside surface of the door, wherein the metal latch is attracted to the at least one electromagnet when the door is closed and the at least one electromagnet is energized.

7. The system of claim 6, the DDU system including a magnetic lock comprising at least one magnet mounted to the case and a metal latch coupled to an inside surface of the door, wherein the metal latch is attracted to the at least one magnet when the door is closed.

8. The system of claim 1, the DDU system including a sort collection holder to hold one or more test tubes in respective one or more deflection paths to collect the drops of the sample biological fluid and sheath fluid in the one or more test tubes.

9. The system of claim 1, the DDU system including a plate guide having a channel to allow one deflection path to collect the drops of the sample biological fluid and sheath fluid into one well of a plurality of wells in a well plate.

10. The system of claim 1, further comprising:

an excitation optics system including a plurality of excitation channels each having a different laser device and one or more optical elements to direct different laser light to optical interrogation regions spaced apart along a line in a flow channel of the flow cell.

11. The system of claim 1, further comprising:
an excitation optics system including
    a first excitation channel having a first laser device emitting a first laser light to strike cells or particles attached to a first fluorescent dye; and
    a second excitation channel having a second laser device emitting a second laser light to strike cells or particles attached to a second fluorescent dye.

12. The system of claim 10, further comprising:
an emission optics system including a plurality of detector arrays configured to receive light corresponding to cells or particles that are struck by the different laser light.

13. The system of claim 10, further comprising:
an emission optics system including a plurality of detector arrays each having one or more optical elements to direct fluorescent light or scattered light to various electro-optical detectors.

14. A flow cytometer or cell sorter system, the system comprising:
    a flow cell coupled in communication with a fluidics system to receive a sheath fluid, wherein a sample fluid flows with cells or particles through the flow cell to be surrounded by the sheath fluid, the flow cell including
    a flow cell body coupled around a drop drive assembly to receive the sample fluid from a sample injection tube, the flow cell body coupled in communication with the fluidics system to receive the sheath fluid, the flow cell body having a funnel portion to form a fluid stream of the sample fluid surrounded by the sheath fluid out of an opening;
    a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein;
    a nozzle assembly selectively engaged with the cuvette, the nozzle assembly having a nozzle and a partial gland around the nozzle with an O-ring positioned in the partial gland and around the nozzle, the O-ring having a portion extending beyond a surface of the nozzle assembly, the O-ring being selectively pressed against a face of the cuvette around the channel, the nozzle receiving the sample stream from the cuvette and forming sample drops out of the nozzle assembly; and
    a carriage assembly slidingly coupled to the flow cell body, the carriage assembly to slidingly receive the nozzle assembly; and a linkage pivotally coupled to the carriage assembly and the flow cell body, the linkage including a lever arm to selectively disengage the nozzle with the cuvette to receive a fluid stream and selectively disengage the nozzle from the cuvette to repair or replace the nozzle.

15. The system of claim 14, further comprising:
a fluidics system under pressure to cause a sheath fluid and a sample fluid to flow, the fluidics system including a gas bubble remover eliminating gas bubbles in the sheath fluid.

16. The system of claim 15, wherein the flow cell further includes
a drop drive assembly including a sample injection tube (SIT), the sample injection tube coupled in communication with the fluidics system to receive the sample fluid.

17. The system of claim 14, further comprising:
a lever hinge formed to be statically coupled to the flow cell body;
a carriage release lever rotatably coupled to the lever hinge; and
two lever arms rotatably coupled to the carriage release lever and to a carriage plate of the carriage assembly, wherein the two lever arms, the carriage plate, the carriage release lever, and the lever hinge have a kinematic linkage that enables a mount of the carriage assembly to maintain a vertical movement along the center axis.

18. The system of claim 17, wherein the two lever arms include
a left lever arm having an end rotatably coupled to a left side of the carriage release lever and another end rotatably coupled to a left side of the carriage plate, and
a right lever arm having an end rotatably coupled to a right side of the carriage release lever and another end rotatably coupled to a right side of the carriage plate.

19. The system of claim 17, wherein
the carriage release lever is engaged by moving the carriage release lever in such a way that the kinematic linkage causes the mount to move upward toward the lower side of the cuvette, and
when the carriage release is engaged, the gasket is pressed against the cuvette to cause a seal between the cuvette and the nozzle insert.

20. The system of claim 17, wherein
the carriage release lever is disengaged by moving the carriage release lever in such a way that the kinematic linkage causes the mount to move downward away from the lower side of the cuvette, and
when the carriage release is disengaged, the mount is positioned to register or unregister the nozzle assembly.

* * * * *